United States Patent
Gohl et al.

(10) Patent No.: US 11,767,554 B2
(45) Date of Patent: Sep. 26, 2023

(54) SIZE STANDARDS FOR NEXT-GENERATION SEQUENCING

(71) Applicant: REGENTS OF THE UNIVERSITY OF MINNESOTA, Minneapolis, MN (US)

(72) Inventors: Daryl M. Gohl, Minneapolis, MN (US); Kenneth B. Beckman, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 359 days.

(21) Appl. No.: 16/967,687

(22) PCT Filed: Feb. 14, 2019

(86) PCT No.: PCT/US2019/017985
§ 371 (c)(1),
(2) Date: Aug. 5, 2020

(87) PCT Pub. No.: WO2019/161039
PCT Pub. Date: Aug. 22, 2019

(65) Prior Publication Data
US 2021/0032694 A1 Feb. 4, 2021

Related U.S. Application Data

(60) Provisional application No. 62/630,463, filed on Feb. 14, 2018.

(51) Int. Cl.
*C12P 19/34* (2006.01)
*C12Q 1/6869* (2018.01)
*C12N 15/10* (2006.01)

(52) U.S. Cl.
CPC ....... *C12Q 1/6869* (2013.01); *C12N 15/1065* (2013.01)

(58) Field of Classification Search
CPC .................................................. C12Q 1/6869
See application file for complete search history.

(56) References Cited

U.S. PATENT DOCUMENTS

| | | | |
|---|---|---|---|
| 5,824,516 A | 10/1998 | Collu | |
| 11,286,518 B2 * | 3/2022 | Beckman | C12Q 1/6851 |
| 2002/0102548 A1 | 8/2002 | Zimmermann | |
| 2005/0095610 A1 | 5/2005 | Kuo | |
| 2008/0305475 A1 | 12/2008 | Yamashita | |
| 2015/0133312 A1 * | 5/2015 | Bielas | C12Q 1/6858 |
| | | | 435/6.12 |
| 2017/0327882 A1 | 11/2017 | Betts | |
| 2019/0177781 A1 | 6/2019 | Beckman | |

FOREIGN PATENT DOCUMENTS

WO 2017192974 A1 11/2017

OTHER PUBLICATIONS

Santiago A, et al. Processing faecal samples: a step forward for standards in microbial community analysis. BMC Microbiol. 2014;14:112.
Seqmatic. TailorMix Dual-Indexed PhiX Control Library (Denatured). Webpage. Version accessed Aug. 31, 2016. Available online at http://web.archive.org/web/20160831091506/http://www.seqmatic.com/products/tailormix-dual-indexed-phix/.
Shalem O. et al. High-throughput functional genomics using CRISPR-Cas9. Nat Rev Genet. 2015;16:299-311.
Shalem O. et al. Genome-Scale CRISPR-Cas9 Knockout Screening in Human Cells. Science (80-. ). 343, 84-87 (2014).
Sims, D. et al. High-throughput RNA interference screening using pooled shRNA libraries and next generation sequencing. Genome Biol. 12, R104 (2011).
Smith, A. M. et al. Quantitative phenotyping via deep barcode sequencing. Genome Res. 19, 1836-42 (2009).
Snyder MW, et al. Cell-free DNA comprises an in vivo nucleosome footprint that informs its tissues-of-origin. Cell. 2016;164:57-68.
Strezoska, Z. et al. Optimized PCR conditions and increased shRNA fold representation improve reproducibility of pooled shRNA screens. PLoS One 7, e42341 (2012).
Tan, G., et al. "Long fragments achieve lower base quality in Illumina paired-end sequencing." NatSR 9 (2019): 2856.
Taylor, D. L. et al. Accurate Estimation of Fungal Diversity and Abundance through Improved Lineage-Specific Primers Optimized for Illumina Amplicon Sequencing. Appl. Environ. Microbiol. 82, 7217-7226 (2016).
Trapnell C, et al. Transcript assembly and quantification by RNA-Seq reveals unannotated transcripts and isoform switching during cell differentiation. Nat Biotechnol. 2010;28:511-515.
Van Opijnen, T. et al Transposon insertion sequencing: a new tool for systems-level analysis of microorganisms. Nat. Rev. Microbiol. 11, 435-442 (2013).
Wang T, et al. Genetic screens in human cells using the CRISPR-Cas9 system. Science. 2014;343:80-84.
Woese, C. R. et al. Secondary structure model for bacterial 16S ribosomal RNA: phylogenetic, enzymatic and chemical evidence. Nucleic Acids Res. 8, 2275-2294 (1980).
Zhang Y, et al. Model-based analysis of ChIP-Seq (MACS) Genome Biol. 2008;9:R137.
Aird, D. et al. Analyzing and minimizing PCR amplification bias in Illumina sequencing libraries. Genome Biol. 12, R18(2011).
Andrews KR, et al. Harnessing the power of RADseq for ecological and evolutionary genomics. Nat Rev Genet. 2016;17:81-92.
Bhang, H. C. et al. Studying clonal dynamics in response to cancer therapy using high-complexity barcoding. Nat. Med. 21, 440-448 (2015).

(Continued)

*Primary Examiner* — Kenneth R Horlick
(74) *Attorney, Agent, or Firm* — QUARLES & BRADY LLP

(57) ABSTRACT

Provided herein are synthetic size standards that allow one to detect size bias in a sample that includes a plurality of polynucleotides. The size standards can provide an internal control to detect and correct for size bias in data obtained after manipulating and/or processing of sample polynucleotide. Also provided herein are methods for detecting size bias in a sample or in a sequencing run.

13 Claims, 11 Drawing Sheets

Specification includes a Sequence Listing.

(56) References Cited

OTHER PUBLICATIONS

Bolger AM, et al. Trimmomatic: a flexible trimmer for Illumina sequence data. Bioinformatics. 2014,30:2114-2120.
Buenrostro JD, et al. Transposition of native chromatin for fast and sensitive epigenomic profiling of open chromatin, DNA-binding proteins and nucleosome position. Nat Methods. 2013;10:1213-1218.
Buenrostro JD, et al. ATAC-seq: a method for assaying chromatin accessibility genome-wide. In: Current Protocols in Molecular Biology. Hoboken: Wiley; 2015. pp. 21.29.1-21.29.9.
Caporaso, J. G. et al. Global patterns of 16S rRNA diversity at a depth of millions of sequences per sample. Proc. Natl. Acad. Sci. U. S. A. 108 Suppl, 4516-22 (2011).
Chang H, et al. TAIL-seq: genome-wide determination of poly(A) tail length and 3' end modifications. Mol Cell. 2014;53:1044-1052.
Clark, J. M. Novel non-templated nucleotide addition reactions catalyzed by procaryotic and eucaryotic DNA polymerases. Nucleic Acids Res. 16, 9677-9686 (1988).
Cock, P. J. A. et al. Biopython: freely available Python tools for computational molecular biology and bioinformatics. Bioinformatics 25, 1422-3 (2009).
Danecek P, et al. The variant call format and VCFtools. Bioinformatics. 2011;27:2156-2158.
Engler C, et al. A one pot, one step, precision cloning method with high throughput capability. PLoS One. 2008;3: e3647.
Engler C, et al. Golden Gate shuffling: a one-pot DNA shuffling method based on type IIs restriction enzymes. PLoS One. 2009;4:e5553.
Garrison E, et al. Haplotype-based variant detection from short-read sequencing. arXiv preprint arXiv:1207.3907 (2012).
Geiss, G. K. et al. Direct multiplexed measurement of gene expression with color-coded probe pairs. Nat. Biotechnol. 26, 317-325 (2008).
Gohl DM, et al. A versatile in vivo system for directed dissection of gene expression patterns. Nat Methods. 2011;8:231-237.
Gohl DM, et al. Measuring sequencer size bias using REcount: a novel method for highly accurate Illumina sequencing-based quantification. Data sets. SRA BioProject. 2019. https://www.ncbi.nlm.nih.gov/bioproject/?term=PRJNA431017. Accessed Apr. 8, 2019.
Gohl DM, et al. Measuring sequencer size bias using REcount: a novel method for highly accurate Illumina sequencing-based quantification. Genome Biology 20.1 (2019): 85-85.
Gohl DM, et al. Measuring sequencer size bias using REcount: a novel method for highly accurate Illumina sequencing-based quantification. Source code and supplemental data files. GitHub. 2019. https://github.com/darylgohl/REcount. Accessed Apr. 8, 2019.
Gohl DM, et al. Systematic improvement of amplicon marker gene methods for increased accuracy in microbiome studies. Nat. Biotechnol. 34, 942-949 (2016).
Hanna RE, et al. A case of mistaken identity. Nat Biotechnol. 2018;36(9):802-804.
Hindson, B. J. et al. High-Throughput Droplet Digital PCR System for Absolute Quantitation of DNA Copy Number. Anal. Chem. 83, 8604-8610 (2011).
Illumina. Nextera Library Validation and Cluster Density Optimization. Technical Note. 2014.
Illumina. Considerations when Migrating non-Illumina libraries between sequencing platforms. May 15, 2020. Available online at support.illumina.eom/bulletins/2016/10/considerations-when-migrating-nonillumina-libraries-between-sequencing-platforms.html.
Illumina. PhiX Control v3 webpage. Version dated Jul. 21, 2017. Available online at http://web-old.archive.org/web/20170721055156/ https://www.illumina.com/products/by-type/sequencing-kits/cluster-gen-sequencing-reagents/phix-control-v3.html.
International Searching Authority. International Search Report and Written Opinion for application PCT/US2019/017985, dated Apr. 17, 2019. 12 pages.
Jumpstart Consortium Human Microbiome Project Data Generation Working Group. "Evaluation of 16S rDNA-based community profiling for human microbiome research." PloS one 7.6 (2012): e39315.
Kebschull, J. M. et al. High-Throughput Mapping of Single-Neuron Projections by Sequencing of Barcoded RNA. Neuron 91, 975-987 (2016).
Kim D, et al. HISAT: a fast spliced aligner with low memory requirements. Nat Methods. 2015;12:357-360.
Kinde I, Wu J, Papadopoulos N, Kinzler KW, Vogelstein B. Detection and quantification of rare mutations with massively parallel sequencing. Proc Natl Acad Sci U S A. 2011;108:9530-9535.
Kivioja, T. et al. Counting absolute numbers of molecules using unique molecular identifiers. Nat. Methods 9, 72 (2011).
Koike-Yusa H, et al. Genome-wide recessive genetic screening in mammalian cells with a lentiviral CRISPR-guide RNA library. Nat Biotechnol. 2014;32:267-273.
Lagha M, et al. Pax3 regulation of FGF signaling affects the progression of embryonic progenitor cells into the myogenic program. Genes Dev. 2008;22:1828-1837.
Langmead B, et al. Fast gapped-read alignment with bowtie 2. Nat Methods. 2012;9:357-359.
Li H, et al. Fast and accurate long-read alignment with Burrows-Wheeler transform. Bioinformatics. 2010;26:589-595.
Li H, et al. The sequence alignment/map format and SAMtools. Bioinformatics. 2009;25:2078-2079.
Liao Y, et al. The Subread aligner: fast, accurate and scalable read mapping by seed-and-vote. Nucleic Acids Res. 2013;41:e108.
Magli A, et al. Time-dependent Pax3-mediated chromatin remodeling and cooperation with Six4 and Tead2 specify the skeletal myogenic lineage in developing mesoderm. PLoS Biol. 2019;17:e3000153.
Magli A, et al. Methods in molecular biology (Clifton, N.J.) 2016. Myogenic progenitors from mouse pluripotent stem cells for muscle regeneration; pp. 191-208.
Martin M. Cutadapt removes adapter sequences from high-throughput sequencing reads. EMBnet. J. 2011;17:10-12.
McKenna, A. et al. Whole-organism lineage tracing by combinatorial and cumulative genome editing. Science 353, aaf7907 (2016).
Methe, B. A., et al. "A framework for human microbiome research." nature 486.7402 (2012): 215.
Mouliere F, et al. Enhanced detection of circulating tumor DNA by fragment size analysis. Sci Transl Med. 2018;10: eaat4921.
Peikon, I. D. et al. Using high-throughput barcode sequencing to efficiently map connectomes. bioRxiv 99093 (2017). doi:10.1101/099093.
Polz, M. F. et al. Bias in Template to-Product Ratios in Multitemplate PCR. Appl. Envir. Microbiol. 64, 3724-3730 (1998).
Ponts, N. et al. Nucleosome landscape and control of transcription in the human malaria parasite. Genome Res. 20, 228-38 (2010).
Quinlan AR, et al. BEDTools: a flexible suite of utilities for comparing genomic features. Bioinformatics. 2010;26:841-842.
Robinson JT, et al. Integrative genomics viewer. Nat Biotechnol. 2011;29:24-26.
Rodriguez-Barrueco R, et al. Pooled shRNA screenings: experimental approach. Methods Mol Biol. 2013;980:353-370.
Sanger, F. et al. DNA sequencing with chain-terminating inhibitors. Proc. Natl. Acad. Sci. U. S. A. 74, 5463-7 (1977).

* cited by examiner

| Construct size | Gene | GC content (%) | Construct size | Gene | GC content (%) | Construct size | Gene | GC content (%) |
|---|---|---|---|---|---|---|---|---|
| 150 | 16S rRNA (E. coli) | 45.45 | 150 | GAPDH (D. melanogaster) | 45.45 | 150 | Tubulin (D. melanogaster) | 54.55 |
| 300 | 16S rRNA (E. coli) | 51.16 | 300 | GAPDH (D. melanogaster) | 43.02 | 300 | Tubulin (D. melanogaster) | 43.60 |
| 450 | 16S rRNA (E. coli) | 53.73 | 450 | GAPDH (D. melanogaster) | 40.99 | 450 | Tubulin (D. melanogaster) | 50.00 |
| 600 | 16S rRNA (E. coli) | 54.87 | 600 | GAPDH (D. melanogaster) | 47.25 | 600 | Tubulin (D. melanogaster) | 52.75 |
| 750 | 16S rRNA (E. coli) | 53.70 | 750 | GAPDH (D. melanogaster) | 50.16 | 750 | Tubulin (D. melanogaster) | 55.79 |
| 900 | 16S rRNA (E. coli) | 54.79 | 900 | GAPDH (D. melanogaster) | 52.59 | 900 | Tubulin (D. melanogaster) | 56.87 |
| 1050 | 16S rRNA (E. coli) | 55.31 | 1050 | GAPDH (D. melanogaster) | 55.31 | 1050 | Tubulin (D. melanogaster) | 56.29 |
| 1200 | 16S rRNA (E. coli) | 54.94 | 1200 | GAPDH (D. melanogaster) | 55.50 | 1200 | Tubulin (D. melanogaster) | 56.72 |
| 1350 | 16S rRNA (E. coli) | 54.66 | 1350 | GAPDH (D. melanogaster) | 55.65 | 1350 | Tubulin (D. melanogaster) | 56.87 |
| 1500 | 16S rRNA (E. coli) | 54.52 | 1500 | GAPDH (D. melanogaster) | 55.10 | 1500 | Tubulin (D. melanogaster) | 57.58 |

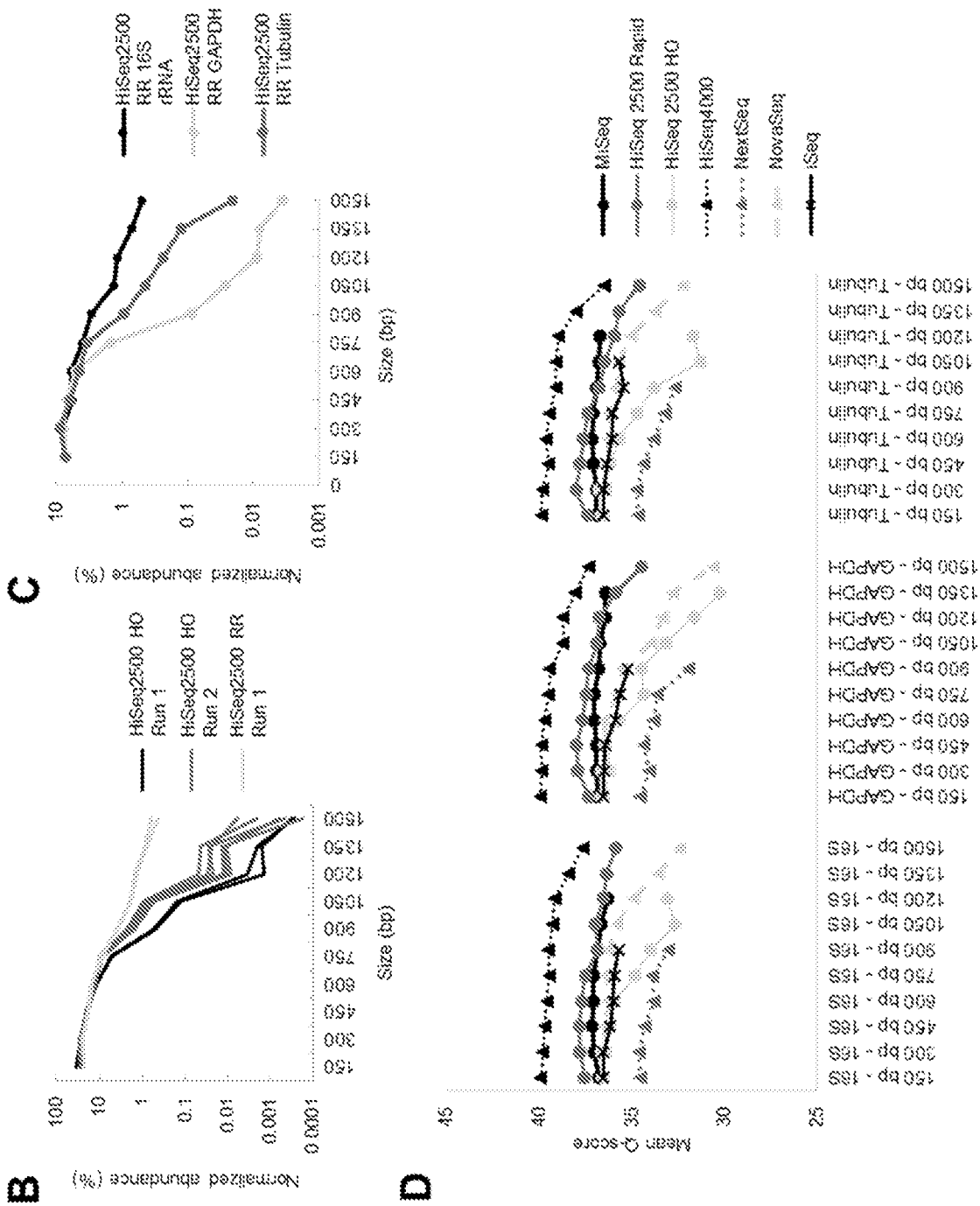
FIGS. 2A-2D, CONTINUED

B  HiSeq4000 run 1
Average size = 319 bp, Minimal material <300 bp

SEQUENCE LISTING

```
<160> NUMBER OF SEQ ID NOS: 185

<210> SEQ ID NO 1
<211> LENGTH: 58
<212> TYPE: DNA
<213> ORGANISM: Artificial Sequence
<220> FEATURE:
<223> OTHER INFORMATION: synthetic

<400> SEQUENCE: 1
aatgatacgg cgaccaccga gatctacact ctttccctac acgacgctct tccgatct        58

<210> SEQ ID NO 2
<211> LENGTH: 70
<212> TYPE: DNA
<213> ORGANISM: Artificial Sequence
<220> FEATURE:
<223> OTHER INFORMATION: synthetic

<400> SEQUENCE: 2
agatcggaag agcacacgtc tgaactccag tcacaatcag tctcgtatct cgtatgccgt        60
cttctgcttg                                                              70

<210> SEQ ID NO 3
<211> LENGTH: 74
<212> TYPE: DNA
<213> ORGANISM: Artificial Sequence
<220> FEATURE:
<223> OTHER INFORMATION: synthetic

<400> SEQUENCE: 3
ctgtctctta tacacatctg acgctgccga cgaatcacca ggtgtgtgta gatctcggtg        60
gtcgccgtat catt                                                         74

<210> SEQ ID NO 4
<211> LENGTH: 372
<212> TYPE: DNA
<213> ORGANISM: Artificial Sequence
<220> FEATURE:
<223> OTHER INFORMATION: synthetic
```

<400> SEQUENCE: 4

```
gagtcgacaa aatgatacgg cgaccaccga gatctacact ctttccctac acgacgctct    60
tccgatctga gcatgccgat ggtttgttaa agatcggaag agcacacgtc tgaactccag   120
tcacaatcag tctcgtatct cgtatgccgt cttctgcttg ttgtcgactc tagggataac   180
agggtaatga gtcgacaaca agcagaagac ggcatacgag attggtcaac gatagtctcg   240
tgggctcgga gatgtgtata agagacaggc cgcccgtcac agcacgtact gtctcttata   300
cacatctgac gctgccgacg aatcaccagg tgtgtgtaga tctcggtggt cgccgtatca   360
ttttgtcgac tc                                                       372
```

<210> SEQ ID NO 5
<211> LENGTH: 522
<212> TYPE: DNA
<213> ORGANISM: Artificial Sequence
<220> FEATURE:
<223> OTHER INFORMATION: synthetic

<400> SEQUENCE: 5

```
gagtcgacaa aatgatacgg cgaccaccga gatctacact ctttccctac acgacgctct    60
tccgatctag actatcgcct ttagcctcaa attgaagagt ttgatcatgg ctcagattga   120
acgctggcgg caggcctaac acatgcaagt cgaacggtaa caggaagaag cttgctcttt   180
gctgacgagt ggcggacggg tgagtaatgt ctgggaaact gcctgatgga gggggataac   240
agatcggaag agcacacgtc tgaactccag tcacaatcag tctcgtatct cgtatgccgt   300
cttctgcttg ttgtcgactc tagggataac agggtaatga gtcgacaaca agcagaagac   360
ggcatacgag attggtcaac gatagtctcg tgggctcgga gatgtgtata agagacaggc   420
agctgttaga gacgaatcct gtctcttata cacatctgac gctgccgacg aatcaccagg   480
tgtgtgtaga tctcggtggt cgccgtatca ttttgtcgac tc                      522
```

<210> SEQ ID NO 6
<211> LENGTH: 672
<212> TYPE: DNA
<213> ORGANISM: Artificial Sequence
<220> FEATURE:
<223> OTHER INFORMATION: synthetic

<400> SEQUENCE: 6

```
gagtcgacaa aatgatacgg cgaccaccga gatctacact ctttccctac acgacgctct    60
tccgatcttg atgtatatag ccggcggcaa attgaagagt ttgatcatgg ctcagattga   120
acgctggcgg caggcctaac acatgcaagt cgaacggtaa caggaagaag cttgctcttt   180
gctgacgagt ggcggacggg tgagtaatgt ctgggaaact gcctgatgga gggggataac   240
tactggaaac ggtagctaat accgcataac gtcgcaagac caaagagggg gaccttcggg   300
cctcttgcca tcgatgtgcc cagatggga ttagctagta ggtggggtaa cggctcacct   360
aggcgacgat ccctagctgg tctgagagga agatcggaag agcacacgtc tgaactccag   420
tcacaatcag tctcgtatct cgtatgccgt cttctgcttg ttgtcgactc tagggataac   480
agggtaatga gtcgacaaca agcagaagac ggcatacgag attggtcaac gatagtctcg   540
tgggctcgga gatgtgtata agagacaggg acaaacagaa atatcacgct gtctcttata   600
cacatctgac gctgccgacg aatcaccagg tgtgtgtaga tctcggtggt cgccgtatca   660
ttttgtcgac tc                                                       672
```

<210> SEQ ID NO 7
<211> LENGTH: 822
<212> TYPE: DNA
<213> ORGANISM: Artificial Sequence
<220> FEATURE:
<223> OTHER INFORMATION: synthetic

<400> SEQUENCE: 7

```
gagtcgacaa aatgatacgg cgaccaccga gatctacact ctttccctac acgacgctct      60
tccgatctca acggaacgtg cactgcagaa attgaagagt ttgatcatgg ctcagattga     120
acgctggcgg caggcctaac acatgcaagt cgaacggtaa caggaagaag cttgctcttt     180
gctgacgagt ggcggacggg tgagtaatgt ctgggaaact gcctgatgga gggggataac     240
tactggaaac ggtagctaat accgcataac gtcgcaagac caaagagggg gaccttcggg     300
cctcttgcca tcggatgtgc ccagatggga ttagctagta ggtggggtaa cggctcacct     360
aggcgacgat ccctagctgg tctgagagga tgaccagcca cactggaact gagacacggt     420
ccacacacct acggaggca gcagtgggga atattgcaca atgggcgcaa gcctgatgca     480
gccatgccgc gtgtatgaag aaggccttcg ggttgtaaag tactttcagc ggggaggaag     540
agatcggaag agcacacgtc tgaactccag tcacaatcag tctcgtatct cgtatgccgt     600
cttctgcttg ttgtcgactc tagggataac agggtaatga gtcgacaaca agcagaagac     660
ggcatacgag attggtcaac gatagtctcg tgggctcgga gatgtgtata agagacaggg     720
ccaccgtaaa cagtgcgact gtctcttata cacatctgac gctgccgacg aatcaccagg     780
tgtgtgtaga tctcggtggt cgccgtatca ttttgtcgac tc                         822
```

<210> SEQ ID NO 8
<211> LENGTH: 972
<212> TYPE: DNA
<213> ORGANISM: Artificial Sequence
<220> FEATURE:
<223> OTHER INFORMATION: synthetic

<400> SEQUENCE: 8

```
gagtcgacaa aatgatacgg cgaccaccga gatctacact ctttccctac acgacgctct      60
tccgatctaa tgtgagcgta tcaggagaaa attgaagagt ttgatcatgg ctcagattga     120
acgctggcgg caggcctaac acatgcaagt cgaacggtaa caggaagaag cttgctcttt     180
gctgacgagt ggcggacggg tgagtaatgt ctgggaaact gcctgatgga gggggataac     240
tactggaaac ggtagctaat accgcataac gtcgcaagac caaagagggg gaccttcggg     300
cctcttgcca tcggatgtgc ccagatggga ttagctagta ggtggggtaa cggctcacct     360
aggcgacgat ccctagctgg tctgagagga tgaccagcca cactggaact gagacacggt     420
ccacacacct acggaggca gcagtgggga atattgcaca atgggcgcaa gcctgatgca     480
gccatgccgc gtgtatgaag aaggccttcg ggttgtaaag tactttcagc ggggaggaag     540
ggagtaaagt taatacccttt gctcattgac gttacccgca gaagaagcac cggctaactc     600
cgtgccagca gccgcggtaa tacggagggt gcaagcgtta atcggaatta ctgggcgtaa     660
agcgcacgca ggcggtttgt taagtcgat agatcggaag agcacacgtc tgaactccag     720
tcacaatcag tctcgtatct cgtatgccgt cttctgcttg ttgtcgactc tagggataac     780
agggtaatga gtcgacaaca agcagaagac ggcatacgag attggtcaac gatagtctcg     840
```

| tgggctcgga gatgtgtata agagacagta gcgcccacag caagtgatct gtctcttata | 900 |
| cacatctgac gctgccgacg aatcaccagg tgtgtgtaga tctcggtggt cgccgtatca | 960 |
| ttttgtcgac tc | 972 |

<210> SEQ ID NO 9
<211> LENGTH: 1122
<212> TYPE: DNA
<213> ORGANISM: Artificial Sequence
<220> FEATURE:
<223> OTHER INFORMATION: synthetic

<400> SEQUENCE: 9

| gagtcgacaa aatgatacgg cgaccaccga gatctacact ctttccctac acgacgctct | 60 |
| tccgatctcg gcgggtagta cctgtaccaa attgaagagt ttgatcatgg ctcagattga | 120 |
| acgctggcgg caggcctaac acatgcaagt cgaacggtaa caggaagaag cttgctcttt | 180 |
| gctgacgagt ggcggacggg tgagtaatgt ctgggaaact gcctgatgga gggggataac | 240 |
| tactggaaac ggtagctaat accgcataac gtcgcaagac caaagagggg gaccttcggg | 300 |
| cctcttgcca tcggatgtgc ccagatggga ttagctagta ggtggggtaa cggctcacct | 360 |
| aggcgacgat ccctagctgg tctgagagga tgaccagcca cactggaact gagacacggt | 420 |
| ccacacacct acgggaggca gcagtgggga atattgcaca atgggcgcaa gcctgatgca | 480 |
| gccatgccgc gtgtatgaag aaggccttcg ggttgtaaag tactttcagc ggggaggaag | 540 |
| ggagtaaagt taatacccttt gctcattgac gttacccgca gaagaagcac cggctaactc | 600 |
| cgtgccagca gccgcggtaa tacggagggt gcaagcgtta atcggaatta ctgggcgtaa | 660 |
| agcgcacgca ggcggttttgt taagtcagat gtgaaatccc cggctcaac ctgggaactg | 720 |
| catctgatac tggcaagctt gtcacacgta gaggggggta gaattccagg tgtagcggtg | 780 |
| aaatgcgtag agatctggag gaataccggt ggcgaaggcg gcccctgga cgaagactga | 840 |
| agatcggaag agcacacgtc tgaactccag tcacaatcag tctcgtatct cgtatgccgt | 900 |
| cttctgcttg ttgtcgactc tagggataac agggtaatga gtcgacaaca agcagaagac | 960 |
| ggcatacgag attggtcaac gatagtctcg tgggctcgga gatgtgtata agagacagac | 1020 |
| aagcccctaat gatgatagct gtctcttata cacatctgac gctgccgacg aatcaccagg | 1080 |
| tgtgtgtaga tctcggtggt cgccgtatca ttttgtcgac tc | 1122 |

<210> SEQ ID NO 10
<211> LENGTH: 1272
<212> TYPE: DNA
<213> ORGANISM: Artificial Sequence
<220> FEATURE:
<223> OTHER INFORMATION: synthetic

<400> SEQUENCE: 10

| gagtcgacaa aatgatacgg cgaccaccga gatctacact ctttccctac acgacgctct | 60 |
| tccgatctgt tctcctgcta cagaggttaa attgaagagt ttgatcatgg ctcagattga | 120 |
| acgctggcgg caggcctaac acatgcaagt cgaacggtaa caggaagaag cttgctcttt | 180 |
| gctgacgagt ggcggacggg tgagtaatgt ctgggaaact gcctgatgga gggggataac | 240 |
| tactggaaac ggtagctaat accgcataac gtcgcaagac caaagagggg gaccttcggg | 300 |
| cctcttgcca tcggatgtgc ccagatggga ttagctagta ggtggggtaa cggctcacct | 360 |
| aggcgacgat ccctagctgg tctgagagga tgaccagcca cactggaact gagacacggt | 420 |

| | |
|---|---:|
| ccacacacct acgggaggca gcagtgggga atattgcaca atgggcgcaa gcctgatgca | 480 |
| gccatgccgc gtgtatgaag aaggcctccg ggttgtaaag tactttcagc ggggaggaag | 540 |
| ggagtaaagt taatacccttt gctcattgac gttacccgca gaagaagcac cggctaactc | 600 |
| cgtgccagca gccgcggtaa tacgagggt gcaagcgtta atcggaatta ctgggcgtaa | 660 |
| agcgcacgca ggcggtttgt taagtcagat gtgaaatccc cgggctcaac ctgggaactg | 720 |
| catctgatac tggcaagctt gtcacacgta gaggggggta gaattccagg tgtagcggtg | 780 |
| aaatgcgtag agatctggag gaataccggt ggcgaaggcg gccccctgga cgaagactga | 840 |
| cgctcaggtg cgaaagcgtg gggagcaaac aggattagat accctggtag tccacgccgt | 900 |
| aaacgatgtc gacttggagg ttgtgccctt gaggcgtggc ttccggagct aacgcgttaa | 960 |
| gtcgaccgcc tggggagtac ggccgcaagg agatcggaag agcacacgtc tgaactccag | 1020 |
| tcacaatcag tctcgtatct cgtatgccgt cttctgcttg ttgtcgactc tagggataac | 1080 |
| agggtaatga gtcgacaaca agcagaagac ggcatacgag attggtcaac gatagtctcg | 1140 |
| tgggctcgga gatgtgtata agagacagac gctgataaat atcgagttct gtctcttata | 1200 |
| cacatctgac gctgccgacg aatcaccagg tgtgtgtaga tctcggtggt cgccgtatca | 1260 |
| ttttgtcgac tc | 1272 |

<210> SEQ ID NO 11
<211> LENGTH: 1422
<212> TYPE: DNA
<213> ORGANISM: Artificial Sequence
<220> FEATURE:
<223> OTHER INFORMATION: synthetic

<400> SEQUENCE: 11

| | |
|---|---:|
| gagtcgacaa aatgatacgg cgaccaccga gatctacact ctttccctac acgacgctct | 60 |
| tccgatctcc cacatgccgg aacgcaccaa attgaagagt ttgatcatgg ctcagattga | 120 |
| acgctggcgg caggcctaac acatgcaagt cgaacggtaa caggaagaag cttgctcttt | 180 |
| gctgacgagt ggcggacggg tgagtaatgt ctgggaaact gcctgatgga gggggataac | 240 |
| tactggaaac ggtagctaat accgcataac gtcgcaagac caaagagggg gaccttcggg | 300 |
| cctcttgcca tcggatgtgc ccagatggga ttagctagta ggtgggtaa cggctcacct | 360 |
| aggcgacgat ccctagctgg tctgagagga tgaccagcca cactggaact gagacacggt | 420 |
| ccacacacct acgggaggca gcagtgggga atattgcaca atgggcgcaa gcctgatgca | 480 |
| gccatgccgc gtgtatgaag aaggcctccg ggttgtaaag tactttcagc ggggaggaag | 540 |
| ggagtaaagt taatacccttt gctcattgac gttacccgca gaagaagcac cggctaactc | 600 |
| cgtgccagca gccgcggtaa tacgagggt gcaagcgtta atcggaatta ctgggcgtaa | 660 |
| agcgcacgca ggcggtttgt taagtcagat gtgaaatccc cgggctcaac ctgggaactg | 720 |
| catctgatac tggcaagctt gtcacacgta gaggggggta gaattccagg tgtagcggtg | 780 |
| aaatgcgtag agatctggag gaataccggt ggcgaaggcg gccccctgga cgaagactga | 840 |
| cgctcaggtg cgaaagcgtg gggagcaaac aggattagat accctggtag tccacgccgt | 900 |
| aaacgatgtc gacttggagg ttgtgccctt gaggcgtggc ttccggagct aacgcgttaa | 960 |
| gtcgaccgcc tggggagtac ggccgcaagg ttaaaactca aatgaattga cggggggcccg | 1020 |
| cacaagcggt ggagcatgtg gtttaattcg atgcaacgcg aagaaccta cctggtcttg | 1080 |
| acatccacga agttttcag agatgagaat gtgccttcgg gaaccgtgag acaggtgctg | 1140 |
| agatcggaag agcacacgtc tgaactccag tcacaatcag tctcgtatct cgtatgccgt | 1200 |

```
cttctgcttg ttgtcgactc tagggataac agggtaatga gtcgacaaca agcagaagac    1260
ggcatacgag attggtcaac gatagtctcg tgggctcgga gatgtgtata agagacagtc    1320
gttctaagag ggtgccagct gtctcttata cacatctgac gctgccgacg aatcaccagg    1380
tgtgtgtaga tctcggtggt cgccgtatca ttttgtcgac tc                       1422
```

<210> SEQ ID NO 12
<211> LENGTH: 1572
<212> TYPE: DNA
<213> ORGANISM: Artificial Sequence
<220> FEATURE:
<223> OTHER INFORMATION: synthetic

<400> SEQUENCE: 12

```
gagtcgacaa aatgatacgg cgaccaccga gatctacact ctttccctac acgacgctct     60
tccgatctcc caaacgtcgg aaaggtctaa attgaagagt ttgatcatgg ctcagattga    120
acgctggcgg caggcctaac acatgcaagt cgaacggtaa caggaagaag cttgctcttt    180
gctgacgagt ggcggacggg tgagtaatgt ctgggaaact gcctgatgga gggggataac    240
tactggaaac ggtagctaat accgcataac gtcgcaagac caaagagggg gaccttcggg    300
cctcttgcca tcggatgtgc ccagatggga ttagctagta ggtgggtaa cggctcacct    360 aggcgacgat ccctagctgg tctgagagga tgaccagcca cactggaact gagacacggt    420
ccacacacct acggaggca gcagtgggga atattgcaca atgggcgcaa gcctgatgca    480
gccatgccgc gtgtatgaag aaggccttcg ggttgtaaag tactttcagc ggggaggaag    540
ggagtaaagt taatacccttt gctcattgac gttacccgca gaagaagcac cggctaactc    600
cgtgccagca gccgcggtaa tacggagggt gcaagcgtta atcggaatta ctgggcgtaa    660
agcgcacgca ggcggttttgt taagtcagat gtgaaatccc cgggctcaac ctgggaactg    720
catctgatac tggcaagctt gtcacacgta gaggggggta gaattccagg tgtagcggtg    780
aaatgcgtag agatctggag gaataccggt ggcgaaggcg gccccctgga cgaagactga    840
cgctcaggtg cgaaagcgtg gggagcaaac aggattagat accctggtag tccacgccgt    900
aaacgatgtc gacttggagg ttgtgccctt gaggcgtggc ttccggagct aacgcgttaa    960
gtcgaccgcc tggggagtac ggccgcaagg ttaaaactca aatgaattga cggggcccgc   1020
cacaagcggt ggagcatgtg gtttaattcg atgcaacgcg aagaaccta cctggtcttg    1080 acatccacgg aagttttcag agatgagaat gtgccttcgg gaaccgtgag acaggtgctg    1140
catggctgtc gtcagctcgt gttgtgaaat gttgggttaa gtcccgcaac gagcgcaacc    1200
cttatccttt gttgccagcg gtccggccgg gaactcaaag gagactgcca gtgataaact    1260
ggaggaaggt ggggatgacg tcaagtcatc agatcggaag agcacacgtc tgaactccag    1320
tcacaatcag tctcgtatct cgtatgccgt cttctgcttg ttgtcgactc tagggataac    1380
agggtaatga gtcgacaaca agcagaagac ggcatacgag attggtcaac gatagtctcg    1440
tgggctcgga gatgtgtata agagacagtg caactcaacg gtcccaggct gtctcttata    1500
cacatctgac gctgccgacg aatcaccagg tgtgtgtaga tctcggtggt cgccgtatca    1560
ttttgtcgac tc                                                        1572
```

<210> SEQ ID NO 13
<211> LENGTH: 1722
<212> TYPE: DNA
<213> ORGANISM: Artificial Sequence
<220> FEATURE:

<223> OTHER INFORMATION: synthetic

<400> SEQUENCE: 13

```
gagtcgacaa aatgatacgg cgaccaccga gatctacact ctttccctac acgacgctct      60
tccgatctaa ccagaggatg agacacgtaa attgaagagt ttgatcatgg ctcagattga     120
acgctggcgg caggcctaac acatgcaagt cgaacggtaa caggaagaag cttgctcttt     180
gctgacgagt ggcggacggg tgagtaatgt ctgggaaact gcctgatgga ggggataac     240
tactggaaac ggtagctaat accgcataac gtcgcaagac caaagagggg gaccttcggg     300
cctcttgcca tcggatgtgc ccagatggga ttagctagta ggtggggtaa cggctcacct     360
aggcgacgat ccctagctgg tctgagagga tgaccagcca cactggaact gagacacggt     420
ccacacacct acggaggca gcagtgggga atattgcaca atgggcgcaa gcctgatgca     480
gccatgccgc gtgtatgaag aaggccttcg ggttgtaaag tactttcagc ggggaggaag     540
ggagtaaagt taatacctt gctcattgac gttacccgca gaagaagcac cggctaactc     600
cgtgccagca gccgcggtaa tacggagggt gcaagcgtta atcggaatta ctgggcgtaa     660
agcgcacgca ggcggtttgt taagtcagat gtgaaatccc cgggctcaac ctgggaactg     720
catctgatac tggcaagctt gtcacacgta gaggggggta gaattccagg tgtagcggtg     780
aaatgcgtag agatctggag gaataccggt ggcgaaggcg ccccctgga cgaagactga     840
cgctcaggtg cgaaagcgtg gggagcaaac aggattagat accctggtag tccacgccgt     900
aaacgatgtc gacttggagg ttgtgccctt gaggcgtggc ttccggagct aacgcgttaa     960
gtcgaccgcc tggggagtac ggccgcaagg ttaaaactca aatgaattga cggggggccc    1020
cacaagcggt ggagcatgtg gtttaattcg atgcaacgcg aagaaccta cctggtcttg    1080
acatccacga agttttcag agatgagaat gtgccttcgg gaaccgtgag acaggtgctg    1140
catggctgtc gtcagctcgt gttgtgaaat gttgggttaa gtcccgcaac gagcgcaacc    1200
cttatccttt gttgccagcg gtccggccgg gaactcaaag gagactgcca gtgataaact    1260
ggaggaaggt ggggatgacg tcaagtcatc atggccctta cgaccagggc tacacacgtg    1320
ctacaatggc gcatacaaag agaagcgacc tcgcgagagc aagcggacct cataaagtgc    1380
gtcgtagtcc ggattggtga ctgcaactcc acaccatgaa gtcggaatcg ctagtaatcg    1440
agatcggaag agcacacgtc tgaactccag tcacaatcag tctcgtatct cgtatgccgt    1500
cttctgcttg ttgtcgactc tagggataac agggtaatga gtcgacaaca agcagaagac    1560
ggcatacgag attggtcaac gatagtctcg tgggctcgga gatgtgtata agagacagtg    1620
gctccttctg ttaaggcact gtctcttata cacatctgac gctgccgacg aatcaccagg    1680
tgtgtgtaga tctcggtggt cgccgtatca ttttgtcgac tc                        1722
```

<210> SEQ ID NO 14
<211> LENGTH: 372
<212> TYPE: DNA
<213> ORGANISM: Artificial Sequence
<220> FEATURE:
<223> OTHER INFORMATION: synthetic

<400> SEQUENCE: 14

```
gagtcgacaa aatgatacgg cgaccaccga gatctacact ctttccctac acgacgctct      60
tccgatctcc acctaacaga cacttgttag agatcggaag agcacacgtc tgaactccag     120
tcacaatcag tctcgtatct cgtatgccgt cttctgcttg ttgtcgactc tagggataac     180
agggtaatga gtcgacaaca agcagaagac ggcatacgag attggtcaac gatagtctcg     240
```

```
tgggctcgga gatgtgtata agagacaggg taagtagtgc gtgagggtct gtctcttata    300
cacatctgac gctgccgacg aatcaccagg tgtgtgtaga tctcggtggt cgccgtatca    360
ttttgtcgac tc                                                        372
```

<210> SEQ ID NO 15
<211> LENGTH: 522
<212> TYPE: DNA
<213> ORGANISM: Artificial Sequence
<220> FEATURE:
<223> OTHER INFORMATION: synthetic

<400> SEQUENCE: 15

```
gagtcgacaa aatgatacgg cgaccaccga gatctacact ctttccctac acgacgctct     60
tccgatctgc gccctggcgc cggccaggtt tttaaggcgc ttatataatc aaaccctttg    120
taaaaattaa agttttaaat ggaattctaa tcgatttatt tcacattagc tttatttaag    180
tgtgacctac gcagaaagct agcgaaatac tcatcaaccc tccccgcca tcgcagcgcc     240 agatcggaag agcacacgtc tgaactccag tcacaatcag tctcgtatct cgtatgccgt    300
cttctgcttg ttgtcgactc tagggataac agggtaatga gtcgacaaca agcagaagac    360
ggcatacgag attggtcaac gatagtctcg tgggctcgga gatgtgtata agagacagac    420
ggagtagtac ggtcaaatct gtctcttata cacatctgac gctgccgacg aatcaccagg    480
tgtgtgtaga tctcggtggt cgccgtatca ttttgtcgac tc                       522
```

<210> SEQ ID NO 16
<211> LENGTH: 672
<212> TYPE: DNA
<213> ORGANISM: Artificial Sequence
<220> FEATURE:
<223> OTHER INFORMATION: synthetic

<400> SEQUENCE: 16

```
gagtcgacaa aatgatacgg cgaccaccga gatctacact ctttccctac acgacgctct     60
tccgatctct actaaacaat aatgggaatt tttaaggcgc ttatataatc aaacccttg    120 taaaaattaa agttttaaat ggaattctaa tcgatttatt tcacattagc tttatttaag    180
tgtgacctac gcagaaagct agcgaaatac tcatcaaccc tccccgcca tcgcagcgcc     240 attctcctaa tttgcgaaaa aagctccggg aaaaggaaaa agcggcagtc gtaatagcga    300
actgaaactg aacgagagta aaagtgaaaa gacagcagga actcagccat gtcgaagatc    360
ggaattaacg gatttggccg catcggccgc agatcggaag agcacacgtc tgaactccag    420
tcacaatcag tctcgtatct cgtatgccgt cttctgcttg ttgtcgactc tagggataac    480
agggtaatga gtcgacaaca agcagaagac ggcatacgag attggtcaac gatagtctcg    540
tgggctcgga gatgtgtata agagacaggg attgccacac gcgatagact gtctcttata    600
cacatctgac gctgccgacg aatcaccagg tgtgtgtaga tctcggtggt cgccgtatca    660
ttttgtcgac tc                                                        672
```

<210> SEQ ID NO 17
<211> LENGTH: 822
<212> TYPE: DNA
<213> ORGANISM: Artificial Sequence
<220> FEATURE:
<223> OTHER INFORMATION: synthetic

<400> SEQUENCE: 17

```
gagtcgacaa aatgatacgg cgaccaccga gatctacact ctttccctac acgacgctct      60
tccgatctct gtgttcggcc ttcgagattt tttaaggcgc ttatataatc aaaccctttg     120
taaaaattaa agttttaaat ggaattctaa tcgatttatt tcacattagc tttatttaag     180
tgtgacctac gcagaaagct agcgaaatac tcatcaaccc tccccgcca tcgcagcgcc      240
attctcctaa tttgcgaaaa aagctccggg aaaaggaaaa agcggcagtc gtaatagcga     300
actgaaactg aacgagagta aaagtgaaaa gacagcagga actcagccat gtcgaagatc     360
ggaattaacg gatttggccg catcggccgc ttggtgctcc gcgccgccat cgataagggc     420
gcctccgtgg tggccgtcaa cgatcccttc atcgatgtca actacatggt ttacctgttt     480
aaattccaca ccacacacgg tcgtttcaag ggcaccgttg cggctgaggg cggattcctg     540
agatcggaag agcacacgtc tgaactccag tcacaatcag tctcgtatct cgtatgccgt     600
cttctgcttg ttgtcgactc tagggataac agggtaatga gtcgacaaca agcagaagac     660
ggcatacgag attggtcaac gatagtctcg tgggctcgga gatgtgtata agagacagta     720
gtgtttaagt gcgaacctct gtctcttata cacatctgac gctgccgacg aatcaccagg     780
tgtgtgtaga tctcggtggt cgccgtatca ttttgtcgac tc                        822
```

<210> SEQ ID NO 18
<211> LENGTH: 972
<212> TYPE: DNA
<213> ORGANISM: Artificial Sequence
<220> FEATURE:
<223> OTHER INFORMATION: synthetic

<400> SEQUENCE: 18

```
gagtcgacaa aatgatacgg cgaccaccga gatctacact ctttccctac acgacgctct      60
tccgatctta tgaaatcgga gtatcagttt tttaaggcgc ttatataatc aaaccctttg     120
taaaaattaa agttttaaat ggaattctaa tcgatttatt tcacattagc tttatttaag     180
tgtgacctac gcagaaagct agcgaaatac tcatcaaccc tccccgcca tcgcagcgcc      240
attctcctaa tttgcgaaaa aagctccggg aaaaggaaaa agcggcagtc gtaatagcga     300
actgaaactg aacgagagta aaagtgaaaa gacagcagga actcagccat gtcgaagatc     360
ggaattaacg gatttggccg catcggccgc ttggtgctcc gcgccgccat cgataagggc     420
gcctccgtgg tggccgtcaa cgatcccttc atcgatgtca actacatggt ttacctgttt     480
aaattccaca ccacacacgg tcgtttcaag ggcaccgttg cggctgaggg cggattcctg     540
gtggtgaacg gccagaagat caccgtgttc agcgagcgcg acccggccaa catcaactgg     600
gccagtgctg gagccgagta tgtggtggtg accaccggag tgttcaccac cattgacaag     660
gcgtccaccc acttgaaggg cggcgccaag agatcggaag agcacacgtc tgaactccag     720
tcacaatcag tctcgtatct cgtatgccgt cttctgcttg ttgtcgactc tagggataac     780
agggtaatga gtcgacaaca agcagaagac ggcatacgag attggtcaac gatagtctcg     840
tgggctcgga gatgtgtata agagacagaa gagccctgcc tcaagtccct gtctcttata     900
cacatctgac gctgccgacg aatcaccagg tgtgtgtaga tctcggtggt cgccgtatca     960
ttttgtcgac tc                                                         972
```

<210> SEQ ID NO 19
<211> LENGTH: 1122
<212> TYPE: DNA

<213> ORGANISM: Artificial Sequence
<220> FEATURE:
<223> OTHER INFORMATION: synthetic

<400> SEQUENCE: 19

```
gagtcgacaa aatgatacgg cgaccaccga gatctacact ctttccctac acgacgctct    60
tccgatctag ccaaacgtct gaacagattt tttaaggcgc ttatataatc aaaccctttg   120
taaaaattaa agttttaaat ggaattctaa tcgatttatt tcacattagc tttatttaag   180
tgtgacctac gcagaaagct agcgaaatac tcatcaaccc tccccgcca tcgcagcgcc    240
attctcctaa tttgcgaaaa aagctccggg aaaaggaaaa agcggcagtc gtaatagcga   300
actgaaactg aacgagagta aaagtgaaaa gacagcagga actcagccat gtcgaagatc   360
ggaattaacg gatttggccg catcggccgc ttggtgctcc gcgccgccat cgataagggc   420
gcctccgtgg tggccgtcaa cgatcccttc atcgatgtca actacatggt ttacctgttt   480
aaattccaca ccacacacgg tcgtttcaag ggcaccgttg cggctgaggg cggattcctg   540
gtggtgaacg gccagaagat caccgtgttc agcgagcgcg acccggccaa catcaactgg   600
gccagtgctg gagccgagta tgtggtggtg accaccggag tgttcaccac cattgacaag   660
gcgtccaccc acttgaaggg cggcgccaag aaggtcatca tctcggcccc atccgccgat   720
gcgcccatgt tcgtgtgcgg cgttaacctg gacgcctaca gccccgacat gaaggtggtc   780
tccaacgcct cgtgcaccac caactgcctg gctcccctgg ccaaggtcat caatgacaac   840
agatcggaag agcacacgtc tgaactccag tcacaatcag tctcgtatct cgtatgccgt   900
cttctgcttg ttgtcgactc tagggataac agggtaatga gtcgacaaca agcagaagac   960
ggcatacgag attggtcaac gatagtctcg tgggctcgga gatgtgtata agagacagcc  1020
gtgtcgaacg ccactcgact gtctcttata cacatctgac gctgccgacg aatcaccagg  1080
tgtgtgtaga tctcggtggt cgccgtatca ttttgtcgac tc                     1122
```

<210> SEQ ID NO 20
<211> LENGTH: 1272
<212> TYPE: DNA
<213> ORGANISM: Artificial Sequence
<220> FEATURE:
<223> OTHER INFORMATION: synthetic

<400> SEQUENCE: 20

```
gagtcgacaa aatgatacgg cgaccaccga gatctacact ctttccctac acgacgctct    60
tccgatctca gtccagggc actcgccttt tttaaggcgc ttatataatc aaaccctttg    120
taaaaattaa agttttaaat ggaattctaa tcgatttatt tcacattagc tttatttaag   180
tgtgacctac gcagaaagct agcgaaatac tcatcaaccc tccccgcca tcgcagcgcc    240
attctcctaa tttgcgaaaa aagctccggg aaaaggaaaa agcggcagtc gtaatagcga   300
actgaaactg aacgagagta aaagtgaaaa gacagcagga actcagccat gtcgaagatc   360
ggaattaacg gatttggccg catcggccgc ttggtgctcc gcgccgccat cgataagggc   420
gcctccgtgg tggccgtcaa cgatcccttc atcgatgtca actacatggt ttacctgttt   480
aaattccaca ccacacacgg tcgtttcaag ggcaccgttg cggctgaggg cggattcctg   540
gtggtgaacg gccagaagat caccgtgttc agcgagcgcg acccggccaa catcaactgg   600
gccagtgctg gagccgagta tgtggtggtg accaccggag tgttcaccac cattgacaag   660
gcgtccaccc acttgaaggg cggcgccaag aaggtcatca tctcggcccc atccgccgat   720
gcgcccatgt tcgtgtgcgg cgttaacctg gacgcctaca gccccgacat gaaggtggtc   780
```

```
tccaacgcct cgtgcaccac caactgcctg gctcccctgg ccaaggtcat caatgacaac      840
ttcgagatcg tcgagggtct gatgaccacc gtgcacgcca ccactgccac ccagaagacc      900
gtcgacggtc cctctggcaa actgtggcgc gatggacgtg gcgccgccca gaacatcatc      960
ccggccgcca ccggagccgc caaggctgtg agatcggaag agcacacgtc tgaactccag     1020
tcacaatcag tctcgtatct cgtatgccgt cttctgcttg ttgtcgactc tagggataac     1080
agggtaatga gtcgacaaca agcagaagac ggcatacgag attggtcaac gatagtctcg     1140
tgggctcgga gatgtgtata agagacagta tgccatgggc tttcgaacct gtctcttata     1200
cacatctgac gctgccgacg aatcaccagg tgtgtgtaga tctcggtggt cgccgtatca     1260
ttttgtcgac tc                                                         1272

<210> SEQ ID NO 21
<211> LENGTH: 1422
<212> TYPE: DNA
<213> ORGANISM: Artificial Sequence
<220> FEATURE:
<223> OTHER INFORMATION: synthetic

<400> SEQUENCE: 21
gagtcgacaa aatgatacgg cgaccaccga gatctacact ctttccctac acgacgctct       60
tccgatctat ttctactcat aggttcattt tttaaggcgc ttatataatc aaacccttig      120 taaaaattaa agttttaaat ggaattctaa tcgatttatt tcacattagc tttatttaag      180
tgtgacctac gcagaaagct agcgaaatac tcatcaaccc tccccgcca tcgcagcgcc      240 attctcctaa tttgcgaaaa aagctccggg aaaaggaaaa agcggcagtc gtaatagcga      300
actgaaactg aacgagagta aaagtgaaaa gacagcagga actcagccat gtcgaagatc      360
ggaattaacg gatttggccg catcggccgc ttggtgctcc gcgccgccat cgataagggc      420
gcctccgtgg tggccgtcaa cgatcccttc atcgatgtca actacatggt ttacctgttt      480
aaattccaca ccacacacgg tcgtttcaag ggcaccgttg cggctgaggg cggattcctg      540
gtggtgaacg ccagaagat caccgtgttc agcgagcgcg acccggccaa catcaactgg      600
gccagtgctg gagccgagta tgtggtggtg accaccggag tgttcaccac cattgacaag      660
gcgtccaccc acttgaaggg cggcgccaag aaggtcatca tctcggcccc atccgccgat      720
gcgcccatgt tcgtgtgcgg cgttaacctg gacgcctaca gccccgacat gaaggtggtc      780
tccaacgcct cgtgcaccac caactgcctg gctcccctgg ccaaggtcat caatgacaac      840
ttcgagatcg tcgagggtct gatgaccacc gtgcacgcca ccactgccac ccagaagacc      900
gtcgacggtc cctctggcaa actgtggcgc gatggacgtg gcgccgccca gaacatcatc      960
ccggccgcca ccggagccgc caaggctgtg ggcaaggtca tccccgccct gaacggcaag     1020
ctgaccggca tggctttccg cgtgcccacg cccaatgtct ccgttgtgga tcttaccgtc     1080
cgcttgggca agggagccac ctatgacgaa atcaaggcta aggtcgagga ggcctccaag     1140
agatcggaag agcacacgtc tgaactccag tcacaatcag tctcgtatct cgtatgccgt     1200
cttctgcttg ttgtcgactc tagggataac agggtaatga gtcgacaaca agcagaagac     1260
ggcatacgag attggtcaac gatagtctcg tgggctcgga gatgtgtata agagacagtt     1320
agatcagata gaaggtacct gtctcttata cacatctgac gctgccgacg aatcaccagg     1380
tgtgtgtaga tctcggtggt cgccgtatca ttttgtcgac tc                        1422

<210> SEQ ID NO 22
```

<211> LENGTH: 1572
<212> TYPE: DNA
<213> ORGANISM: Artificial Sequence
<220> FEATURE:
<223> OTHER INFORMATION: synthetic

<400> SEQUENCE: 22

| | | | | | |
|---|---|---|---|---|---|
| gagtcgacaa | aatgatacgg | cgaccaccga | gatctacact | ctttccctac | acgacgctct | 60 |
| tccgatcttt | aagactgtta | gttcgaggtt | tttaaggcgc | ttatataatc | aaacccttg | 120 |
| taaaaattaa | agttttaaat | ggaattctaa | tcgatttatt | tcacattagc | tttatttaag | 180 |
| tgtgacctac | gcagaaagct | agcgaaatac | tcatcaaccc | tccccgcca | tcgcagcgcc | 240 |
| attctcctaa | tttgcgaaaa | aagctccggg | aaaaggaaaa | agcggcagtc | gtaatagcga | 300 |
| actgaaactg | aacgagagta | aaagtgaaaa | gacagcagga | actcagccat | gtcgaagatc | 360 |
| ggaattaacg | gatttggccg | catcggccgc | ttggtgctcc | gcgccgccat | cgataagggc | 420 |
| gcctccgtgg | tggccgtcaa | cgatcccttc | atcgatgtca | actacatggt | ttacctgttt | 480 |
| aaattccaca | ccacacacgg | tcgtttcaag | ggcaccgttg | cggctgaggg | cggattcctg | 540 |
| gtggtgaacg | gccagaagat | caccgtgttc | agcgagcgcg | acccggccaa | catcaactgg | 600 |
| gccagtgctg | gagccgagta | tgtggtggtg | accaccggag | tgttcaccac | cattgacaag | 660 |
| gcgtccaccc | acttgaaggg | cggcgccaag | aaggtcatca | tctcggcccc | atccgccgat | 720 |
| gcgcccatgt | tcgtgtgcgg | cgttaacctg | gacgcctaca | gccccgacat | gaaggtggtc | 780 |
| tccaacgcct | cgtgcaccac | caactgcctg | gctcccctgg | ccaaggtcat | caatgacaac | 840 |
| ttcgagatcg | tcgagggtct | gatgaccacc | gtgcacgcca | ccactgccac | ccagaagacc | 900 |
| gtcgacggtc | cctctggcaa | actgtggcgc | gatggacgtg | gcgccgccca | gaacatcatc | 960 |
| ccggccgcca | ccgagccgc | caaggctgtg | ggcaaggtca | tccccgccct | gaacggcaag | 1020 |
| ctgaccggca | tggctttccg | cgtgcccacg | cccaatgtct | ccgttgtgga | tcttaccgtc | 1080 |
| cgcttgggca | agggagccac | ctatgacgaa | atcaaggcta | aggtcgagga | ggcctccaag | 1140 |
| ggaccctga | agggaatcct | gggctacacc | gatgaggagg | tggtctccac | cgacttcttc | 1200 |
| agcgacaccc | attcgtctgt | gttcgacgcc | aaggctggca | tttcgctgaa | cgataagttc | 1260 |
| gtcaagctaa | tctcgtggta | cgacaacgag | agatcggaag | agcacacgtc | tgaactccag | 1320 |
| tcacaatcag | tctcgtatct | cgtatgccgt | cttctgcttg | ttgtcgactc | tagggataac | 1380 |
| agggtaatga | gtcgacaaca | agcagaagac | ggcatacgag | attggtcaac | gatagtctcg | 1440 |
| tgggctcgga | gatgtgtata | agagacagtt | tatattgttc | tgcctcacct | gtctcttata | 1500 |
| cacatctgac | gctgccgacg | aatcaccagg | tgtgtgtaga | tctcggtggt | cgccgtatca | 1560 |
| ttttgtcgac | tc | | | | | 1572 |

<210> SEQ ID NO 23
<211> LENGTH: 1722
<212> TYPE: DNA
<213> ORGANISM: Artificial Sequence
<220> FEATURE:
<223> OTHER INFORMATION: synthetic

<400> SEQUENCE: 23

| | | | | | |
|---|---|---|---|---|---|
| gagtcgacaa | aatgatacgg | cgaccaccga | gatctacact | ctttccctac | acgacgctct | 60 |
| tccgatctag | ttactggctt | tgtaggattt | tttaaggcgc | ttatataatc | aaacccttg | 120 |
| taaaaattaa | agttttaaat | ggaattctaa | tcgatttatt | tcacattagc | tttatttaag | 180 |
| tgtgacctac | gcagaaagct | agcgaaatac | tcatcaaccc | tccccgcca | tcgcagcgcc | 240 |

```
attctcctaa tttgcgaaaa aagctccggg aaaaggaaaa agcggcagtc gtaatagcga      300
actgaaactg aacgagagta aaagtgaaaa gacagcagga actcagccat gtcgaagatc      360
ggaattaacg gatttggccg catcggccgc ttggtgctcc gcgccgccat cgataagggc      420
gcctccgtgg tggccgtcaa cgatcccttc atcgatgtca actacatggt ttacctgttt      480
aaattccaca ccacacacgg tcgtttcaag ggcaccgttg cggctgaggg cggattcctg      540
gtggtgaacg gccagaagat caccgtgttc agcgagcgcg acccggccaa catcaactgg      600
gccagtgctg gagccgagta tgtggtggtg accaccggag tgttcaccac cattgacaag      660
gcgtccaccc acttgaaggg cggcgccaag aaggtcatca tctcggcccc atccgccgat      720
gcgcccatgt tcgtgtgcgg cgttaacctg gacgcctaca gccccgacat gaaggtggtc      780
tccaacgcct cgtgcaccac caactgcctg gctcccctgg ccaaggtcat caatgacaac      840
ttcgagatcg tcgagggtct gatgaccacc gtgcacgcca ccactgccac ccagaagacc      900
gtcgacggtc cctctggcaa actgtggcgc gatggacgtg gcgccgccca gaacatcatc      960
ccggccgcca ccggagccgc caaggctgtg ggcaaggtca tccccgccct gaacggcaag     1020
ctgaccggca tggcttttccg cgtgcccacg cccaatgtct ccgttgtgga tcttaccgtc     1080
cgcttgggca agggagccac ctatgacgaa atcaaggcta aggtcgagga ggcctccaag     1140 ggaccccctga agggaatcct gggctacacc gatgaggagg tggtctccac cgacttcttc     1200
agcgacaccc attcgtctgt gttcgacgcc aaggctggca tttcgctgaa cgataagttc     1260
gtcaagctaa tctcgtggta cgacaacgag ttcggttact ccaaccgcgt catcgacctg     1320
atcaagtata tgcagagcaa ggactaaact agccaaaact atcgtacaaa cccggcgccc     1380
agcagctggt cgggaatcac tgttgcataa tccgcaaggg gcgcaattga ggatgctttt     1440
agatcggaag agcacacgtc tgaactccag tcacaatcag tctcgtatct cgtatgccgt     1500
cttctgcttg ttgtcgactc tagggataac agggtaatga gtcgacaaca agcagaagac     1560
ggcatacgag attggtcaac gatagtctcg tgggctcgga gatgtgtata agagacagtg     1620
tggctccaat tgctgcaact gtctcttata cacatctgac gctgccgacg aatcaccagg     1680
tgtgtgtaga tctcggtggt cgccgtatca ttttgtcgac tc                        1722
```

<210> SEQ ID NO 24
<211> LENGTH: 372
<212> TYPE: DNA
<213> ORGANISM: Artificial Sequence
<220> FEATURE:
<223> OTHER INFORMATION: synthetic

<400> SEQUENCE: 24

```
gagtcgacaa aatgatacgg cgaccaccga gatctacact ctttccctac acgacgctct       60
tccgatctaa cggttgatgg gcctggtatc agatcggaag agcacacgtc tgaactccag      120
tcacaatcag tctcgtatct cgtatgccgt cttctgcttg ttgtcgactc tagggataac      180
agggtaatga gtcgacaaca agcagaagac ggcatacgag attggtcaac gatagtctcg      240
tgggctcgga gatgtgtata agagacagca cgcgtacgtg ctatcttcct gtctcttata      300
cacatctgac gctgccgacg aatcaccagg tgtgtgtaga tctcggtggt cgccgtatca      360
ttttgtcgac tc                                                         372
```

<210> SEQ ID NO 25
<211> LENGTH: 522
<212> TYPE: DNA

<213> ORGANISM: Artificial Sequence
<220> FEATURE:
<223> OTHER INFORMATION: synthetic

<400> SEQUENCE: 25

```
gagtcgacaa aatgatacgg cgaccaccga gatctacact ctttccctac acgacgctct    60
tccgatctcg ttgtgtttgc tggcgcaatc atattcgttt tacgtttgtc aagcctcata   120
gccggcagtt cgaacgtata cgctctctgt gacagacctc gaaatcgtag ctctacacaa   180
ttctgtgaat tttccttgtc gcgtgtgaaa cacttccaat aaaaactcaa tatgcgtgaa   240
agatcggaag agcacacgtc tgaactccag tcacaatcag tctcgtatct cgtatgccgt   300
cttctgcttg ttgtcgactc tagggataac agggtaatga gtcgacaaca agcagaagac   360
ggcatacgag attggtcaac gatagtctcg tgggctcgga gatgtgtata agagacagtc   420
gcgaccaaat ggtcagtcct gtctcttata cacatctgac gctgccgacg aatcaccagg   480
tgtgtgtaga tctcggtggt cgccgtatca ttttgtcgac tc                      522
```

<210> SEQ ID NO 26
<211> LENGTH: 672
<212> TYPE: DNA
<213> ORGANISM: Artificial Sequence
<220> FEATURE:
<223> OTHER INFORMATION: synthetic

<400> SEQUENCE: 26

```
gagtcgacaa aatgatacgg cgaccaccga gatctacact ctttccctac acgacgctct    60
tccgatctgg ctgacggttg agagggattc atattcgttt tacgtttgtc aagcctcata   120
gccggcagtt cgaacgtata cgctctctgt gacagacctc gaaatcgtag ctctacacaa   180
ttctgtgaat tttccttgtc gcgtgtgaaa cacttccaat aaaaactcaa tatgcgtgaa   240
tgtatctcta tccatgttgg tcaggctggt gtccagattg gaaacgcctg ctgggagctc   300
tactgcttgg agcacggcat ccagcccgat ggccagatgc cgtctgacaa gaccgtgggc   360
ggaggtgatc acacgttcaa caccttcttc agatcggaag agcacacgtc tgaactccag   420
tcacaatcag tctcgtatct cgtatgccgt cttctgcttg ttgtcgactc tagggataac   480
agggtaatga gtcgacaaca agcagaagac ggcatacgag attggtcaac gatagtctcg   540
tgggctcgga gatgtgtata agagacagtt cggcaatcag aaagggtact gtctcttata   600
cacatctgac gctgccgacg aatcaccagg tgtgtgtaga tctcggtggt cgccgtatca   660
ttttgtcgac tc                                                       672
```

<210> SEQ ID NO 27
<211> LENGTH: 822
<212> TYPE: DNA
<213> ORGANISM: Artificial Sequence
<220> FEATURE:
<223> OTHER INFORMATION: synthetic

<400> SEQUENCE: 27

```
gagtcgacaa aatgatacgg cgaccaccga gatctacact ctttccctac acgacgctct    60
tccgatcttt cacatcgcct tgaccttatc atattcgttt tacgtttgtc aagcctcata   120
gccggcagtt cgaacgtata cgctctctgt gacagacctc gaaatcgtag ctctacacaa   180
ttctgtgaat tttccttgtc gcgtgtgaaa cacttccaat aaaaactcaa tatgcgtgaa   240
tgtatctcta tccatgttgg tcaggctggt gtccagattg gaaacgcctg ctgggagctc   300
tactgcttgg agcacggcat ccagcccgat ggccagatgc cgtctgacaa gaccgtgggc   360
```

```
ggaggtgatc acacgttcaa caccttcttc agcgagactg gagctggcaa gcacgtgccc      420
cgcgccgtgt ttgtggatct ggaacccact gtggtcgatg aggtccgtac cggaacctac      480
cgtcagctgt tccaccccga gcagctgatc actggtaagg aggatgcggc caacaactac      540
agatcggaag agcacgtc tgaactccag tcacaatcag tctcgtatct cgtatgccgt       600
cttctgcttg ttgtcgactc tagggataac agggtaatga gtcgacaaca agcagaagac      660
ggcatacgag attggtcaac gatagtctcg tgggctcgga gatgtgtata agagacagtt      720
aggaccggat taggttcact gtctcttata cacatctgac gctgccgacg aatcaccagg      780
tgtgtgtaga tctcggtggt cgccgtatca ttttgtcgac tc                         822

<210> SEQ ID NO 28
<211> LENGTH: 972
<212> TYPE: DNA
<213> ORGANISM: Artificial Sequence
<220> FEATURE:
<223> OTHER INFORMATION: synthetic

<400> SEQUENCE: 28
gagtcgacaa aatgatacgg cgaccaccga gatctacact ctttccctac acgacgctct       60
tccgatcttg gtactgcctc ctggcctctc atattcgttt tacgtttgtc aagcctcata      120
gccggcagtt cgaacgtata cgctctctgt gacagacctc gaaatcgtag ctctacacaa      180
ttctgtgaat tttccttgtc gcgtgtgaaa cacttccaat aaaaactcaa tatgcgtgaa      240
tgtatctcta tccatgttgg tcaggctggt gtccagattg gaaacgcctg ctgggagctc      300
tactgcttgg agcacggcat ccagcccgat ggccagatgc cgtctgacaa gaccgtgggc      360
ggaggtgatc acacgttcaa caccttcttc agcgagactg gagctggcaa gcacgtgccc      420
cgcgccgtgt ttgtggatct ggaacccact gtggtcgatg aggtccgtac cggaacctac      480
cgtcagctgt tccaccccga gcagctgatc actggtaagg aggatgcggc caacaactac      540
gcccgtggcc actacaccat cggcaaggag atcgtcgatc tggttctgga caggatccgc      600
aagctggccg atcagtgcac cggtctgcag ggcttcctca tcttccactc gttcggtgga      660
ggtaccggct ccgcttcac ctcgctgctg agatcggaag agcacgtc tgaactccag       720 tcacaatcag tctcgtatct cgtatgccgt cttctgcttg ttgtcgactc tagggataac      780
agggtaatga gtcgacaaca agcagaagac ggcatacgag attggtcaac gatagtctcg      840
tgggctcgga gatgtgtata agagacagag acctcggacg aggctcacct gtctcttata      900
cacatctgac gctgccgacg aatcaccagg tgtgtgtaga tctcggtggt cgccgtatca      960
ttttgtcgac tc                                                         972

<210> SEQ ID NO 29
<211> LENGTH: 1122
<212> TYPE: DNA
<213> ORGANISM: Artificial Sequence
<220> FEATURE:
<223> OTHER INFORMATION: synthetic

<400> SEQUENCE: 29
gagtcgacaa aatgatacgg cgaccaccga gatctacact ctttccctac acgacgctct       60
tccgatctcg accgtcattg acggccctc atattcgttt tacgtttgtc aagcctcata      120
gccggcagtt cgaacgtata cgctctctgt gacagacctc gaaatcgtag ctctacacaa      180
ttctgtgaat tttccttgtc gcgtgtgaaa cacttccaat aaaaactcaa tatgcgtgaa      240
```

```
tgtatctcta tccatgttgg tcaggctggt gtccagattg gaaacgcctg ctgggagctc      300
tactgcttgg agcacggcat ccagcccgat ggccagatgc cgtctgacaa gaccgtgggc      360
ggaggtgatc acacgttcaa caccttcttc agcgagactg gagctggcaa gcacgtgccc      420
cgcgccgtgt ttgtggatct ggaacccact gtggtcgatg aggtccgtac cggaacctac      480
cgtcagctgt tccaccccga gcagctgatc actggtaagg aggatgcggc caacaactac      540
gcccgtggcc actacaccat cggcaaggag atcgtcgatc tggttctgga caggatccgc      600
aagctggccg atcagtgcac cggtctgcag ggcttcctca tcttccactc gttcggtgga      660
ggtaccggct ccggcttcac ctcgctgctg atggagcgtc tctccgtgga ctacggcaag      720
aagtccaagc tggagttcgc catctaccca gccccccagg tgtccactgc cgtggtcgag      780
ccctacaact ccatcctgac cacccacacc accctggagc attccgactg cgccttcatg      840
agatcggaag agcacacgtc tgaactccag tcacaatcag tctcgtatct cgtatgccgt      900
cttctgcttg ttgtcgactc tagggataac agggtaatga gtcgacaaca agcagaagac      960
ggcatacgag attggtcaac gatagtctcg tgggctcgga gatgtgtata agagacagac     1020
ctgaaataca cagtaaccct gtctcttata cacatctgac gctgccgacg aatcaccagg     1080
tgtgtgtaga tctcggtggt cgccgtatca ttttgtcgac tc                        1122

<210> SEQ ID NO 30
<211> LENGTH: 1272
<212> TYPE: DNA
<213> ORGANISM: Artificial Sequence
<220> FEATURE:
<223> OTHER INFORMATION: synthetic

<400> SEQUENCE: 30
gagtcgacaa aatgatacgg cgaccaccga gatctacact ctttccctac acgacgctct       60
tccgatctta tcaccaggga tgcattgatc atattcgttt tacgtttgtc aagcctcata      120
gccggcagtt cgaacgtata cgctctctgt gacagacctc gaaatcgtag ctctacacaa      180
ttctgtgaat tttccttgtc gcgtgtgaaa cacttccaat aaaaactcaa tatgcgtgaa      240
tgtatctcta tccatgttgg tcaggctggt gtccagattg gaaacgcctg ctgggagctc      300
tactgcttgg agcacggcat ccagcccgat ggccagatgc cgtctgacaa gaccgtgggc      360
ggaggtgatc acacgttcaa caccttcttc agcgagactg gagctggcaa gcacgtgccc      420
cgcgccgtgt ttgtggatct ggaacccact gtggtcgatg aggtccgtac cggaacctac      480
cgtcagctgt tccaccccga gcagctgatc actggtaagg aggatgcggc caacaactac      540
gcccgtggcc actacaccat cggcaaggag atcgtcgatc tggttctgga caggatccgc      600
aagctggccg atcagtgcac cggtctgcag ggcttcctca tcttccactc gttcggtgga      660
ggtaccggct ccggcttcac ctcgctgctg atggagcgtc tctccgtgga ctacggcaag      720
aagtccaagc tggagttcgc catctaccca gccccccagg tgtccactgc cgtggtcgag      780
ccctacaact ccatcctgac cacccacacc accctggagc attccgactg cgccttcatg      840
gtcgacaacg aggctatcta cgacatctgc cgccgcaatc tggacattga gcgccccacg      900
tacaccaacc tgaaccgtct gattggccag atcgtgtcct cgattaccgc ctctctgcga      960
ttcgatggtg cccttaacgt ggatctgact agatcggaag agcacacgtc tgaactccag     1020
tcacaatcag tctcgtatct cgtatgccgt cttctgcttg ttgtcgactc tagggataac     1080
agggtaatga gtcgacaaca agcagaagac ggcatacgag attggtcaac gatagtctcg     1140
tgggctcgga gatgtgtata agagacagta ttgtgtaaga cattaccgct gtctcttata     1200
```

| | |
|---|---|
| cacatctgac gctgccgacg aatcaccagg tgtgtgtaga tctcggtggt cgccgtatca | 1260 |
| ttttgtcgac tc | 1272 |

<210> SEQ ID NO 31
<211> LENGTH: 1422
<212> TYPE: DNA
<213> ORGANISM: Artificial Sequence
<220> FEATURE:
<223> OTHER INFORMATION: synthetic

<400> SEQUENCE: 31

| | |
|---|---|
| gagtcgacaa aatgatacgg cgaccaccga gatctacact ctttccctac acgacgctct | 60 |
| tccgatctgg accatattta gttatcagtc atattcgttt tacgtttgtc aagcctcata | 120 |
| gccggcagtt cgaacgtata cgctctctgt gacagacctc gaaatcgtag ctctacacaa | 180 |
| ttctgtgaat tttccttgtc gcgtgtgaaa cacttccaat aaaaactcaa tatgcgtgaa | 240 |
| tgtatctcta tccatgttgg tcaggctggt gtccagattg gaaacgcctg ctgggagctc | 300 |
| tactgcttgg agcacggcat ccagcccgat ggccagatgc cgtctgacaa gaccgtgggc | 360 |
| ggaggtgatc acacgttcaa caccttcttc agcgagactg gagctggcaa gcacgtgccc | 420 |
| cgcgccgtgt ttgtggatct ggaacccact gtggtcgatg aggtccgtac cggaacctac | 480 |
| cgtcagctgt tccaccccga gcagctgatc actggtaagg aggatgcggc caacaactac | 540 |
| gcccgtggcc actacaccat cggcaaggag atcgtcgatc tggttctgga caggatccgc | 600 |
| aagctggccg atcagtgcac cggtctgcag ggcttcctca tcttccactc gttcggtgga | 660 |
| ggtaccggct ccggcttcac ctcgctgctg atggagcgtc tctccgtgga ctacggcaag | 720 |
| aagtccaagc tggagttcgc catctaccca gcccccagg tgtccactgc cgtggtcgag | 780 |
| ccctacaact ccatcctgac cacccacacc accctggagc attccgactg cgccttcatg | 840 |
| gtcgacaacg aggctatcta cgacatctgc cgccgcaatc tggacattga gcgcccacg | 900 |
| tacaccaacc tgaaccgtct gattggccag atcgtgtcct cgattaccgc ctctctgcga | 960 |
| ttcgatggtg cccttaacgt ggatctgact gagttccaga ccaacttggt gcccactacccca | 1020 |
| cgtattcact tcctctggt gacctacgcc cccgttatct ccgccgagaa ggcctaccac | 1080 |
| gagcagctgt cggtggctga tcaccaaac gcctgcttcg agccggccaa ccagatggtc | 1140 |
| agatcggaag agcacgtc tgaactccag tcacaatcag tctcgtatct cgtatgccgt | 1200 |
| cttctgcttg ttgtcgactc tagggataac agggtaatga gtcgacaaca agcagaagac | 1260 |
| ggcatacgag attggtcaac gatagtctcg tgggctcgga gatgtgtata agagacagtg | 1320 |
| gaggtattgc taataatgct gtctcttata cacatctgac gctgccgacg aatcaccagg | 1380 |
| tgtgtgtaga tctcggtggt cgccgtatca ttttgtcgac tc | 1422 |

<210> SEQ ID NO 32
<211> LENGTH: 1572
<212> TYPE: DNA
<213> ORGANISM: Artificial Sequence
<220> FEATURE:
<223> OTHER INFORMATION: synthetic

<400> SEQUENCE: 32

| | |
|---|---|
| gagtcgacaa aatgatacgg cgaccaccga gatctacact ctttccctac acgacgctct | 60 |
| tccgatctcg atttctaggt gttacttgtc atattcgttt tacgtttgtc aagcctcata | 120 |
| gccggcagtt cgaacgtata cgctctctgt gacagacctc gaaatcgtag ctctacacaa | 180 |

| | |
|---|---:|
| ttctgtgaat tttccttgtc gcgtgtgaaa cacttccaat aaaaactcaa tatgcgtgaa | 240 |
| tgtatctcta tccatgttgg tcaggctggt gtccagattg gaaacgcctg ctgggagctc | 300 |
| tactgcttgg agcacggcat ccagcccgat ggccagatgc cgtctgacaa gaccgtgggc | 360 |
| ggaggtgatc acacgttcaa caccttcttc agcgagactg gagctggcaa gcacgtgccc | 420 |
| cgcgccgtgt ttgtggatct ggaacccact gtggtcgatg aggtccgtac cggaacctac | 480 |
| cgtcagctgt tccaccccga gcagctgatc actggtaagg aggatgcggc caacaactac | 540 |
| gcccgtggcc actacaccat cggcaaggag atcgtcgatc tggttctgga caggatccgc | 600 |
| aagctggccg atcagtgcac cggtctgcag ggcttcctca tcttccactc gttcggtgga | 660 |
| ggtaccggct ccggcttcac ctcgctgctg atggagcgtc tctccgtgga ctacggcaag | 720 |
| aagtccaagc tggagttcgc catctaccca gcccccagg tgtccactgc cgtggtcgag | 780 |
| ccctacaact ccatcctgac cacccacacc accctggagc attccgactg cgccttcatg | 840 |
| gtcgacaacg aggctatcta cgacatctgc cgccgcaatc tggacattga gcgcccacg | 900 |
| tacaccaacc tgaaccgtct gattggccag atcgtgtcct cgattaccgc ctctctgcga | 960 |
| ttcgatggtg cccttaacgt ggatctgact gagttccaga ccaacttggt gccctaccca | 1020 |
| cgtattcact cccctctggt gacctacgcc cccgttatct ccgccgagaa ggcctaccac | 1080 |
| gagcagctgt cggtggctga gatcaccaac gcctgcttcg agccggccaa ccagatggtc | 1140 |
| aagtgcgatc cccgtcacgg caagtacatg gcctgctgca tgctgtaccg cggtgatgtt | 1200 |
| gtgcccaagg acgtcaacgc cgctattgcc accatcaaga ccaagcgcac cattcaattc | 1260 |
| gtcgactggt gccccactgg cttcaaggtt agatcggaag agcacacgtc tgaactccag | 1320 |
| tcacaatcag tctcgtatct cgtatgccgt cttctgcttg ttgtcgactc tagggataac | 1380 |
| agggtaatga gtcgacaaca gcagaagac ggcatacgag attggtcaac gatagtctcg | 1440 |
| tgggctcgga gatgtgtata agagacagcc tgcgtgtgcc gtgtaggact gtctcttata | 1500 |
| cacatctgac gctgccgacg aatcaccagg tgtgtgtaga tctcggtggt cgccgtatca | 1560 |
| ttttgtcgac tc | 1572 |

<210> SEQ ID NO 33
<211> LENGTH: 1722
<212> TYPE: DNA
<213> ORGANISM: Artificial Sequence
<220> FEATURE:
<223> OTHER INFORMATION: synthetic

<400> SEQUENCE: 33

| | |
|---|---:|
| gagtcgacaa aatgatacgg cgaccaccga gatctacact ctttccctac acgacgctct | 60 |
| tccgatcttt tgagggtcgc tacagaattc atattcgttt tacgtttgtc aagcctcata | 120 |
| gccggcagtt cgaacgtata cgctctctgt gacagacctc gaaatcgtag ctctacacaa | 180 |
| ttctgtgaat tttccttgtc gcgtgtgaaa cacttccaat aaaaactcaa tatgcgtgaa | 240 |
| tgtatctcta tccatgttgg tcaggctggt gtccagattg gaaacgcctg ctgggagctc | 300 |
| tactgcttgg agcacggcat ccagcccgat ggccagatgc cgtctgacaa gaccgtgggc | 360 |
| ggaggtgatc acacgttcaa caccttcttc agcgagactg gagctggcaa gcacgtgccc | 420 |
| cgcgccgtgt ttgtggatct ggaacccact gtggtcgatg aggtccgtac cggaacctac | 480 |
| cgtcagctgt tccaccccga gcagctgatc actggtaagg aggatgcggc caacaactac | 540 |
| gcccgtggcc actacaccat cggcaaggag atcgtcgatc tggttctgga caggatccgc | 600 |
| aagctggccg atcagtgcac cggtctgcag ggcttcctca tcttccactc gttcggtgga | 660 |

```
ggtaccggct ccggcttcac ctcgctgctg atggagcgtc tctccgtgga ctacggcaag    720
aagtccaagc tggagttcgc catctaccca gcccccagg tgtccactgc cgtggtcgag     780
ccctacaact ccatcctgac cacccacacc accctggagc attccgactg cgccttcatg    840
gtcgacaacg aggctatcta cgacatctgc cgccgcaatc tggacattga gcgcccacg     900 tacaccaacc tgaaccgtct gattggccag atcgtgtcct cgattaccgc ctctctgcga    960
ttcgatggtg cccttaacgt ggatctgact gagttccaga ccaacttggt gccctaccca    1020
cgtattcact ccctctggt gacctacgcc cccgttatct ccgccgagaa ggcctaccac     1080
gagcagctgt cggtggctga tcaccaac gcctgcttcg agccggccaa ccagatggtc      1140
aagtgcgatc cccgtcacgg caagtacatg gcctgctgca tgctgtaccg cggtgatgtt    1200
gtgcccaagg acgtcaacgc cgctattgcc accatcaaga ccaagcgcac cattcaattc    1260
gtcgactggt gccccactgg cttcaaggtt ggcatcaact accagccacc caccgtggtg    1320
cctggaggtg atttggccaa ggtgcagcgt gccgtgtgca tgttgtccaa caccacggcc    1380
atcgccgagg cctgggcccg tctggaccac aagttcgatc tgatgtacgc caagcgtgcc    1440
agatcggaag agcacacgtc tgaactccag tcacaatcag tctcgtatct cgtatgccgt    1500
cttctgcttg ttgtcgactc tagggataac agggtaatga gtcgacaaca agcagaagac    1560
ggcatacgag attggtcaac gatagtctcg tgggctcgga gatgtgtata agagacagtg    1620
gtttcacctc acgacaagct gtctcttata cacatctgac gctgccgacg aatcaccagg    1680
tgtgtgtaga tctcggtggt cgccgtatca ttttgtcgac tc                        1722

<210> SEQ ID NO 34
<211> LENGTH: 61
<212> TYPE: DNA
<213> ORGANISM: Artificial Sequence
<220> FEATURE:
<223> OTHER INFORMATION: synthetic

<400> SEQUENCE: 34
gagtcgacaa aatgatacgg cgaccaccga gatctacaca cacaggttcg tcggcagcgt    60
c                                                                    61

<210> SEQ ID NO 35
<211> LENGTH: 57
<212> TYPE: DNA
<213> ORGANISM: Artificial Sequence
<220> FEATURE:
<223> OTHER INFORMATION: synthetic

<400> SEQUENCE: 35
gagtcgacaa caagcagaag acggcatacg agattcaacg gcgtctcgtg ggctcgg       57

<210> SEQ ID NO 36
<211> LENGTH: 70
<212> TYPE: DNA
<213> ORGANISM: Artificial Sequence
<220> FEATURE:
<223> OTHER INFORMATION: synthetic

<400> SEQUENCE: 36
caagcagaag acggcatacg agattggtca acgatagtct cgtgggctcg agatgtgta    60 taagagacag                                                          70

<210> SEQ ID NO 37
```

```
<211> LENGTH: 155
<212> TYPE: DNA
<213> ORGANISM: Artificial Sequence
<220> FEATURE:
<223> OTHER INFORMATION: synthetic

<400> SEQUENCE: 37
tcctcatcca acgcgtcagt ttttgacaga atcgttagtt gatggcgaaa ggtcgcaaag      60
taagagcttc tcgagctgcg caaggatagg tcgaattttc tcattttccg ccagcagtcc     120
acttcgattt aattcgtaaa caagcagtag taatt                                155

<210> SEQ ID NO 38
<211> LENGTH: 63
<212> TYPE: DNA
<213> ORGANISM: Artificial Sequence
<220> FEATURE:
<223> OTHER INFORMATION: synthetic

<400> SEQUENCE: 38
gcgcagctcg agaagctctt actttgcgac ctttcgccat caactaacga ttctgtcaaa      60
aac                                                                    63

<210> SEQ ID NO 39
<211> LENGTH: 141
<212> TYPE: DNA
<213> ORGANISM: Artificial Sequence
<220> FEATURE:
<223> OTHER INFORMATION: synthetic

<400> SEQUENCE: 39
aaatttctat gaaggatgtt ttccgttctg gtgattcgtc taagaagttt aagattgctg      60
agggtcagtg gtatcgttat gcgccttcgt atgtttctcc tgcttatcac cttcttgaag     120
gcttcccatt cattcaggaa c                                                141

<210> SEQ ID NO 40
<211> LENGTH: 246
<212> TYPE: DNA
<213> ORGANISM: Artificial Sequence
<220> FEATURE:
<223> OTHER INFORMATION: synthetic

<400> SEQUENCE: 40
ggtcataatc atggtggcga ataagtacgc gttcttgcaa atcaccagaa ggcggttcct      60
gaatgaatgg gaagccttca agaaggtgat aagcaggaga acatacgaa ggcgcataac     120 gataccactg accctcagca atcttaaact tcttagacga atcaccagaa cggaaaacat    180
ccttcataga aatttcacgc ggcggcaagt tgccatacaa acagggtcg ccagcaatat     240 cggtat                                                                246

<210> SEQ ID NO 41
<211> LENGTH: 174
<212> TYPE: DNA
<213> ORGANISM: Artificial Sequence
<220> FEATURE:
<223> OTHER INFORMATION: synthetic

<400> SEQUENCE: 41
gtattaagga tgagtgttca agattgctgg aggcctccac tatgaaatcg cgtagaggct      60
ttgctattca gcgtttgatg aatgcaatgc gacaggctca tgctgatggt tggtttatcg     120
tttttgacac tctcacgttg gctgacgacc gattagaggc gttttatgat aatc            174
```

<210> SEQ ID NO 42
<211> LENGTH: 241
<212> TYPE: DNA
<213> ORGANISM: Artificial Sequence
<220> FEATURE:
<223> OTHER INFORMATION: synthetic

<400> SEQUENCE: 42

```
ggtttatcgt ttttgacact ctcacgttgg ctgacgaccg attagaggcg ttttatgata      60
atcccaatgc tttgcgtgac tatttttcgtg atattggtcg tatggttctt gctgccgagg     120
gtcgcaaggc taatgattca cacgccgact gctatcagta tttttgtgtg cctgagtatg     180
gtacagctaa tggccgtctt catttccatg cggtgcactt tatgcggaca cttcctacag     240
g                                                                     241
```

<210> SEQ ID NO 43
<211> LENGTH: 601
<212> TYPE: DNA
<213> ORGANISM: Artificial Sequence
<220> FEATURE:
<223> OTHER INFORMATION: synthetic

<400> SEQUENCE: 43

```
ccgttctggt gattcgtcta agaagtttaa gattgctgag ggtcagtggt atcgttatgc      60
gccttcgtat gtttctcctg cttatcacct tcttgaaggc ttcccattca ttcaggaacc     120
gccttctggt gatttgcaag aacgcgtact tattcgccac catgattatg accagtgttt     180
ccagtccgtt cagttgttgc agtggaatag tcaggttaaa tttaatgtga ccgtttatcg     240
caatctgccg accactcgcg attcaatcat gacttcgtga taaaagattg agtgtgaggt     300
tataacgccg aagcggtaaa aattttaatt tttgccgctg aggggttgac caagcgaagc     360
gcggtaggtt ttctgcttag gagtttaatc atgtttcaga cttttatttc tcgccataat     420
tcaaactttt tttctgataa gctggttctc acttctgtta ctccagcttc ttcggcacct     480
gttttacaga cacctaaagc tacatcgtca acgttatatt tgatagtttt gacggttaat     540
gctggtaatg gtggttttct tcattgcatt cagatggata catctgtcaa cgccgctaat     600
c                                                                     601
```

<210> SEQ ID NO 44
<211> LENGTH: 687
<212> TYPE: DNA
<213> ORGANISM: Artificial Sequence
<220> FEATURE:
<223> OTHER INFORMATION: synthetic

<400> SEQUENCE: 44

```
cttataccga tattgctggc gaccctgttt tgtatggcaa cttgccgccg cgtgaaattt      60
ctatgaagga tgttttccgt tctggtgatt cgtctaagaa gtttaagatt gctgagggtc     120
agtggtatcg ttatgcgcct tcgtatgttt ctcctgctta tcaccttctt gaaggcttcc     180
cattcattca ggaaccgcct tctggtgatt tgcaagaacg cgtacttatt cgccaccatg     240
attatgacca gtgtttccag tccgttcagt tgttgcagtg gaatagtcag gttaaattta     300
atgtgaccgt ttatcgcaat ctgccgacca ctcgcgattc aatcatgact tcgtgataaa     360
agattgagtg tgaggttata acgccgaagc ggtaaaaatt ttaattttttg ccgctgaggg     420 gttgaccaag cgaagcgcgg taggttttct gcttaggagt ttaatcatgt ttcagacttt     480
```

| | |
|---|---|
| tatttctcgc cataattcaa acttttttc tgataagctg gttctcactt ctgttactcc | 540 |
| agcttcttcg gcacctgttt tacagacacc taaagctaca tcgtcaacgt tatatttga | 600 |
| tagtttgacg gttaatgctg gtaatggtgg ttttcttcat tgcattcaga tggatacatc | 660 |
| tgtcaacgcc gctaatcagg ttgtttc | 687 |

<210> SEQ ID NO 45
<211> LENGTH: 620
<212> TYPE: DNA
<213> ORGANISM: Artificial Sequence
<220> FEATURE:
<223> OTHER INFORMATION: synthetic

<400> SEQUENCE: 45

| | |
|---|---|
| ggcttgtggc atttctactc tttctcaatc cccaatgctt ggcttccata agcagatgga | 60 |
| taaccgcatc aagctcttgg aagagattct gtcttttcgt atgcagggcg ttgagttcga | 120 |
| taatggtgat atgtatgttg acggccataa ggctgcttct gacgttcgtg atgagtttgt | 180 |
| atctgttact gagaagttaa tggatgaatt ggcacaatgc tacaatgtgc tcccccaact | 240 |
| tgatattaat aacactatag accaccgccc cgaaggggac gaaaaatggt ttttagagaa | 300 |
| cgagaagacg gttacgcagt tttgccgcaa gctggctgct gaacgccctc ttaaggatat | 360 |
| tcgcgatgag tataattacc ccaaaaagaa aggtattaag gatgagtgtt caagattgct | 420 |
| ggaggcctcc actatgaaat cgcgtagagg ctttgctatt cagcgtttga tgaatgcaat | 480 |
| gcgacaggct catgctgatg gttggtttat cgttttgac actctcacgt tggctgacga | 540 |
| ccgattagag gcgttttatg ataatcccaa tgctttgcgt gactattttc gtgatattgg | 600 |
| tcgtatggtt cttgctgccg | 620 |

<210> SEQ ID NO 46
<211> LENGTH: 457
<212> TYPE: DNA
<213> ORGANISM: Artificial Sequence
<220> FEATURE:
<223> OTHER INFORMATION: synthetic

<400> SEQUENCE: 46

| | |
|---|---|
| ggtcggcaga ttgcgataaa cggtcacatt aaatttaacc tgactattcc actgcaacaa | 60 |
| ctgaacggac tggaaacact ggtcataatc atggtggcga ataagtacgc gttcttgcaa | 120 |
| atcaccagaa ggcggttcct gaatgaatgg gaagccttca agaaggtgat aagcaggaga | 180 |
| aacatacgaa ggcgcataac gataccactg accctcagca atcttaaact tcttagacga | 240 |
| atcaccagaa cggaaaacat ccttcataga aatttcacgc ggcggcaagt tgccatacaa | 300 |
| aacagggtcg ccagcaatat cggtataagt caaagcacct ttagcgttaa ggtactgaat | 360 |
| ctctttagtc gcagtaggcg gaaaacgaac aagcgcaaga gtaaacatag tgccatgctc | 420 |
| aggaacaaag aaacgcggca cagaatgttt ataggtc | 457 |

<210> SEQ ID NO 47
<211> LENGTH: 482
<212> TYPE: DNA
<213> ORGANISM: Artificial Sequence
<220> FEATURE:
<223> OTHER INFORMATION: synthetic

<400> SEQUENCE: 47

| | |
|---|---|
| gtgttaatgc cactcctctc ccgactgtta acactactgg ttatattgac catgccgctt | 60 |
| ttcttggcac gattaaccct gataccaata aaatccctaa gcatttgttt cagggttatt | 120 |

```
tgaatatcta taacaactat tttaaagcgc cgtggatgcc tgaccgtacc gaggctaacc    180
ctaatgagct taatcaagat gatgctcgtt atggtttccg ttgctgccat ctcaaaaaca    240
tttggactgc tccgcttcct cctgagactg agctttctcg ccaaatgacg acttctacca    300
catctattga cattatgggt ctgcaagctg cttatgctaa tttgcatact gaccaagaac    360
gtgattactt catgcagcgt taccatgatg ttatttcttc atttggaggt aaaacctctt    420
atgacgctga caaccgtcct ttacttgtca tgcgctctaa tctctgggca tctggctatg    480
at                                                                  482

<210> SEQ ID NO 48
<211> LENGTH: 699
<212> TYPE: DNA
<213> ORGANISM: Artificial Sequence
<220> FEATURE:
<223> OTHER INFORMATION: synthetic

<400> SEQUENCE: 48
ctgctattga ggcttgtggc atttctactc tttctcaatc cccaatgctt ggcttccata     60
agcagatgga taaccgcatc aagctcttgg aagagattct gtcttttcgt atgcagggcg    120
ttgagttcga taatggtgat atgtatgttg acggccataa ggctgcttct gacgttcgtg    180
atgagtttgt atctgttact gagaagttaa tggatgaatt ggcacaatgc tacaatgtgc    240 tccccccaact tgatattaat aacactatag accaccgccc cgaaggggac gaaaaatggt    300
ttttagagaa cgagaagacg gttacgcagt tttgccgcaa gctggctgct gaacgccctc    360
ttaaggatat tcgcgatgag tataattacc ccaaaaagaa aggtattaag gatgagtgtt    420
caagattgct ggaggcctcc actatgaaat cgcgtagagg ctttgctatt cagcgtttga    480
tgaatgcaat gcgacaggct catgctgatg gttggtttat cgttttttgac actctcacgt    540 tggctgacga ccgattagag gcgttttatg ataatcccaa tgctttgcgt gactattttc    600
gtgatattgg tcgtatggtt cttgctgccg agggtcgcaa ggctaatgat tcacacgccg    660
actgctatca gtattttgt gtgcctgagt atggtacag                           699

<210> SEQ ID NO 49
<211> LENGTH: 405
<212> TYPE: DNA
<213> ORGANISM: Artificial Sequence
<220> FEATURE:
<223> OTHER INFORMATION: synthetic

<400> SEQUENCE: 49
gcgaactgcg atgggcatac tgtaaccata aggccacgta ttttgcaagc tatttaactg     60
gcggcgattg cgtacccgac gaccaaaatt agggtcaacg ctacctgtag gaagtgtccg    120
cataaagtgc accgcatgga atgaagacg gccattagct gtaccatact caggcacaca     180
aaaatactga tagcagtcgg cgtgtgaatc attagccttg cgaccctcgg cagcaagaac    240
catacgacca atatcacgaa aatagtcacg caaagcattg ggattatcat aaaacgcctc    300
taatcggtcg tcagccaacg tgagagtgtc aaaaacgata aaccaaccat cagcatgagc    360
ctgtcgcatt gcattcatca aacgctgaat agcaaagcct ctacg                   405

<210> SEQ ID NO 50
<211> LENGTH: 737
<212> TYPE: DNA
<213> ORGANISM: Artificial Sequence
<220> FEATURE:
```

<223> OTHER INFORMATION: synthetic

<400> SEQUENCE: 50

| | |
|---|---|
| ccgtcaaact atcaaaatat aacgttgacg atgtagcttt aggtgtctgt aaaacaggtg | 60 |
| ccgaagaagc tggagtaaca gaagtgagaa ccagcttatc agaaaaaaag tttgaattat | 120 |
| ggcgagaaat aaaagtctga aacatgatta aactcctaag cagaaaacct accgcgcttc | 180 |
| gcttggtcaa cccctcagcg gcaaaaatta aaattttac cgcttcggcg ttataacctc | 240 |
| acactcaatc ttttatcacg aagtcatgat tgaatcgcga gtggtcggca gattgcgata | 300 |
| aacggtcaca ttaaatttaa cctgactatt ccactgcaac aactgaacgg actggaaaca | 360 |
| ctggtcataa tcatggtggc gaataagtac gcgttcttgc aaatcaccag aaggcggttc | 420 |
| ctgaatgaat gggaagcctt caagaaggtg ataagcagga gaaacatacg aaggcgcata | 480 |
| acgataccac tgaccctcag caatcttaaa cttcttagac gaatcaccag aacggaaaac | 540 |
| atccttcata gaaatttcac gcggcggcaa gttgccatac aaaacagggt cgccagcaat | 600 |
| atcggtataa gtcaaagcac ctttagcgtt aaggtactga atctctttag tcgcagtagg | 660 |
| cggaaaacga acaagcgcaa gagtaaacat agtgccatgc tcaggaacaa agaaacgcgg | 720 |
| cacagaatgt ttatagg | 737 |

<210> SEQ ID NO 51
<211> LENGTH: 56
<212> TYPE: DNA
<213> ORGANISM: Artificial Sequence
<220> FEATURE:
<223> OTHER INFORMATION: synthetic

<400> SEQUENCE: 51

| | |
|---|---|
| agtaaacata gtgccatgct caggaacaaa gaaacgcggc acagaatgtt tatagg | 56 |

<210> SEQ ID NO 52
<211> LENGTH: 345
<212> TYPE: DNA
<213> ORGANISM: Artificial Sequence
<220> FEATURE:
<223> OTHER INFORMATION: synthetic

<400> SEQUENCE: 52

| | |
|---|---|
| gttgaggctt gcgtttatgg tacgctggac tttgtaggat accctcgctt tcctgctcct | 60 |
| gttgagttta ttgctgccgt cattgcttat tatgttcatc ccgtcaacat tcaaacggcc | 120 |
| tgtctcatca tggaaggcgc tgaatttacg gaaaacatta ttaatggcgt cgagcgtccg | 180 |
| gttaaagccg ctgaattgtt cgcgtttacc ttgcgtgtac gcgcaggaaa cactgacgtt | 240 |
| cttactgacg cagaagaaaa cgtgcgtcaa aaattacgtg cagaaggagt gatgtaatgt | 300 |
| ctaaaggtaa aaaacgttct ggcgctcgcc ctggtcgtcc gcagc | 345 |

<210> SEQ ID NO 53
<211> LENGTH: 537
<212> TYPE: DNA
<213> ORGANISM: Artificial Sequence
<220> FEATURE:
<223> OTHER INFORMATION: synthetic

<400> SEQUENCE: 53

| | |
|---|---|
| agttgaaatg gtaataagac gaccaatctg accagcaagg aagccaagat gggaaaggtc | 60 |
| atgcggcata cgctcggcgc cagtttgaat attagacata atttatcctc aagtaagggg | 120 |
| ccgaagcccc tgcaattaaa attgttgacc acctacatac caaagacgag cgcctttacg | 180 |

```
cttgccttta gtacctcgca acggctgcgg acgaccaggg cgagcgccag aacgttttt       240 acctttagac attacatcac tccttctgca cgtaattttt gacgcacgtt ttcttctgcg      300
tcagtaagaa cgtcagtgtt tcctgcgcgt acacgcaagg taaacgcgaa caattcagcg      360
gctttaaccg gacgctcgac gccattaata atgttttccg taaattcagc gccttccatg      420
atgagacagg ccgtttgaat gttgacggga tgaacataat aagcaatgac ggcagcaata      480
aactcaacag gagcaggaaa gcgagggtat cctacaaagt ccagcgtacc ataaacg         537
```

<210> SEQ ID NO 54
<211> LENGTH: 423
<212> TYPE: DNA
<213> ORGANISM: Artificial Sequence
<220> FEATURE:
<223> OTHER INFORMATION: synthetic

<400> SEQUENCE: 54

```
gcgccagttt gaatattaga cataatttat cctcaagtaa ggggccgaag cccctgcaat       60
taaaattgtt gaccacctac ataccaaaga cgagcgcctt tacgcttgcc tttagtacct      120
cgcaacggct gcggacgacc agggcgagcg ccagaacgtt ttttaccttt agacattaca      180
tcactccttc tgcacgtaat ttttgacgca cgttttcttc tgcgtcagta agaacgtcag      240
tgtttcctgc gcgtacacgc aaggtaaacg cgaacaattc agcggcttta accgacgct       300 cgacgccatt aataatgttt tccgtaaatt cagcgccttc catgatgaga caggccgttt      360
gaatgttgac gggatgaaca taataagcaa tgacggcagc aataaactca acaggagcag      420
gaa                                                                   423
```

<210> SEQ ID NO 55
<211> LENGTH: 343
<212> TYPE: DNA
<213> ORGANISM: Artificial Sequence
<220> FEATURE:
<223> OTHER INFORMATION: synthetic

<400> SEQUENCE: 55

```
ctcttaagga tattcgcgat gagtataatt accccaaaaa gaaaggtatt aaggatgagt       60
gttcaagatt gctggaggcc tccactatga atcgcgtag aggctttgct attcagcgtt      120
tgatgaatgc aatgcgacag gctcatgctg atggttggtt tatcgttttt gacactctca      180
cgttggctga cgaccgatta gaggcgtttt atgataatcc caatgctttg cgtgactatt      240
ttcgtgatat tggtcgtatg gttcttgctg ccgagggtcg caaggctaat gattcacacg      300
ccgactgcta tcagtatttt tgtgtgcctg agtatggtac agc                       343
```

<210> SEQ ID NO 56
<211> LENGTH: 353
<212> TYPE: DNA
<213> ORGANISM: Artificial Sequence
<220> FEATURE:
<223> OTHER INFORMATION: synthetic

<400> SEQUENCE: 56

```
ggttattata ccgtcaagga ctgtgtgact attgacgtcc ttccccgtac gccgggcaat       60
aatgtttatg ttggtttcat ggtttggtct aactttaccg ctactaaatg ccgcggattg      120
gtttcgctga atcaggttat taaagagatt atttgtctcc agccacttaa gtgaggtgat      180
ttatgtttgg tgctattgct ggcggtattg cttctgctct tgctggtggc gccatgtcta      240
```

```
aattgtttgg aggcggtcaa aaagccgcct ccggtggcat tcaaggtgat gtgcttgcta      300
ccgataacaa tactgtaggc atgggtgatg ctggtattaa atctgccatt caa             353
```

<210> SEQ ID NO 57
<211> LENGTH: 429
<212> TYPE: DNA
<213> ORGANISM: Artificial Sequence
<220> FEATURE:
<223> OTHER INFORMATION: synthetic

<400> SEQUENCE: 57

```
cgcctactgc gactaaagag attcagtacc ttaacgctaa aggtgctttg acttataccg      60
atattgctgg cgaccctgtt ttgtatggca acttgccgcc gcgtgaaatt tctatgaagg     120
atgttttccg ttctggtgat tcgtctaaga agtttaagat tgctgagggt cagtggtatc     180
gttatgcgcc ttcgtatgtt tctcctgctt atcaccttct tgaaggcttc ccattcattc     240
aggaaccgcc ttctggtgat ttgcaagaac gcgtacttat tcgccaccat gattatgacc     300
agtgtttcca gtccgttcag ttgttgcagt ggaatagtca ggttaaattt aatgtgaccg     360
tttatcgcaa tctgccgacc actcgcgatt caatcatgac ttcgtgataa aagattgagt     420
gtgaggtta                                                             429
```

<210> SEQ ID NO 58
<211> LENGTH: 326
<212> TYPE: DNA
<213> ORGANISM: Artificial Sequence
<220> FEATURE:
<223> OTHER INFORMATION: synthetic

<400> SEQUENCE: 58

```
cgttgacgat gtagctttag gtgtctgtaa aacaggtgcc gaagaagctg gagtaacaga      60
agtgagaacc agcttatcag aaaaaaagtt tgaattatgg cgagaaataa aagtctgaaa     120
catgattaaa ctcctaagca gaaaacctac cgcgcttcgc ttggtcaacc cctcagcggc     180
aaaaattaaa attttaccg cttcggcgtt ataacctcac actcaatctt ttatcacgaa      240
gtcatgattg aatcgcgagt ggtcggcaga ttgcgataaa cggtcacatt aaatttaacc     300
tgactattcc actgcaacaa ctgaac                                          326
```

<210> SEQ ID NO 59
<211> LENGTH: 447
<212> TYPE: DNA
<213> ORGANISM: Artificial Sequence
<220> FEATURE:
<223> OTHER INFORMATION: synthetic

<400> SEQUENCE: 59

```
ccagaaaact ggcctaacga cgtttggtca gttccatcaa catcatagcc agatgcccag      60
agattagagc gcatgacaag taaggacgg ttgtcagcgt cataagaggt tttacctcca     120
aatgaagaaa taacatcatg gtaacgctgc atgaagtaat cacgttcttg gtcagtatgc     180
aaattagcat aagcagcttg cagacccata atgtcaatag atgtggtaga agtcgtcatt     240
tggcgagaaa gctcagtctc aggaggaagc ggagcagtcc aaatgttttt gagatggcag     300
caacggaaac cataacgagc atcatcttga ttaagctcat tagggttagc ctcggtacgg     360
tcaggcatcc acggcgcttt aaaatagttg ttatagatat tcaaataacc ctgaaacaaa     420
tgcttaggga ttttattggt atcaggg                                         447
```

<210> SEQ ID NO 60
<211> LENGTH: 610
<212> TYPE: DNA
<213> ORGANISM: Artificial Sequence
<220> FEATURE:
<223> OTHER INFORMATION: synthetic

<400> SEQUENCE: 60

```
gtcctttact tgtcatgcgc tctaatctct gggcatctgg ctatgatgtt gatggaactg      60
accaaacgtc gttaggccag ttttctggtc gtgttcaaca gacctataaa cattctgtgc     120
cgcgtttctt tgttcctgag catggcacta tgtttactct tgcgcttgtt cgttttccgc     180
ctactgcgac taaagagatt cagtacctta acgctaaagg tgctttgact tataccgata     240
ttgctggcga ccctgttttg tatggcaact gccgccgcg tgaaatttct atgaaggatg      300
ttttccgttc tggtgattcg tctaagaagt ttaagattgc tgagggtcag tggtatcgtt     360
atgcgccttc gtatgtttct cctgcttatc accttcttga aggcttccca ttcattcagg     420
aaccgccttc tggtgatttg caagaacgcg tacttattcg ccaccatgat tatgaccagt     480
gtttccagtc cgttcagttg ttgcagtgga atagtcaggt taaatttaat gtgaccgttt     540
atcgcaatct gccgaccact cgcgattcaa tcatgacttc gtgataaaag attgagtgtg     600
aggttataac                                                             610
```

<210> SEQ ID NO 61
<211> LENGTH: 434
<212> TYPE: DNA
<213> ORGANISM: Artificial Sequence
<220> FEATURE:
<223> OTHER INFORMATION: synthetic

<400> SEQUENCE: 61

```
tcatggaagc gataaaactc tgcaggttgg atacgccaat catttttatc gaagcgcgca      60
taaatttgag cagatttgtc gtcacaggtt gcgccgccaa aacgtcggct acagtaactt     120
ttcccagcct caatctcatc tctcttttg cgttctgctt caatatctgg ttgaacggcg      180
tcgcgtcgta acccagcttg gtaagttgga ttaagcactc cgtggacaga tttgtcattg     240
tgagcatttt catcccgaag ttgcggctca ttctgattct gaacagcttc ttgggaagta     300
gcgacagctt ggttttagt gagttgttcc attctttagc tcctagacct ttagcagcaa      360
ggtccatatc tgacttttg ttaacgtatt tagccacata gaaaccaaca gccatataac      420
tggtagcttt aagc                                                        434
```

<210> SEQ ID NO 62
<211> LENGTH: 510
<212> TYPE: DNA
<213> ORGANISM: Artificial Sequence
<220> FEATURE:
<223> OTHER INFORMATION: synthetic

<400> SEQUENCE: 62

```
tcatagtgga ggcctccagc aatcttgaac actcatcctt aataccttc tttttgggt        60
aattatactc atcgcgaata tccttaagag ggcgttcagc agccagcttg cggcaaaact     120
gcgtaaccgt cttctcgttc tctaaaaacc attttcgtc cccttcgggg cggtggtcta      180
tagtgttatt aatatcaagt tggggagca cattgtagca ttgtgccaat tcatccatta      240
acttctcagt aacagataca aactcatcac gaacgtcaga agcagccta tggccgtcaa      300
catacatatc accattatcg aactcaacgc cctgcatacg aaaagacaga atctcttcca     360
```

```
agagcttgat gcggttatcc atctgcttat ggaagccaag cattggggat tgagaaagag      420
tagaaatgcc acaagcctca atagcaggtt taagagcctc gatacgctca aagtcaaaat      480
aatcagcgtg acattcagaa gggtaataag                                       510
```

<210> SEQ ID NO 63
<211> LENGTH: 738
<212> TYPE: DNA
<213> ORGANISM: Artificial Sequence
<220> FEATURE:
<223> OTHER INFORMATION: synthetic

<400> SEQUENCE: 63

```
ctcttgcgct tgttcgtttt ccgcctactg cgactaaaga gattcagtac cttaacgcta       60
aaggtgcttt gacttatacc gatattgctg gcgaccctgt tttgtatggc aacttgccgc      120
cgcgtgaaat ttctatgaag gatgttttcc gttctggtga ttcgtctaag aagtttaaga      180
ttgctgaggg tcagtggtat cgttatgcgc cttcgtatgt ttctcctgct tatcaccttc      240
ttgaaggctt cccattcatt caggaaccgc cttctggtga ttttgcaagaa cgcgtactta      300 ttcgccacca tgattatgac cagtgttttcc agtccgttca gttgttgcag tggaatagtc      360
aggttaaatt taatgtgacc gtttatcgca atctgccgac cactcgcgat tcaatcatga      420
cttcgtgata aagattgag tgtgaggtta taacgccgaa gcggtaaaaa tttttaatttt      480 tgccgctgag gggttgacca agcgaagcgc ggtaggtttt ctgcttagga gtttaatcat      540
gtttcagact tttatttctc gccataattc aaacttttt tctgataagc tggttctcac       600
ttctgttact ccagcttctt cggcacctgt tttacagaca cctaaagcta catcgtcaac      660
gttatatttt gatagtttga cggttaatgc tggtaatggt ggttttcttc attgcattca      720
gatggataca tctgtcaa                                                    738
```

<210> SEQ ID NO 64
<211> LENGTH: 553
<212> TYPE: DNA
<213> ORGANISM: Artificial Sequence
<220> FEATURE:
<223> OTHER INFORMATION: synthetic

<400> SEQUENCE: 64

```
taagacgacc aatctgacca gcaaggaagc caagatggga aaggtcatgc ggcatacgct       60
cggcgccagt ttgaatatta gacataattt atcctcaagt aaggggccga agcccctgca      120
attaaaattg ttgaccacct ataccaaa gacgagcgcc tttacgcttg cctttagtac        180
ctcgcaacgg ctgcggacga ccagggcgag cgccagaacg tttttttacct ttagacatta    240 catcactcct tctgcacgta attttttgacg cacgttttct tctgcgtcag taagaacgtc    300 agtgttttcct gcgcgtacac gcaaggtaaa cgcgaacaat tcagcggctt taaccggacg    360
ctcgacgcca ttaataatgt tttccgtaaa ttcagcgcct tccatgatga acaggccgt     420 ttgaatgttg acgggatgaa cataataagc aatgacggca gcaataaact caacaggagc    480
aggaaagcga gggtatccta caaagtccag cgtaccataa acgcaagcct caacgcagcg    540
acgagcacga gag                                                       553
```

<210> SEQ ID NO 65
<211> LENGTH: 456
<212> TYPE: DNA
<213> ORGANISM: Artificial Sequence
<220> FEATURE:
<223> OTHER INFORMATION: synthetic

<400> SEQUENCE: 65

| | | |
|---|---|---|
| gctcggcgcc agtttgaata ttagacataa tttatcctca agtaaggggc cgaagcccct | 60 |
| gcaattaaaa ttgttgacca cctacatacc aaagacgagc gcctttacgc ttgcctttag | 120 |
| tacctcgcaa cggctgcgga cgaccagggc gagcgccaga acgttttta cctttagaca | 180 |
| ttacatcact ccttctgcac gtaattttg acgcacgttt tcttctgcgt cagtaagaac | 240 |
| gtcagtgttt cctgcgcgta cacgcaaggt aaacgcgaac aattcagcgg ctttaaccgg | 300 |
| acgctcgacg ccattaataa tgttttccgt aaattcagcg ccttccatga tgagacaggc | 360 |
| cgtttgaatg ttgacgggat gaacataata agcaatgacg gcagcaataa actcaacagg | 420 |
| agcaggaaag cgagggtatc ctacaaagtc cagcgt | 456 |

<210> SEQ ID NO 66
<211> LENGTH: 350
<212> TYPE: DNA
<213> ORGANISM: Artificial Sequence
<220> FEATURE:
<223> OTHER INFORMATION: synthetic

<400> SEQUENCE: 66

| | | |
|---|---|---|
| gagtagttga atggtaata agacgaccaa tctgaccagc aaggaagcca agatgggaaa | 60 |
| ggtcatgcgg catacgctcg gcgccagttt gaatattaga cataatttat cctcaagtaa | 120 |
| ggggccgaag cccctgcaat taaaattgtt gaccacctac ataccaaaga cgagcgcctt | 180 |
| tacgcttgcc tttagtacct cgcaacggct gcggacgacc agggcgagcg ccagaacgtt | 240 |
| ttttaccttt agacattaca tcactccttc tgcacgtaat ttttgacgca cgttttcttc | 300 |
| tgcgtcagta agaacgtcag tgtttcctgc gcgtacacgc aaggtaaacg | 350 |

<210> SEQ ID NO 67
<211> LENGTH: 265
<212> TYPE: DNA
<213> ORGANISM: Artificial Sequence
<220> FEATURE:
<223> OTHER INFORMATION: synthetic

<400> SEQUENCE: 67

| | | |
|---|---|---|
| cgtttggtca gttccatcaa catcatagcc agatgcccag agattagagc gcatgacaag | 60 |
| taaaggacgg ttgtcagcgt cataagaggt tttacctcca aatgaagaaa taacatcatg | 120 |
| gtaacgctgc atgaagtaat cacgttcttg gtcagtatgc aaattagcat aagcagcttg | 180 |
| cagacccata atgtcaatag atgtggtaga agtcgtcatt tggcgagaaa gctcagtctc | 240 |
| aggaggaagc ggagcagtcc aaatg | 265 |

<210> SEQ ID NO 68
<211> LENGTH: 470
<212> TYPE: DNA
<213> ORGANISM: Artificial Sequence
<220> FEATURE:
<223> OTHER INFORMATION: synthetic

<400> SEQUENCE: 68

| | | |
|---|---|---|
| aatcattttt atcgaagcgc gcataaattt gagcagattt gtcgtcacag gttgcgccgc | 60 |
| caaaacgtcg gctacagtaa cttttcccag cctcaatctc atctctcttt ttgcgttctg | 120 |
| cttcaatatc tggttgaacg gcgtcgcgtc gtaacccagc ttggtaagtt ggattaagca | 180 |
| ctccgtggac agatttgtca ttgtgagcat tttcatcccg aagttgcggc tcattctgat | 240 |

```
tctgaacagc ttcttgggaa gtagcgacag cttggttttt agtgagttgt tccattcttt    300
agctcctaga cctttagcag caaggtccat atctgactt  ttgttaacgt atttagccac    360
atagaaacca acagccatat aactggtagc tttaagcggc tcacctttag catcaacagg    420
ccacaaccaa ccagaacgtg aaaaagcgtc ctgcgtgtag cgaactgcga               470
```

<210> SEQ ID NO 69
<211> LENGTH: 239
<212> TYPE: DNA
<213> ORGANISM: Artificial Sequence
<220> FEATURE:
<223> OTHER INFORMATION: synthetic

<400> SEQUENCE: 69

```
tttacttgtc atgcgctcta atctctgggc atctggctat gatgttgatg gaactgacca     60
aacgtcgtta ggccagtttt ctggtcgtgt tcaacagacc tataaacatt ctgtgccgcg    120
tttctttgtt cctgagcatg gcactatgtt tactcttgcg cttgttcgtt ttccgcctac    180
tgcgactaaa gagattcagt accttaacgc taaaggtgct ttgacttata ccgatattg    239
```

<210> SEQ ID NO 70
<211> LENGTH: 302
<212> TYPE: DNA
<213> ORGANISM: Artificial Sequence
<220> FEATURE:
<223> OTHER INFORMATION: synthetic

<400> SEQUENCE: 70

```
agaagacggt tacgcagttt tgccgcaagc tggctgctga acgccctctt aaggatattc     60
gcgatgagta taattacccc aaaaagaaag gtattaagga tgagtgttca agattgctgg    120
aggcctccac tatgaaatcg cgtagaggct ttgctattca gcgtttgatg aatgcaatgc    180
gacaggctca tgctgatggt tggtttatcg ttttgacac  tctcacgttg gctgacgacc    240
gattagaggc gtttatgat  aatcccaatg ctttgcgtga ctattttcgt gatattggtc    300
gt                                                                   302
```

<210> SEQ ID NO 71
<211> LENGTH: 615
<212> TYPE: DNA
<213> ORGANISM: Artificial Sequence
<220> FEATURE:
<223> OTHER INFORMATION: synthetic

<400> SEQUENCE: 71

```
ggtcatgcgg catacgctcg gcgccagttt gaatattaga cataatttat cctcaagtaa     60
ggggccgaag cccctgcaat taaaattgtt gaccacctac ataccaaaga cgagcgcctt    120
tacgcttgcc tttagtacct cgcaacggct gcggacgacc agggcgagcg ccagaacgtt    180
ttttaccttt agacattaca tcactccttc tgcacgtaat ttttgacgca cgttttcttc    240
tgcgtcagta agaacgtcag tgtttcctgc gcgtacacgc aaggtaaacg cgaacaattc    300
agcggcttta accggacgct cgacgccatt aataatgttt ccgtaaatt  cagcgccttc    360 catgatgaga caggccgttt gaatgttgac gggatgaaca taataagcaa tgacggcagc    420
aataaactca acaggagcag gaaagcgagg gtatcctaca aagtccagcg taccataaac    480
gcaagcctca acgcagcgac gagcacgaga gcggtcagta gcaatccaaa ctttgttact    540
cgtcagaaaa tcgaaatcat cttcggttaa atccaaaacg gcagaagcct gaatgagctt    600
aatagaggcc aaagc                                                     615
```

<210> SEQ ID NO 72
<211> LENGTH: 513
<212> TYPE: DNA
<213> ORGANISM: Artificial Sequence
<220> FEATURE:
<223> OTHER INFORMATION: synthetic

<400> SEQUENCE: 72

```
cgactgttaa cactactggt tatattgacc atgccgcttt tcttggcacg attaaccctg      60
ataccaataa aatccctaag catttgtttc agggttattt gaatatctat aacaactatt     120
ttaaagcgcc gtggatgcct gaccgtaccg aggctaaccc taatgagctt aatcaagatg     180
atgctcgtta tggtttccgt tgctgccatc tcaaaaacat ttggactgct ccgcttcctc     240
ctgagactga gctttctcgc caaatgacga cttctaccac atctattgac attatgggtc     300
tgcaagctgc ttatgctaat ttgcatactg accaagaacg tgattacttc atgcagcgtt     360
accatgatgt tatttcttca tttggaggta aaacctctta tgacgctgac aaccgtcctt     420
tacttgtcat gcgctctaat ctctgggcat ctggctatga tgttgatgga actgaccaaa     480
cgtcgttagg ccagtttcct ggtcgtgttc aac                                  513
```

<210> SEQ ID NO 73
<211> LENGTH: 238
<212> TYPE: DNA
<213> ORGANISM: Artificial Sequence
<220> FEATURE:
<223> OTHER INFORMATION: synthetic

<400> SEQUENCE: 73

```
gtatcgttat gcgccttcgt atgtttctcc tgcttatcac cttcttgaag gcttcccatt      60
cattcaggaa ccgccttctg gtgatttgca agaacgcgta cttattcgcc accatgatta     120
tgaccagtgt ttccagtccg ttcagttgtt gcagtggaat agtcaggtta aatttaatgt     180
gaccgtttat cgcaatctgc cgaccactcg cgattcaatc atgacttcgt gataaaag       238
```

<210> SEQ ID NO 74
<211> LENGTH: 523
<212> TYPE: DNA
<213> ORGANISM: Artificial Sequence
<220> FEATURE:
<223> OTHER INFORMATION: synthetic

<400> SEQUENCE: 74

```
gcctttagta cctcgcaacg gctgcggacg accagggcga gcgccagaac gttttttacc      60
tttagacatt acatcactcc ttctgcacgt aatttttgac gcacgttttc ttctgcgtca     120
gtaagaacgt cagtgtttcc tgcgcgtaca cgcaaggtaa acgcgaacaa ttcagcggct     180
ttaaccggac gctcgacgcc attaataatg ttttccgtaa attcagcgcc ttccatgatg     240
agacaggccg tttgaatgtt gacgggatga acataataag caatgacggc agcaataaac     300
tcaacaggag caggaaagcg agggtatcct acaaagtcca gcgtaccata aacgcaagcc     360
tcaacgcagc gacgagcacg agagcggtca gtagcaatcc aaactttgtt actcgtcaga     420
aaatcgaaat catcttcggt taaatccaaa acggcagaag cctgaatgag cttaatagag     480
gccaaagcgg tctggaaacg tacggattgt tcagtaactt gac                       523
```

<210> SEQ ID NO 75
<211> LENGTH: 82
<212> TYPE: DNA

```
<213> ORGANISM: Artificial Sequence
<220> FEATURE:
<223> OTHER INFORMATION: synthetic

<400> SEQUENCE: 75
tagaaatgcc acaagcctca atagcaggtt taagagcctc gatacgctca aagtcaaaat    60
aatcagcgtg acattcagaa gg                                              82

<210> SEQ ID NO 76
<211> LENGTH: 348
<212> TYPE: DNA
<213> ORGANISM: Artificial Sequence
<220> FEATURE:
<223> OTHER INFORMATION: synthetic

<400> SEQUENCE: 76
ctgtaaaaca ggtgccgaag aagctggagt aacagaagtg agaaccagct tatcagaaaa    60
aaagtttgaa ttatggcgag aaataaaagt ctgaaacatg attaaactcc taagcagaaa   120
acctaccgcg cttcgcttgg tcaacccctc agcggcaaaa attaaaattt ttaccgcttc   180
ggcgttataa cctcacactc aatcttttat cacgaagtca tgattgaatc gcgagtggtc   240
ggcagattgc gataaacggt cacattaaat ttaacctgac tattccactg caacaactga   300
acggactgga acactggtc ataatcatgg tggcgaataa gtacgcgt                  348

<210> SEQ ID NO 77
<211> LENGTH: 522
<212> TYPE: DNA
<213> ORGANISM: Artificial Sequence
<220> FEATURE:
<223> OTHER INFORMATION: synthetic

<400> SEQUENCE: 77
gaagaaaacc accattacca gcattaaccg tcaaactatc aaaatataac gttgacgatg    60
tagctttagg tgtctgtaaa acaggtgccg aagaagctgg agtaacagaa gtgagaacca   120
gcttatcaga aaaaagtttt gaattatggc gagaaataaa agtctgaaac atgattaaac   180
tcctaagcag aaaacctacc gcgcttcgct tggtcaaccc ctcagcggca aaattaaaa    240 ttttaccgc ttcggcgtta aacctcaca ctcaatcttt tatcacgaag tcatgattga    300
atcgcgagtg gtcggcagat tgcgataaac ggtcacatta aatttaacct gactattcca   360
ctgcaacaac tgaacggact ggaaacactg gtcataatca tggtggcgaa taagtacgcg   420
ttcttgcaaa tcaccagaag gcggttcctg aatgaatggg aagccttcaa gaaggtgata   480
agcaggagaa acatacgaag gcgcataacg ataccactga cc                       522

<210> SEQ ID NO 78
<211> LENGTH: 402
<212> TYPE: DNA
<213> ORGANISM: Artificial Sequence
<220> FEATURE:
<223> OTHER INFORMATION: synthetic

<400> SEQUENCE: 78
ccagcattaa ccgtcaaact atcaaaatat aacgttgacg atgtagcttt aggtgtctgt    60
aaaacaggtg ccgaagaagc tggagtaaca gaagtgagaa ccagcttatc agaaaaaag   120 tttgaattat ggcgagaaat aaaagtctga acatgatta aactcctaag cagaaaacct   180
accgcgcttc gcttggtcaa cccctcagcg gcaaaaatta aaattttac cgcttcggcg   240 ttataacctc acactcaatc ttttatcacg aagtcatgat tgaatcgcga gtggtcggca   300
```

```
gattgcgata acggtcaca ttaaatttaa cctgactatt ccactgcaac aactgaacgg    360
actggaaaca ctggtcataa tcatggtggc gaataagtac gc                     402
```

<210> SEQ ID NO 79
<211> LENGTH: 434
<212> TYPE: DNA
<213> ORGANISM: Artificial Sequence
<220> FEATURE:
<223> OTHER INFORMATION: synthetic

<400> SEQUENCE: 79

```
ccagagatta gagcgcatga caagtaaagg acggttgtca gcgtcataag aggttttacc    60
tccaaatgaa gaaataacat catggtaacg ctgcatgaag taatcacgtt cttggtcagt   120
atgcaaatta gcataagcag cttgcagacc cataatgtca atagatgtgg tagaagtcgt   180
catttggcga gaaagctcag tctcaggagg aagcggagca gtccaaatgt ttttgagatg   240
gcagcaacgg aaaccataac gagcatcatc ttgattaagc tcattagggt tagcctcggt   300
acggtcaggc atccacggcg ctttaaaata gttgttatag atattcaaat aaccctgaaa   360
caaatgctta gggattttat tggtatcagg gttaatcgtg ccaagaaaag cggcatggtc   420
aatataacca gtag                                                    434
```

<210> SEQ ID NO 80
<211> LENGTH: 354
<212> TYPE: DNA
<213> ORGANISM: Artificial Sequence
<220> FEATURE:
<223> OTHER INFORMATION: synthetic

<400> SEQUENCE: 80

```
atttaatacc agcatcaccc atgcctacag tattgttatc ggtagcaagc acatcacctt    60
gaatgccacc ggaggcggct ttttgaccgc ctccaaacaa tttagacatg gcgccaccag   120
caagagcaga agcaataccg ccagcaatag caccaaacat aaatcacctc acttaagtgg   180
ctggagacaa ataatctctt taataacctg attcagcgaa accaatccgc ggcatttagt   240
agcggtaaag ttagaccaaa ccatgaaacc aacataaaca ttattgcccg cgtacgggg    300 aaggacgtca atagtcacac agtccttgac ggtataataa ccaccatcat ggcg         354
```

<210> SEQ ID NO 81
<211> LENGTH: 301
<212> TYPE: DNA
<213> ORGANISM: Artificial Sequence
<220> FEATURE:
<223> OTHER INFORMATION: synthetic

<400> SEQUENCE: 81

```
aatttaatgt gaccgtttat cgcaatctgc cgaccactcg cgattcaatc atgacttcgt    60
gataaaagat tgagtgtgag gttataacgc cgaagcggta aaaattttaa ttttgccgc    120 tgagggttg accaagcgaa gcgcggtagg ttttctgctt aggagtttaa tcatgtttca   180
gacttttatt tctcgccata attcaaactt ttttctgat aagctggttc tcacttctgt    240
tactccagct tcttcggcac ctgttttaca gacacctaaa gctacatcgt caacgttata   300
t                                                                  301
```

<210> SEQ ID NO 82
<211> LENGTH: 528
<212> TYPE: DNA

<213> ORGANISM: Artificial Sequence
<220> FEATURE:
<223> OTHER INFORMATION: synthetic

<400> SEQUENCE: 82

```
ttaaggtact gaatctcttt agtcgcagta ggcggaaaac gaacaagcgc aagagtaaac    60
atagtgccat gctcaggaac aaagaaacgc ggcacagaat gtttataggt ctgttgaaca   120
cgaccagaaa actggcctaa cgacgtttgg tcagttccat caacatcata gccagatgcc   180
cagagattag agcgcatgac aagtaaagga cggttgtcag cgtcataaga ggttttacct   240
ccaaatgaag aaataacatc atggtaacgc tgcatgaagt aatcacgttc ttggtcagta   300
tgcaaattag cataagcagc ttgcagaccc ataatgtcaa tagatgtggt agaagtcgtc   360
atttggcgag aaagctcagt ctcaggagga agcggagcag tccaaatgtt tttgagatgg   420
cagcaacgga aaccataacg agcatcatct tgattaagct cattagggtt agcctcggta   480
cggtcaggca tccacggcgc tttaaaatag ttgttataga tattcaaa              528
```

<210> SEQ ID NO 83
<211> LENGTH: 347
<212> TYPE: DNA
<213> ORGANISM: Artificial Sequence
<220> FEATURE:
<223> OTHER INFORMATION: synthetic

<400> SEQUENCE: 83

```
cttctgaatg tcacgctgat tattttgact ttgagcgtat cgaggctctt aaacctgcta    60
ttgaggcttg tggcatttct actctttctc aatccccaat gcttggcttc cataagcaga   120
tggataaccg catcaagctc ttggaagaga ttctgtcttt tcgtatgcag ggcgttgagt   180
tcgataatgg tgatatgtat gttgacggcc ataaggctgc ttctgacgtt cgtgatgagt   240
ttgtatctgt tactgagaag ttaatggatg aattggcaca atgctacaat gtgctccccc   300
aacttgatat taataacact atagaccacc gccccgaagg ggacgaa                347
```

<210> SEQ ID NO 84
<211> LENGTH: 470
<212> TYPE: DNA
<213> ORGANISM: Artificial Sequence
<220> FEATURE:
<223> OTHER INFORMATION: synthetic

<400> SEQUENCE: 84

```
gtttataggt ctgttgaaca cgaccagaaa actggcctaa cgacgtttgg tcagttccat    60
caacatcata gccagatgcc cagagattag agcgcatgac aagtaaagga cggttgtcag   120
cgtcataaga ggttttacct ccaaatgaag aaataacatc atggtaacgc tgcatgaagt   180
aatcacgttc ttggtcagta tgcaaattag cataagcagc ttgcagaccc ataatgtcaa   240
tagatgtggt agaagtcgtc atttggcgag aaagctcagt ctcaggagga agcggagcag   300
tccaaatgtt tttgagatgg cagcaacgga aaccataacg agcatcatct tgattaagct   360
cattagggtt agcctcggta cggtcaggca tccacggcgc tttaaaatag ttgttataga   420
tattcaaata accctgaaac aaatgcttag ggattttatt ggtatcaggg              470
```

<210> SEQ ID NO 85
<211> LENGTH: 183
<212> TYPE: DNA
<213> ORGANISM: Artificial Sequence
<220> FEATURE:
<223> OTHER INFORMATION: synthetic

<400> SEQUENCE: 85

```
gcttaatcaa gatgatgctc gttatggttt ccgttgctgc catctcaaaa acatttggac    60
tgctccgctt cctcctgaga ctgagctttc tcgccaaatg acgacttcta ccacatctat   120
tgacattatg ggtctgcaag ctgcttatgc taatttgcat actgaccaag aacgtgatta   180
ctt                                                                 183
```

<210> SEQ ID NO 86
<211> LENGTH: 382
<212> TYPE: DNA
<213> ORGANISM: Artificial Sequence
<220> FEATURE:
<223> OTHER INFORMATION: synthetic

<400> SEQUENCE: 86

```
ttcgtatgca gggcgttgag ttcgataatg gtgatatgta tgttgacggc cataaggctg    60
cttctgacgt tcgtgatgag tttgtatctg ttactgagaa gttaatggat gaattggcac   120
aatgctacaa tgtgctcccc caacttgata ttaataacac tatagaccac cgccccgaag   180
gggacgaaaa atggtttta gagaacgaga agacggttac gcagttttgc cgcaagctgg   240
ctgctgaacg ccctcttaag gatattcgcg atgagtataa ttaccccaaa agaaaggta   300
ttaaggatga gtgttcaaga ttgctggagg cctccactat gaaatcgcgt agaggctttg   360
ctattcagcg tttgatgaat gc                                            382
```

<210> SEQ ID NO 87
<211> LENGTH: 929
<212> TYPE: DNA
<213> ORGANISM: Artificial Sequence
<220> FEATURE:
<223> OTHER INFORMATION: synthetic

<400> SEQUENCE: 87

```
cctgctattg aggcttgtgg catttctact ctttctcaat ccccaatgct tggcttccat    60
aagcagatgg ataaccgcat caagctcttg gaagagattc tgtcttttcg tatgcagggc   120
gttgagttcg ataatggtga tatgtatgtt gacggccata aggctgcttc tgacgttcgt   180
gatgagtttg tatctgttac tgagaagtta atggatgaat ggcacaatg ctacaatgtg   240
ctcccccaac ttgatattaa taacactata gaccaccgcc ccgaagggga cgaaaaatgg   300
tttttagaga acgagaagac ggttacgcag ttttgccgca agctggctgc tgaacgccct   360
cttaaggata ttcgcgatga gtataattac cccaaaaaga aaggtattaa ggatgagtgt   420
tcaagattgc tggaggcctc cactatgaaa tcgcgtagag ctttgctat cagcgtttg   480
atgaatgcaa tgcgacaggc tcatgctgat ggttggttta tcgtttttga cactctcacg   540
ttggctgacg accgattaga ggcgttttat gataatccca atgctttgcg tgactatttt   600
cgtgatattg tcgtatggt tcttgctgcc gagggtcgca aggctaatga ttcacacgcc   660
gactgctatc agtatttttg tgtgcctgag tatggtacag ctaatggccg tcttcatttc   720
catgcggtgc actttatgcg gacacttcct acaggtagcg ttgaccctaa ttttggtcgt   780
cgggtacgca atcgccgcca gttaaatagc ttgcaaaata cgtggcctta tggttacagt   840
atgcccatcg cagttcgcta cacgcaggac gcttttttcac gttctggttg gttgtggcct   900
gttgatgcta aaggtgagcc gcttaaagc                                     929
```

<210> SEQ ID NO 88

<211> LENGTH: 87
<212> TYPE: DNA
<213> ORGANISM: Artificial Sequence
<220> FEATURE:
<223> OTHER INFORMATION: synthetic

<400> SEQUENCE: 88
gtacggggaa ggacgtcaat agtcacacag tccttgacgg tataataacc accatcatgg    60
cgaccatcca aaggataaac atcatag                                        87

<210> SEQ ID NO 89
<211> LENGTH: 136
<212> TYPE: DNA
<213> ORGANISM: Artificial Sequence
<220> FEATURE:
<223> OTHER INFORMATION: synthetic

<400> SEQUENCE: 89
gagtaaacat agtgccatgc tcaggaacaa agaaacgcgg cacagaatgt ttataggtct    60
gttgaacacg accagaaaac tggcctaacg acgtttggtc agttccatca acatcatagc   120
cagatgccca gagatt                                                   136

<210> SEQ ID NO 90
<211> LENGTH: 1126
<212> TYPE: DNA
<213> ORGANISM: Artificial Sequence
<220> FEATURE:
<223> OTHER INFORMATION: synthetic

<400> SEQUENCE: 90
atgcctgacc gtaccgaggc taaccctaat gagcttaatc aagatgatgc tcgttatggt    60
ttccgttgct gccatctcaa aaacatttgg actgctccgc ttcctcctga gactgagctt   120
tctcgccaaa tgacgacttc taccacatct attgacatta tgggtctgca agctgcttat   180
gctaatttgc atactgacca agaacgtgat tacttcatgc agcgttacca tgatgttatt   240
tcttcatttg gaggtaaaac ctcttatgac gctgacaacc gtccttact tgtcatgcgc    300 tctaatctct gggcatctgg ctatgatgtt gatggaactg accaaacgtc gttaggccag   360
ttttctggtc gtgttcaaca gacctataaa cattctgtgc cgcgtttctt tgttcctgag   420
catggcacta tgtttactct tgcgcttgtt cgttttccgc ctactgcgac taaagagatt   480
cagtacctta acgctaaagg tgctttgact tataccgata ttgctggcga ccctgttttg   540
tatggcaact gccgccgcg tgaaatttct atgaaggatg ttttccgttc tggtgattcg    600
tctaagaagt ttaagattgc tgagggtcag tggtatcgtt atgcgccttc gtatgttct    660 cctgcttatc accttcttga aggcttccca ttcattcagg aaccgccttc tggtgatttg   720
caagaacgcg tacttattcg ccaccatgat tatgaccagt gtttccagtc cgttcagttg   780
ttgcagtgga atagtcaggt taaatttaat gtgaccgttt atcgcaatct gccgaccact   840
cgcgattcaa tcatgacttc gtgataaaag attgagtgtg aggttataac gccgaagcgg   900
taaaaatttt aattttgcc gctgagggt tgaccaagcg aagcgcggta ggttttctgc    960
ttaggagttt aatcatgttt cagactttta tttctcgcca taattcaaac ttttttctg   1020 ataagctggt tctcacttct gttactccag cttcttcggc acctgtttta cagacaccta   1080
aagctacatc gtcaacgtta tattttgata gtttgacggt taatgc                 1126

<210> SEQ ID NO 91
<211> LENGTH: 674

<212> TYPE: DNA
<213> ORGANISM: Artificial Sequence
<220> FEATURE:
<223> OTHER INFORMATION: synthetic

<400> SEQUENCE: 91

| | | | | | |
|---|---|---|---|---|---|
| ctgttaacac | tactggttat | attgaccatg | ccgcttttct | tggcacgatt | aaccctgata | 60 |
| ccaataaaat | ccctaagcat | ttgtttcagg | gttatttgaa | tatctataac | aactatttta | 120 |
| aagcgccgtg | gatgcctgac | cgtaccgagg | ctaaccctaa | tgagcttaat | caagatgatg | 180 |
| ctcgttatgg | tttccgttgc | tgccatctca | aaaacatttg | gactgctccg | cttcctcctg | 240 |
| agactgagct | ttctcgccaa | atgacgactt | ctaccacatc | tattgacatt | atgggtctgc | 300 |
| aagctgctta | tgctaatttg | catactgacc | aagaacgtga | ttacttcatg | cagcgttacc | 360 |
| atgatgttat | ttcttcattt | ggaggtaaaa | cctcttatga | cgctgacaac | cgtcctttac | 420 |
| ttgtcatgcg | ctctaatctc | tgggcatctg | gctatgatgt | tgatggaact | gaccaaacgt | 480 |
| cgttaggcca | gttttctggt | cgtgttcaac | agacctataa | acattctgtg | ccgcgtttct | 540 |
| ttgttcctga | gcatggcact | atgtttactc | ttgcgcttgt | tcgttttccg | cctactgcga | 600 |
| ctaaagagat | tcagtacctt | aacgctaaag | gtgctttgac | ttataccgat | attgctggcg | 660 |
| accctgtttt | gtat | | | | | 674 |

<210> SEQ ID NO 92
<211> LENGTH: 914
<212> TYPE: DNA
<213> ORGANISM: Artificial Sequence
<220> FEATURE:
<223> OTHER INFORMATION: synthetic

<400> SEQUENCE: 92

| | | | | | |
|---|---|---|---|---|---|
| tgacagatgt | atccatctga | atgcaatgaa | gaaaaccacc | attaccagca | ttaaccgtca | 60 |
| aactatcaaa | atataacgtt | gacgatgtag | ctttaggtgt | ctgtaaaaca | ggtgccgaag | 120 |
| aagctggagt | aacagaagtg | agaaccagct | tatcagaaaa | aaagtttgaa | ttatggcgag | 180 |
| aaataaaagt | ctgaaacatg | attaaactcc | taagcagaaa | acctaccgcg | cttcgcttgg | 240 |
| tcaacccctc | agcggcaaaa | attaaaattt | ttaccgcttc | ggcgttataa | cctcacactc | 300 |
| aatcttttat | cacgaagtca | tgattgaatc | gcgagtggtc | ggcagattgc | gataaacggt | 360 |
| cacattaaat | ttaacctgac | tattccactg | caacaactga | acggactgga | aacactggtc | 420 |
| ataatcatgg | tggcgaataa | gtacgcgttc | ttgcaaatca | ccagaaggcg | gttcctgaat | 480 |
| gaatgggaag | ccttcaagaa | ggtgataagc | aggagaaaca | tacgaaggcg | cataacgata | 540 |
| ccactgaccc | tcagcaatct | taaacttctt | agacgaatca | ccagaacgga | aaacatcctt | 600 |
| catagaaatt | tcacgcggcg | gcaagttgcc | atacaaaaca | gggtcgccag | caatatcggt | 660 |
| ataagtcaaa | gcacctttag | cgttaaggta | ctgaatctct | ttagtcgcag | taggcggaaa | 720 |
| acgaacaagc | gcaagagtaa | acatagtgcc | atgctcagga | acaaagaaac | gcggcacaga | 780 |
| atgtttatag | gtctgttgaa | cacgaccaga | aaactggcct | aacgacgttt | ggtcagttcc | 840 |
| atcaacatca | tagccagatg | cccagagatt | agagcgcatg | acaagtaaag | gacggttgtc | 900 |
| agcgtcataa | gagg | | | | | 914 |

<210> SEQ ID NO 93
<211> LENGTH: 156
<212> TYPE: DNA
<213> ORGANISM: Artificial Sequence
<220> FEATURE:

<223> OTHER INFORMATION: synthetic

<400> SEQUENCE: 93

```
gcctgagtat ggtacagcta atggccgtct tcatttccat gcggtgcact ttatgcggac    60
acttcctaca ggtagcgttg accctaattt tggtcgtcgg gtacgcaatc gccgccagtt   120
aaatagcttg caaaatacgt ggccttatgg ttacag                             156
```

<210> SEQ ID NO 94
<211> LENGTH: 661
<212> TYPE: DNA
<213> ORGANISM: Artificial Sequence
<220> FEATURE:
<223> OTHER INFORMATION: synthetic

<400> SEQUENCE: 94

```
gcactatgtt tactcttgcg cttgttcgtt ttccgcctac tgcgactaaa gagattcagt    60
accttaacgc taaaggtgct ttgacttata ccgatattgc tggcgaccct gttttgtatg   120
gcaacttgcc gccgcgtgaa atttctatga aggatgtttt ccgttctggt gattcgtcta   180
agaagtttaa gattgctgag ggtcagtggt atcgttatgc gccttcgtat gtttctcctg   240
cttatcacct tcttgaaggc ttcccattca ttcaggaacc gccttctggt gatttgcaag   300
aacgcgtact tattcgccac catgattatg accagtgttt ccagtccgtt cagttgttgc   360
agtggaatag tcaggttaaa tttaatgtga ccgtttatcg caatctgccg accactcgcg   420
attcaatcat gacttcgtga taaagattg agtgtgaggt tataacgccg aagcggtaaa   480
aattttaatt tttgccgctg aggggttgac caagcgaagc gcggtaggtt ttctgcttag   540
gagtttaatc atgtttcaga cttttatttc tcgccataat tcaaactttt tttctgataa   600
gctggttctc acttctgtta ctccagcttc ttcggcacct gttttacaga cacctaaagc   660
t                                                                   661
```

<210> SEQ ID NO 95
<211> LENGTH: 680
<212> TYPE: DNA
<213> ORGANISM: Artificial Sequence
<220> FEATURE:
<223> OTHER INFORMATION: synthetic

<400> SEQUENCE: 95

```
gaaccatacg accaatatca cgaaaatagt cacgcaaagc attgggatta tcataaaacg    60
cctctaatcg gtcgtcagcc aacgtgagag tgtcaaaaac gataaaccaa ccatcagcat   120
gagcctgtcg cattgcattc atcaaacgct gaatagcaaa gcctctacgc gatttcatag   180
tggaggcctc cagcaatctt gaacactcat ccttaatacc tttcttttg gggtaattat   240
actcatcgcg aatatcctta gagggcgtt cagcagccag cttgcggcaa aactgcgtaa   300
ccgtcttctc gttctctaaa aaccattttt cgtcccttc ggggcggtgg tctatagtgt   360
tattaatatc aagttgggg agcacattgt agcattgtgc caattcatcc attaacttct   420
cagtaacaga tacaaactca tcacgaacgt cagaagcagc cttatggccg tcaacataca   480
tatcaccatt atcgaactca acgccctgca tacgaaaaga cagaatctct tccaagagct   540
tgatgcggtt atccatctgc ttatggaagc caagcattgg ggattgagaa agagtagaaa   600
tgccacaagc ctcaatagca ggtttaagag cctcgatacg ctcaaagtca aaataatcag   660
cgtgacattc agaagggtaa                                               680
```

<210> SEQ ID NO 96
<211> LENGTH: 1172
<212> TYPE: DNA
<213> ORGANISM: Artificial Sequence
<220> FEATURE:
<223> OTHER INFORMATION: synthetic

<400> SEQUENCE: 96

| | | | | | |
|---|---|---|---|---|---|
| ctcctaagca | gaaaacctac | cgcgcttcgc | ttggtcaacc | cctcagcggc | aaaaattaaa | 60 |
| attttaccg | cttcggcgtt | ataacctcac | actcaatctt | ttatcacgaa | gtcatgattg | 120 |
| aatcgcgagt | ggtcggcaga | ttgcgataaa | cggtcacatt | aaatttaacc | tgactattcc | 180 |
| actgcaacaa | ctgaacggac | tggaaacact | ggtcataatc | atggtggcga | ataagtacgc | 240 |
| gttcttgcaa | atcaccagaa | ggcggttcct | gaatgaatgg | gaagccttca | agaaggtgat | 300 |
| aagcaggaga | aacatacgaa | ggcgcataac | gataccactg | accctcagca | atcttaaact | 360 |
| tcttagacga | atcaccagaa | cggaaaacat | ccttcataga | aatttcacgc | ggcggcaagt | 420 |
| tgccatacaa | aacagggtcg | ccagcaatat | cggtataagt | caaagcacct | ttagcgttaa | 480 |
| ggtactgaat | ctctttagtc | gcagtaggcg | gaaaacgaac | aagcgcaaga | gtaaacatag | 540 |
| tgccatgctc | aggaacaaag | aaacgcggca | cagaatgttt | ataggtctgt | tgaacacgac | 600 |
| cagaaaactg | gcctaacgac | gtttggtcag | ttccatcaac | atcatagcca | gatgcccaga | 660 |
| gattagagcg | catgacaagt | aaaggacggt | tgtcagcgtc | ataagaggtt | ttacctccaa | 720 |
| atgaagaaat | aacatcatgg | taacgctgca | tgaagtaatc | acgttcttgg | tcagtatgca | 780 |
| aattagcata | agcagcttgc | agacccataa | tgtcaataga | tgtggtagaa | gtcgtcattt | 840 |
| ggcgagaaag | ctcagtctca | ggaggaagcg | gagcagtcca | aatgttttg | agatggcagc | 900 |
| aacggaaacc | ataacgagca | tcatcttgat | taagctcatt | agggttagcc | tcggtacggt | 960 |
| caggcatcca | cggcgcttta | aaatagttgt | tatagatatt | caaataaccc | tgaaacaaat | 1020 |
| gcttagggat | tttattggta | tcaggttaa | tcgtgccaag | aaaagcggca | tggtcaatat | 1080 |
| aaccagtagt | gttaacagtc | gggagaggag | tggcattaac | accatccttc | atgaacttaa | 1140 |
| tccactgttc | accataaacg | tgacgatgag | gg | | | 1172 |

<210> SEQ ID NO 97
<211> LENGTH: 851
<212> TYPE: DNA
<213> ORGANISM: Artificial Sequence
<220> FEATURE:
<223> OTHER INFORMATION: synthetic

<400> SEQUENCE: 97

| | | | | | |
|---|---|---|---|---|---|
| atatcagcac | caacagaaac | aacctgatta | gcggcgttga | cagatgtatc | catctgaatg | 60 |
| caatgaagaa | aaccaccatt | accagcatta | accgtcaaac | tatcaaaata | taacgttgac | 120 |
| gatgtagctt | taggtgtctg | taaaacaggt | gccgaagaag | ctggagtaac | agaagtgaga | 180 |
| accagcttat | cagaaaaaaa | gtttgaatta | tggcgagaaa | taaagtctg | aaacatgatt | 240 |
| aaactcctaa | gcagaaaacc | taccgcgctt | cgcttggtca | accctcagc | ggcaaaaatt | 300 |
| aaaatttta | ccgcttcggc | gttataacct | cacactcaat | cttttatcac | gaagtcatga | 360 |
| ttgaatcgcg | agtggtcggc | agattgcgat | aaacggtcac | attaaattta | acctgactat | 420 |
| tccactgcaa | caactgaacg | gactggaaac | actggtcata | atcatggtgg | cgaataagta | 480 |
| cgcgttcttg | caaatcacca | gaaggcggtt | cctgaatgaa | tgggaagcct | tcaagaaggt | 540 |
| gataagcagg | agaaacatac | gaaggcgcat | aacgatacca | ctgaccctca | gcaatcttaa | 600 |

| acttcttaga cgaatcacca gaacggaaaa catccttcat agaaatttca cgcggcggca | 660 |
| agttgccata caaaacaggg tcgccagcaa tatcggtata agtcaaagca cctttagcgt | 720 |
| taaggtactg aatctcttta gtcgcagtag gcggaaaacg aacaagcgca agagtaaaca | 780 |
| tagtgccatg ctcaggaaca agaaacgcg gcacagaatg tttataggtc tgttgaacac | 840 |
| gaccagaaaa c | 851 |

<210> SEQ ID NO 98
<211> LENGTH: 615
<212> TYPE: DNA
<213> ORGANISM: Artificial Sequence
<220> FEATURE:
<223> OTHER INFORMATION: synthetic

<400> SEQUENCE: 98

| catgattaaa ctcctaagca gaaaacctac cgcgcttcgc ttggtcaacc cctcagcggc | 60 |
| aaaaattaaa attttaccg cttcggcgtt ataacctcac actcaatctt ttatcacgaa | 120 |
| gtcatgattg aatcgcgagt ggtcggcaga ttgcgataaa cggtcacatt aaatttaacc | 180 |
| tgactattcc actgcaacaa ctgaacggac tggaaacact ggtcataatc atggtggcga | 240 |
| ataagtacgc gttcttgcaa atcaccagaa ggcggttcct gaatgaatgg gaagccttca | 300 |
| agaaggtgat aagcaggaga acatacgaa ggcgcataac gataccactg accctcagca | 360 |
| atcttaaact tcttagacga atcaccagaa cggaaaacat ccttcataga aatttcacgc | 420 |
| ggcggcaagt tgccatacaa aacagggtcg ccagcaatat cggtataagt caaagcacct | 480 |
| ttagcgttaa ggtactgaat ctctttagtc gcagtaggcg gaaaacgaac aagcgcaaga | 540 |
| gtaaacatag tgccatgctc aggaacaaag aaacgcggca gaatgtttt ataggtctgt | 600 |
| tgaacacgac cagaa | 615 |

<210> SEQ ID NO 99
<211> LENGTH: 607
<212> TYPE: DNA
<213> ORGANISM: Artificial Sequence
<220> FEATURE:
<223> OTHER INFORMATION: synthetic

<400> SEQUENCE: 99

| ttcagtacct taacgctaaa ggtgctttga cttataccga tattgctggc gaccctgttt | 60 |
| tgtatggcaa cttgccgccg cgtgaaattt ctatgaagga tgttttccgt tctggtgatt | 120 |
| cgtctaagaa gtttaagatt gctgagggtc agtggtatcg ttatgcgcct tcgtatgttt | 180 |
| ctcctgctta tcaccttctt gaaggcttcc cattcattca ggaaccgcct tctggtgatt | 240 |
| tgcaagaacg cgtacttatt cgccaccatg attatgacca gtgtttccag tccgttcagt | 300 |
| tgttgcagtg gaatagtcag gttaaattta atgtgaccgt ttatcgcaat ctgccgacca | 360 |
| ctcgcgattc aatcatgact tcgtgataaa agattgagtg tgaggttata acgccgaagc | 420 |
| ggtaaaaatt ttaattttg ccgctgaggg gttgaccaag cgaagcgcgg taggttttct | 480 |
| gcttaggagt ttaatcatgt ttcagacttt tatttctcgc cataattcaa actttttttc | 540 |
| tgataagctg gttctcactt ctgttactcc agcttcttcg gcacctgttt tacagacacc | 600 |
| taaagct | 607 |

<210> SEQ ID NO 100
<211> LENGTH: 1388
<212> TYPE: DNA
<213> ORGANISM: Artificial Sequence

```
<220> FEATURE:
<223> OTHER INFORMATION: synthetic

<400> SEQUENCE: 100
gaaacaacct gattagcggc gttgacagat gtatccatct gaatgcaatg aagaaaacca      60
ccattaccag cattaaccgt caaactatca aaatataacg ttgacgatgt agctttaggt     120
gtctgtaaaa caggtgccga agaagctgga gtaacagaag tgagaaccag cttatcagaa     180
aaaaagtttg aattatggcg agaaataaaa gtctgaaaca tgattaaact cctaagcaga     240
aaacctaccg cgcttcgctt ggtcaaccct tcagcggcaa aaattaaaat ttttaccgct     300
tcggcgttat aacctcacac tcaatctttt atcacgaagt catgattgaa tcgcgagtgg     360
tcggcagatt gcgataaacg gtcacattaa atttaacctg actattccac tgcaacaact     420
gaacggactg gaaacactgg tcataatcat ggtggcgaat aagtacgcgt tcttgcaaat     480
caccagaagg cggttcctga atgaatggga agccttcaag aaggtgataa gcaggagaaa     540
catacgaagg cgcataacga taccactgac cctcagcaat cttaaacttc ttagacgaat     600
caccagaacg gaaacatcc ttcatagaaa tttcacgcgg cggcaagttg ccatacaaaa     660
cagggtcgcc agcaatatcg gtataagtca aagcaccttt agcgttaagg tactgaatct     720
ctttagtcgc agtaggcgga aaacgaacaa gcgcaagagt aaacatagtg ccatgctcag     780
gaacaaagaa acgcggcaca gaatgtttat aggtctgttg aacacgacca gaaaactggc     840
ctaacgacgt ttggtcagtt ccatcaacat catagccaga tgcccagaga ttagagcgca     900
tgacaagtaa aggacggttg tcagcgtcat aagaggtttt acctccaaat gaagaaataa     960
catcatggta acgctgcatg aagtaatcac gttcttggtc agtatgcaaa ttagcataag    1020
cagcttgcag acccataatg tcaatagatg tggtagaagt cgtcatttgg cgagaaagct    1080
cagtctcagg aggaagcgga gcagtccaaa tgttttgag atggcagcaa cggaaaccat     1140
aacgagcatc atcttgatta agctcattag ggttagcctc ggtacggtca ggcatccacg    1200
gcgctttaaa atagttgtta tagatattca ataaccctg aaacaaatgc ttagggattt     1260
tattggtatc agggttaatc gtgccaagaa aagcggcatg gtcaatataa ccagtagtgt    1320
taacagtcgg gagaggagtg gcattaacac catccttcat gaacttaatc cactgttcac    1380
cataaacg                                                             1388

<210> SEQ ID NO 101
<211> LENGTH: 123
<212> TYPE: DNA
<213> ORGANISM: Artificial Sequence
<220> FEATURE:
<223> OTHER INFORMATION: synthetic

<400> SEQUENCE: 101
ctctttctga ttgtccagtt gcattttagt aagctctttt tgattctcaa atccggcgtc      60
aaccatacca gcagaggaag catcagcacc agcacgctcc caagcattaa gctcaggaaa     120
tgc                                                                  123

<210> SEQ ID NO 102
<211> LENGTH: 988
<212> TYPE: DNA
<213> ORGANISM: Artificial Sequence
<220> FEATURE:
<223> OTHER INFORMATION: synthetic
```

<400> SEQUENCE: 102

```
acctgattag cggcgttgac agatgtatcc atctgaatgc aatgaagaaa accaccatta      60
ccagcattaa ccgtcaaact atcaaaatat aacgttgacg atgtagcttt aggtgtctgt     120
aaaacaggtg ccgaagaagc tggagtaaca gaagtgagaa ccagcttatc agaaaaaaag     180
tttgaattat ggcgagaaat aaaagtctga acatgatta  aactcctaag cagaaaacct     240
accgcgcttc gcttggtcaa ccccctcagcg gcaaaaatta aaattttttac cgcttcggcg     300
ttataacctc acactcaatc ttttatcacg aagtcatgat tgaatcgcga gtggtcggca     360
gattgcgata acggtcaca  ttaaatttaa cctgactatt ccactgcaac aactgaacgg     420
actggaaaca ctggtcataa tcatggtggc gaataagtac gcgttcttgc aaatcaccag     480
aaggcggttc ctgaatgaat gggaagcctt caagaaggtg ataagcagga gaaacatacg     540
aaggcgcata acgataccac tgaccctcag caatcttaaa cttcttagac gaatcaccag     600
aacgaaaaac atccttcata gaaatttcac gcggcggcaa gttgccatac aaaacagggt     660
cgccagcaat atcggtataa gtcaaagcac ctttagcgtt aaggtactga atctctttag     720
tcgcagtagg cggaaaacga acaagcgcaa gagtaaacat agtgccatgc tcaggaacaa     780
agaaacgcgg cacagaatgt ttataggtct gttgaacacg accagaaaac tggcctaacg     840
acgtttggtc agttccatca acatcatagc cagatgccca gagattagag cgcatgacaa     900
gtaaaggacg gttgtcagcg tcataagagg ttttacctcc aaatgaagaa ataacatcat     960
ggtaacgctg catgaagtaa tcacgttc                                        988
```

<210> SEQ ID NO 103
<211> LENGTH: 945
<212> TYPE: DNA
<213> ORGANISM: Artificial Sequence
<220> FEATURE:
<223> OTHER INFORMATION: synthetic

<400> SEQUENCE: 103

```
atggtgaaca gtggattaag ttcatgaagg atggtgttaa tgccactcct ctcccgactg      60
ttaacactac tggttatatt gaccatgccg cttttcttgg cacgattaac cctgatacca     120
ataaaatccc taagcatttg tttcagggtt atttgaatat ctataacaac tattttaaag     180
cgccgtggat gcctgaccgt accgaggcta accctaatga gcttaatcaa gatgatgctc     240
gttatggttt ccgttgctgc catctcaaaa acatttggac tgctccgctt cctcctgaga     300
ctgagctttc tcgccaaatg acgacttcta ccacatctat tgacattatg ggtctgcaag     360
ctgcttatgc taatttgcat actgaccaag aacgtgatta cttcatgcag cgttaccatg     420
atgttatttc ttcatttgga ggtaaaacct cttatgacgc tgacaaccgt cctttacttg     480
tcatgcgctc taatctctgg gcatctggct atgatgttga tggaactgac caaacgtcgt     540
taggccagtt ttctggtcgt gttcaacaga cctataaaca ttctgtgccg cgtttctttg     600
ttcctgagca tggcactatg tttactcttg cgcttgttcg ttttccgcct actgcgacta     660
aagagattca gtaccttaac gctaaaggtg ctttgactta taccgatatt gctggcgacc     720
ctgttttgta tggcaacttg ccgccgcgtg aaatttctat gaaggatgtt ttccgttctg     780
gtgattcgtc taagaagttt aagattgctg agggtcagtg gtatcgttat gcgccttcgt     840
atgtttctcc tgcttatcac cttcttgaag gcttcccatt cattcaggaa ccgccttctg     900
gtgatttgca agaacgcgta cttattcgcc accatgatta tgacc                    945
```

<210> SEQ ID NO 104
<211> LENGTH: 333
<212> TYPE: DNA
<213> ORGANISM: Artificial Sequence
<220> FEATURE:
<223> OTHER INFORMATION: synthetic

<400> SEQUENCE: 104

```
agtgtcaaaa acgataaacc aaccatcagc atgagcctgt cgcattgcat tcatcaaacg      60
ctgaatagca aagcctctac gcgatttcat agtggaggcc tccagcaatc ttgaacactc     120
atccttaata cctttctttt tggggtaatt atactcatcg cgaatatcct taagagggcg     180
ttcagcagcc agcttgcggc aaaactgcgt aaccgtcttc tcgttctcta aaaccattt     240 ttcgtcccct tcggggcggt ggtctatagt gttattaata tcaagttggg ggagcacatt     300
gtagcattgt gccaattcat ccattaactt ctc                                  333
```

<210> SEQ ID NO 105
<211> LENGTH: 80
<212> TYPE: DNA
<213> ORGANISM: Artificial Sequence
<220> FEATURE:
<223> OTHER INFORMATION: synthetic

<400> SEQUENCE: 105

```
ggaattacta ctgcttgttt acgaattaaa tcgaagtgga ctgctggcgg aaaatgagaa      60
aattcgacct atccttgcgc                                                  80
```

<210> SEQ ID NO 106
<211> LENGTH: 59
<212> TYPE: DNA
<213> ORGANISM: Artificial Sequence
<220> FEATURE:
<223> OTHER INFORMATION: synthetic

<400> SEQUENCE: 106

```
ctgcaacaac tgaacggact ggaaacactg gtcataatca tggtggcgaa taagtacgc       59
```

<210> SEQ ID NO 107
<211> LENGTH: 223
<212> TYPE: DNA
<213> ORGANISM: Artificial Sequence
<220> FEATURE:
<223> OTHER INFORMATION: synthetic

<400> SEQUENCE: 107

```
ggcctctatt aagctcattc aggcttctgc cgtttttggat ttaaccgaag atgatttcga     60
ttttctgacg agtaacaaag tttggattgc tactgaccgc tctcgtgctc gtcgctgcgt    120
tgaggcttgc gtttatggta cgctggactt tgtaggatac cctcgctttc ctgctcctgt    180
tgagtttatt gctgccgtca ttgcttatta tgttcatccc gtc                       223
```

<210> SEQ ID NO 108
<211> LENGTH: 105
<212> TYPE: DNA
<213> ORGANISM: Artificial Sequence
<220> FEATURE:
<223> OTHER INFORMATION: synthetic

<400> SEQUENCE: 108

```
gtattgataa agctgttgcc gatacttgga acaatttctg gaaagacggt aaagctgatg      60
gtattggctc taatttgtct aggaaataac cgtcaggatt gacac                     105
```

<210> SEQ ID NO 109
<211> LENGTH: 131
<212> TYPE: DNA
<213> ORGANISM: Artificial Sequence
<220> FEATURE:
<223> OTHER INFORMATION: synthetic

<400> SEQUENCE: 109
gtttctatgt ggctaaatac gttaacaaaa agtcagatat ggaccttgct gctaaaggtc    60
taggagctaa agaatggaac aactcactaa aaaccaagct gtcgctactt cccaagaagc   120
tgttcagaat c                                                        131

<210> SEQ ID NO 110
<211> LENGTH: 40
<212> TYPE: DNA
<213> ORGANISM: Artificial Sequence
<220> FEATURE:
<223> OTHER INFORMATION: synthetic

<400> SEQUENCE: 110
accggaggcg gcttttttgac cgcctccaaa caatttagac                          40

<210> SEQ ID NO 111
<211> LENGTH: 45
<212> TYPE: DNA
<213> ORGANISM: Artificial Sequence
<220> FEATURE:
<223> OTHER INFORMATION: synthetic

<400> SEQUENCE: 111
gaagaaaacg tgcgtcaaaa attacgtgca gaaggagtga tgtaa                     45

<210> SEQ ID NO 112
<211> LENGTH: 274
<212> TYPE: DNA
<213> ORGANISM: Artificial Sequence
<220> FEATURE:
<223> OTHER INFORMATION: synthetic

<400> SEQUENCE: 112
tcgcaaggct aatgattcac acgccgactg ctatcagtat ttttgtgtgc ctgagtatgg     60
tacagctaat ggccgtcttc atttccatgc ggtgcacttt atgcggacac ttcctacagg   120
tagcgttgac cctaattttg gtcgtcgggt acgcaatcgc cgccagttaa atagcttgca   180
aaatacgtgg ccttatggtt acagtatgcc catcgcagtt cgctacacgc aggacgcttt   240
ttcacgttct ggttggttgt ggcctgttga tgct                               274

<210> SEQ ID NO 113
<211> LENGTH: 96
<212> TYPE: DNA
<213> ORGANISM: Artificial Sequence
<220> FEATURE:
<223> OTHER INFORMATION: synthetic

<400> SEQUENCE: 113
gttacgcagt tttgccgcaa gctggctgct gaacgccctc ttaaggatat tcgcgatgag     60
tataattacc ccaaaaagaa aggtattaag gatgag                              96

<210> SEQ ID NO 114
<211> LENGTH: 50
<212> TYPE: DNA

```
<213> ORGANISM: Artificial Sequence
<220> FEATURE:
<223> OTHER INFORMATION: synthetic

<400> SEQUENCE: 114
gccataccgc tgattctgcg tttgctgatg aactaagtca acctcagcac          50

<210> SEQ ID NO 115
<211> LENGTH: 179
<212> TYPE: DNA
<213> ORGANISM: Artificial Sequence
<220> FEATURE:
<223> OTHER INFORMATION: synthetic

<400> SEQUENCE: 115
ctttagctcc tagacccttta gcagcaaggt ccatatctga cttttttgtta acgtatttag    60 ccacatagaa accaacagcc atataactgg tagctttaag cggctcacct ttagcatcaa    120
caggccacaa ccaaccagaa cgtgaaaaag cgtcctgcgt gtagcgaact gcgatgggc     179

<210> SEQ ID NO 116
<211> LENGTH: 198
<212> TYPE: DNA
<213> ORGANISM: Artificial Sequence
<220> FEATURE:
<223> OTHER INFORMATION: synthetic

<400> SEQUENCE: 116
ccagcagagg aagcatcagc accagcacgc tcccaagcat taagctcagg aaatgcagca    60
gcaagataat cacgagtatc ctttccttta tcagcggcag acttgccacc aagtccaacc    120
aaatcaagca acttatcaga acggcagaa gtgccagcct gcaacgtacc ttcaagaagt      180
cctttaccag ctttagcc                                                 198

<210> SEQ ID NO 117
<211> LENGTH: 122
<212> TYPE: DNA
<213> ORGANISM: Artificial Sequence
<220> FEATURE:
<223> OTHER INFORMATION: synthetic

<400> SEQUENCE: 117
acattcagaa gggtaataag aacgaaccat aaaaaagcct ccaagatttg gaggcatgaa    60
aacatacaat tgggagggtg tcaatcctga cggttatttc ctagacaaat tagagccaat    120
ac                                                                 122

<210> SEQ ID NO 118
<211> LENGTH: 318
<212> TYPE: DNA
<213> ORGANISM: Artificial Sequence
<220> FEATURE:
<223> OTHER INFORMATION: synthetic

<400> SEQUENCE: 118
gagcttaatc aagatgatgc tcgttatggt ttccgttgct gccatctcaa aaacatttgg    60
actgctccgc ttcctcctga gactgagctt tctcgccaaa tgacgacttc taccacatct    120
attgacatta tgggtctgca agctgcttat gctaatttgc atactgacca agaacgtgat    180
tacttcatgc agcgttacca tgatgttatt tcttcatttg gaggtaaaac ctcttatgac    240
gctgacaacc gtccttttact tgtcatgcgc tctaatctct gggcatctgg ctatgatgtt    300
gatggaactg accaaaacg                                                318
```

<210> SEQ ID NO 119
<211> LENGTH: 85
<212> TYPE: DNA
<213> ORGANISM: Artificial Sequence
<220> FEATURE:
<223> OTHER INFORMATION: synthetic

<400> SEQUENCE: 119
ctgttttgta tggcaacttg ccgccgcgtg aaatttctat gaaggatgtt ttccgttctg    60
gtgattcgtc taagaagttt aagat    85

<210> SEQ ID NO 120
<211> LENGTH: 130
<212> TYPE: DNA
<213> ORGANISM: Artificial Sequence
<220> FEATURE:
<223> OTHER INFORMATION: synthetic

<400> SEQUENCE: 120
atactcaggc acacaaaaat actgatagca gtcggcgtgt gaatcattag ccttgcgacc    60
ctcggcagca agaaccatac gaccaatatc acgaaaatag tcacgcaaag cattgggatt   120
atcataaaac   130

<210> SEQ ID NO 121
<211> LENGTH: 361
<212> TYPE: DNA
<213> ORGANISM: Artificial Sequence
<220> FEATURE:
<223> OTHER INFORMATION: synthetic

<400> SEQUENCE: 121
gatatggacc ttgctgctaa aggtctagga gctaaagaat ggaacaactc actaaaaacc    60
aagctgtcgc tacttcccaa gaagctgttc agaatcagaa tgagccgcaa cttcgggatg   120
aaaatgctca caatgacaaa tctgtccacg gagtgcttaa tccaacttac caagctgggt   180
tacgacgcga cgccgttcaa ccagatattg aagcagaacg caaaagaga gatgagattg   240 aggctgggaa aagttactgt agccgacgtt ttggcggcgc aacctgtgac acaaatctg    300 ctcaaattta tgcgcgcttc gataaaaatg attggcgtat ccaacctgca gagttttatc   360
g    361

<210> SEQ ID NO 122
<211> LENGTH: 308
<212> TYPE: DNA
<213> ORGANISM: Artificial Sequence
<220> FEATURE:
<223> OTHER INFORMATION: synthetic

<400> SEQUENCE: 122
tacgtggcct tatggttaca gtatgcccat cgcagttcgc tacacgcagg acgctttttc    60
acgttctggt tggttgtggc ctgttgatgc taaaggtgag ccgcttaaag ctaccagtta   120
tatggctgtt ggtttctatg tggctaaata cgttaacaaa aagtcagata tggaccttgc   180
tgctaaaggt ctaggagcta agaatggaa caactcacta aaaaccaagc tgtcgctact   240
tcccaagaag ctgttcagaa tcagaatgag ccgcaacttc gggatgaaaa tgctcacaat   300
gacaaatc    308

<210> SEQ ID NO 123

```
<211> LENGTH: 360
<212> TYPE: DNA
<213> ORGANISM: Artificial Sequence
<220> FEATURE:
<223> OTHER INFORMATION: synthetic

<400> SEQUENCE: 123
caagtaaagg acggttgtca gcgtcataag aggttttacc tccaaatgaa gaaataacat    60
catggtaacg ctgcatgaag taatcacgtt cttggtcagt atgcaaatta gcataagcag   120
cttgcagacc cataatgtca atagatgtgg tagaagtcgt catttggcga gaaagctcag   180
tctcaggagg aagcggagca gtccaaatgt ttttgagatg gcagcaacgg aaaccataac   240
gagcatcatc ttgattaagc tcattagggt tagcctcggt acggtcaggc atccacggcg   300
ctttaaaata gttgttatag atattcaaat aaccctgaaa caaatgctta gggatttat    360

<210> SEQ ID NO 124
<211> LENGTH: 49
<212> TYPE: DNA
<213> ORGANISM: Artificial Sequence
<220> FEATURE:
<223> OTHER INFORMATION: synthetic

<400> SEQUENCE: 124
ttttcatccc gaagttgcgg ctcattctga ttctgaacag cttcttggg               49

<210> SEQ ID NO 125
<211> LENGTH: 77
<212> TYPE: DNA
<213> ORGANISM: Artificial Sequence
<220> FEATURE:
<223> OTHER INFORMATION: synthetic

<400> SEQUENCE: 125
ggcaagttgc catacaaaac agggtcgcca gcaatatcgg tataagtcaa agcaccttta    60
gcgttaaggt actgaat                                                  77

<210> SEQ ID NO 126
<211> LENGTH: 44
<212> TYPE: DNA
<213> ORGANISM: Artificial Sequence
<220> FEATURE:
<223> OTHER INFORMATION: synthetic

<400> SEQUENCE: 126
tatcagaaac ggcagaagtg ccagcctgca acgtaccttc aaga                    44

<210> SEQ ID NO 127
<211> LENGTH: 72
<212> TYPE: DNA
<213> ORGANISM: Artificial Sequence
<220> FEATURE:
<223> OTHER INFORMATION: synthetic

<400> SEQUENCE: 127
gtatggtaca gctaatggcc gtcttcattt ccatgcggtg cactttatgc ggacacttcc    60
tacaggtagc gt                                                       72

<210> SEQ ID NO 128
<211> LENGTH: 86
<212> TYPE: DNA
<213> ORGANISM: Artificial Sequence
<220> FEATURE:
<223> OTHER INFORMATION: synthetic
```

<400> SEQUENCE: 128
cgcaaggtaa acgcgaacaa ttcagcggct ttaaccggac gctcgacgcc attaataatg    60 tttccgtaa attcagcgcc ttccat    86

<210> SEQ ID NO 129
<211> LENGTH: 71
<212> TYPE: DNA
<213> ORGANISM: Artificial Sequence
<220> FEATURE:
<223> OTHER INFORMATION: synthetic

<400> SEQUENCE: 129
agctggttct cacttctgtt actccagctt cttcggcacc tgttttacag acacctaaag    60
ctacatcgtc a    71

<210> SEQ ID NO 130
<211> LENGTH: 138
<212> TYPE: DNA
<213> ORGANISM: Artificial Sequence
<220> FEATURE:
<223> OTHER INFORMATION: synthetic

<400> SEQUENCE: 130
taattgcagg ggcttcggcc ccttacttga ggataaatta tgtctaatat tcaaactggc    60
gccgagcgta tgccgcatga cctttcccat cttggcttcc ttgctggtca gattggtcgt   120
cttattacca tttcaact    138

<210> SEQ ID NO 131
<211> LENGTH: 94
<212> TYPE: DNA
<213> ORGANISM: Artificial Sequence
<220> FEATURE:
<223> OTHER INFORMATION: synthetic

<400> SEQUENCE: 131
ttcctgagct taatgcttgg gagcgtgctg gtgctgatgc ttcctctgct ggtatggttg    60
acgccggatt tgagaatcaa aaagagctta ctaa    94

<210> SEQ ID NO 132
<211> LENGTH: 59
<212> TYPE: DNA
<213> ORGANISM: Artificial Sequence
<220> FEATURE:
<223> OTHER INFORMATION: synthetic

<400> SEQUENCE: 132
cttcggggcg gtggtctata gtgttattaa tatcaagttg ggggagcaca ttgtagcat    59

<210> SEQ ID NO 133
<211> LENGTH: 111
<212> TYPE: DNA
<213> ORGANISM: Artificial Sequence
<220> FEATURE:
<223> OTHER INFORMATION: synthetic

<400> SEQUENCE: 133
gttatagata ttcaaataac cctgaaacaa atgcttaggg attttattgg tatcagggtt    60
aatcgtgcca agaaaagcgg catggtcaat ataaccagta gtgttaacag t    111

<210> SEQ ID NO 134

<211> LENGTH: 354
<212> TYPE: DNA
<213> ORGANISM: Artificial Sequence
<220> FEATURE:
<223> OTHER INFORMATION: synthetic

<400> SEQUENCE: 134

```
gtcaaggact gtgtgactat tgacgtcctt ccccgtacgc cgggcaataa tgtttatgtt      60
ggtttcatgg tttggtctaa ctttaccgct actaaatgcc gcggattggt ttcgctgaat     120
caggttatta aagagattat ttgtctccag ccacttaagt gaggtgattt atgtttggtg     180
ctattgctgg cggtattgct tctgctcttg ctggtggcgc catgtctaaa ttgtttggag     240
gcggtcaaaa agccgcctcc ggtggcattc aaggtgatgt gcttgctacc gataacaata     300
ctgtaggcat gggtgatgct ggtattaaat ctgccattca aggctctaat gttc           354
```

<210> SEQ ID NO 135
<211> LENGTH: 278
<212> TYPE: DNA
<213> ORGANISM: Artificial Sequence
<220> FEATURE:
<223> OTHER INFORMATION: synthetic

<400> SEQUENCE: 135

```
gaacggaaaa catccttcat agaaatttca cgcggcggca agttgccata caaaacaggg      60
tcgccagcaa tatcggtata agtcaaagca ccttagcgt taaggtactg aatctcttta     120
gtcgcagtag gcggaaaacg aacaagcgca agagtaaaca tagtgccatg ctcaggaaca     180
aagaaacgcg gcacagaatg tttataggtc tgttgaacac gaccagaaaa ctggcctaac     240
gacgtttggt cagttccatc aacatcatag ccagatgc                              278
```

<210> SEQ ID NO 136
<211> LENGTH: 68
<212> TYPE: DNA
<213> ORGANISM: Artificial Sequence
<220> FEATURE:
<223> OTHER INFORMATION: synthetic

<400> SEQUENCE: 136

```
gtcaaaaacg ataaaccaac catcagcatg agcctgtcgc attgcattca tcaaacgctg      60
aatagcaa                                                               68
```

<210> SEQ ID NO 137
<211> LENGTH: 171
<212> TYPE: DNA
<213> ORGANISM: Artificial Sequence
<220> FEATURE:
<223> OTHER INFORMATION: synthetic

<400> SEQUENCE: 137

```
ttattatacc gtcaaggact gtgtgactat tgacgtcctt ccccgtacgc cgggcaataa      60
tgtttatgtt ggtttcatgg tttggtctaa ctttaccgct actaaatgcc gcggattggt     120
ttcgctgaat caggttatta aagagattat ttgtctccag ccacttaagt g              171
```

<210> SEQ ID NO 138
<211> LENGTH: 67
<212> TYPE: DNA
<213> ORGANISM: Artificial Sequence
<220> FEATURE:
<223> OTHER INFORMATION: synthetic

<400> SEQUENCE: 138

| | |
|---|---|
| ttcctgctcc tgttgagttt attgctgccg tcattgctta ttatgttcat cccgtcaaca | 60 |
| ttcaaac | 67 |

<210> SEQ ID NO 139
<211> LENGTH: 223
<212> TYPE: DNA
<213> ORGANISM: Artificial Sequence
<220> FEATURE:
<223> OTHER INFORMATION: synthetic

<400> SEQUENCE: 139

| | |
|---|---|
| agccagcttg cggcaaaact gcgtaaccgt cttctcgttc tctaaaaacc atttttcgtc | 60 |
| cccttcgggg cggtggtcta tagtgttatt aatatcaagt ggggagca cattgtagca | 120 |
| tgtgccaat tcatccatta acttctcagt aacagataca aactcatcac gaacgtcaga | 180 |
| agcagcctta tggccgtcaa catacatatc accattatcg aac | 223 |

<210> SEQ ID NO 140
<211> LENGTH: 270
<212> TYPE: DNA
<213> ORGANISM: Artificial Sequence
<220> FEATURE:
<223> OTHER INFORMATION: synthetic

<400> SEQUENCE: 140

| | |
|---|---|
| gtgactattg acgtccttcc ccgtacgccg ggcaataatg tttatgttgg tttcatggtt | 60 |
| tggtctaact ttaccgctac taaatgccgc ggattggttt cgctgaatca ggttattaaa | 120 |
| gagattattt gtctccagcc acttaagtga ggtgatttat gtttggtgct attgctggcg | 180 |
| gtattgcttc tgctcttgct ggtggcgcca tgtctaaatt gtttggaggc ggtcaaaaag | 240 |
| ccgcctccgg tggcattcaa ggtgatgtgc | 270 |

<210> SEQ ID NO 141
<211> LENGTH: 181
<212> TYPE: DNA
<213> ORGANISM: Artificial Sequence
<220> FEATURE:
<223> OTHER INFORMATION: synthetic

<400> SEQUENCE: 141

| | |
|---|---|
| ggtaaaacct cttatgacgc tgacaaccgt cctttacttg tcatgcgctc taatctctgg | 60 |
| gcatctggct atgatgttga tggaactgac caaacgtcgt taggccagtt ttctggtcgt | 120 |
| gttcaacaga cctataaaca ttctgtgccg cgtttctttg ttcctgagca tggcactatg | 180 |
| t | 181 |

<210> SEQ ID NO 142
<211> LENGTH: 54
<212> TYPE: DNA
<213> ORGANISM: Artificial Sequence
<220> FEATURE:
<223> OTHER INFORMATION: synthetic

<400> SEQUENCE: 142

| | |
|---|---|
| aaggacttct tgaaggtacg ttgcaggctg gcacttctgc cgtttctgat aagt | 54 |

<210> SEQ ID NO 143
<211> LENGTH: 138
<212> TYPE: DNA

```
<213> ORGANISM: Artificial Sequence
<220> FEATURE:
<223> OTHER INFORMATION: synthetic

<400> SEQUENCE: 143
gttaaatagc ttgcaaaata cgtggcctta tggttacagt atgcccatcg cagttcgcta      60
cacgcaggac gctttttcac gttctggttg gttgtggcct gttgatgcta aaggtgagcc     120
gcttaaagct accagtta                                                   138

<210> SEQ ID NO 144
<211> LENGTH: 534
<212> TYPE: DNA
<213> ORGANISM: Artificial Sequence
<220> FEATURE:
<223> OTHER INFORMATION: synthetic

<400> SEQUENCE: 144
acgctacctg taggaagtgt ccgcataaag tgcaccgcat ggaaatgaag acggccatta      60
gctgtaccat actcaggcac acaaaaatac tgatagcagt cggcgtgtga atcattagcc    120
ttgcgaccct cggcagcaag aaccatacga ccaatatcac gaaaatagtc acgcaaagca    180
ttgggattat cataaaacgc ctctaatcgg tcgtcagcca acgtgagagt gtcaaaaacg    240
ataaaccaac catcagcatg agcctgtcgc attgcattca tcaaacgctg aatagcaaag    300
cctctacgcg atttcatagt ggaggcctcc agcaatcttg aacactcatc cttaatacct    360 ttcttttttgg ggtaattata ctcatcgcga atatccttaa gagggcgttc agcagccagc    420
ttgcggcaaa actgcgtaac cgtcttctcg ttctctaaaa accattttc gtccccttcg     480 gggcggtggt ctatagtgtt attaatatca agttgggga gcacattgta gcat            534

<210> SEQ ID NO 145
<211> LENGTH: 150
<212> TYPE: DNA
<213> ORGANISM: Artificial Sequence
<220> FEATURE:
<223> OTHER INFORMATION: synthetic

<400> SEQUENCE: 145
aacaggccac aaccaaccag aacgtgaaaa agcgtcctgc gtgtagcgaa ctgcgatggg      60
catactgtaa ccataaggcc acgtattttg caagctattt aactggcggc gattgcgtac    120
ccgacgacca aaattagggt caacgctacc                                      150

<210> SEQ ID NO 146
<211> LENGTH: 170
<212> TYPE: DNA
<213> ORGANISM: Artificial Sequence
<220> FEATURE:
<223> OTHER INFORMATION: synthetic

<400> SEQUENCE: 146
agtttggatt gctactgacc gctctcgtgc tcgtcgctgc gttgaggctt gcgtttatgg      60
tacgctggac tttgtaggat accctcgctt tcctgctcct gttgagttta ttgctgccgt    120
cattgcttat tatgttcatc ccgtcaacat tcaaacggcc tgtctcatca                170

<210> SEQ ID NO 147
<211> LENGTH: 340
<212> TYPE: DNA
<213> ORGANISM: Artificial Sequence
<220> FEATURE:
<223> OTHER INFORMATION: synthetic
```

<400> SEQUENCE: 147

```
cgataccact gaccctcagc aatcttaaac ttcttagacg aatcaccaga acggaaaaca    60
tccttcatag aaatttcacg cggcggcaag ttgccataca aaacagggtc gccagcaata   120
tcggtataag tcaaagcacc tttagcgtta aggtactgaa tctctttagt cgcagtaggc   180
ggaaaacgaa caagcgcaag agtaaacata gtgccatgct caggaacaaa gaaacgcggc   240
acagaatgtt tataggtctg ttgaacacga ccagaaaact ggcctaacga cgtttggtca   300
gttccatcaa catcatagcc agatgcccag agattagagc                         340
```

<210> SEQ ID NO 148
<211> LENGTH: 124
<212> TYPE: DNA
<213> ORGANISM: Artificial Sequence
<220> FEATURE:
<223> OTHER INFORMATION: synthetic

<400> SEQUENCE: 148

```
ggcttccata agcagatgga taaccgcatc aagctcttgg aagagattct gtcttttcgt    60
atgcagggcg ttgagttcga taatggtgat atgtatgttg acggccataa ggctgcttct   120
gacg                                                               124
```

<210> SEQ ID NO 149
<211> LENGTH: 69
<212> TYPE: DNA
<213> ORGANISM: Artificial Sequence
<220> FEATURE:
<223> OTHER INFORMATION: synthetic

<400> SEQUENCE: 149

```
atccttaaga gggcgttcag cagccagctt gcggcaaaac tgcgtaaccg tcttctcgtt    60
ctctaaaaa                                                           69
```

<210> SEQ ID NO 150
<211> LENGTH: 49
<212> TYPE: DNA
<213> ORGANISM: Artificial Sequence
<220> FEATURE:
<223> OTHER INFORMATION: synthetic

<400> SEQUENCE: 150

```
atcttgctgc tgcatttcct gagcttaatg cttgggagcg tgctggtgc                49
```

<210> SEQ ID NO 151
<211> LENGTH: 60
<212> TYPE: DNA
<213> ORGANISM: Artificial Sequence
<220> FEATURE:
<223> OTHER INFORMATION: synthetic

<400> SEQUENCE: 151

```
gccattagct gtaccatact caggcacaca aaaatactga tagcagtcgg cgtgtgaatc    60
```

<210> SEQ ID NO 152
<211> LENGTH: 236
<212> TYPE: DNA
<213> ORGANISM: Artificial Sequence
<220> FEATURE:
<223> OTHER INFORMATION: synthetic

<400> SEQUENCE: 152

```
ttgccataca aaacagggtc gccagcaata tcggtataag tcaaagcacc tttagcgtta    60
aggtactgaa tctctttagt cgcagtaggc ggaaaacgaa caagcgcaag agtaaacata   120
gtgccatgct caggaacaaa gaaacgcggc acagaatgtt tataggtctg ttgaacacga   180
ccagaaaact ggcctaacga cgtttggtca gttccatcaa catcatagcc agatgc       236
```

<210> SEQ ID NO 153
<211> LENGTH: 78
<212> TYPE: DNA
<213> ORGANISM: Artificial Sequence
<220> FEATURE:
<223> OTHER INFORMATION: synthetic

<400> SEQUENCE: 153

```
aatgttgacg ggatgaacat aataagcaat gacggcagca ataaactcaa caggagcagg    60
aaagcgaggg tatcctac                                                  78
```

<210> SEQ ID NO 154
<211> LENGTH: 114
<212> TYPE: DNA
<213> ORGANISM: Artificial Sequence
<220> FEATURE:
<223> OTHER INFORMATION: synthetic

<400> SEQUENCE: 154

```
ctaaaggtgc tttgacttat accgatattg ctggcgaccc tgttttgtat ggcaacttgc    60
cgccgcgtga aatttctatg aaggatgttt ccgttctgg tgattcgtct aaga          114
```

<210> SEQ ID NO 155
<211> LENGTH: 99
<212> TYPE: DNA
<213> ORGANISM: Artificial Sequence
<220> FEATURE:
<223> OTHER INFORMATION: synthetic

<400> SEQUENCE: 155

```
atccatctga atgcaatgaa gaaaaccacc attaccagca ttaaccgtca aactatcaaa    60
atataacgtt gacgatgtag ctttaggtgt ctgtaaaac                           99
```

<210> SEQ ID NO 156
<211> LENGTH: 273
<212> TYPE: DNA
<213> ORGANISM: Artificial Sequence
<220> FEATURE:
<223> OTHER INFORMATION: synthetic

<400> SEQUENCE: 156

```
cagttgttgc agtggaatag tcaggttaaa tttaatgtga ccgtttatcg caatctgccg    60
accactcgcg attcaatcat gacttcgtga taaagattg agtgtgaggt tataacgccg    120
aagcggtaaa aatttttaatt tttgccgctg aggggttgac caagcgaagc gcggtaggtt  180
ttctgcttag gagtttaatc atgtttcaga cttttatttc tcgccataat tcaaactttt   240
tttctgataa gctggttctc acttctgtta ctc                                273
```

<210> SEQ ID NO 157
<211> LENGTH: 72
<212> TYPE: DNA
<213> ORGANISM: Artificial Sequence
<220> FEATURE:

<223> OTHER INFORMATION: synthetic

<400> SEQUENCE: 157
cattgtagca ttgtgccaat tcatccatta acttctcagt aacagataca aactcatcac    60
gaacgtcaga ag    72

<210> SEQ ID NO 158
<211> LENGTH: 62
<212> TYPE: DNA
<213> ORGANISM: Artificial Sequence
<220> FEATURE:
<223> OTHER INFORMATION: synthetic

<400> SEQUENCE: 158
taatttatcc tcaagtaagg ggccgaagcc cctgcaatta aaattgttga ccacctacat    60
ac    62

<210> SEQ ID NO 159
<211> LENGTH: 314
<212> TYPE: DNA
<213> ORGANISM: Artificial Sequence
<220> FEATURE:
<223> OTHER INFORMATION: synthetic

<400> SEQUENCE: 159
gggccgaagc ccctgcaatt aaaattgttg accacctaca taccaaagac gagcgccttt    60
acgcttgcct ttagtacctc gcaacggctg cggacgacca gggcgagcgc cagaacgttt   120 tttacccttta gacattacat cactccttct gcacgtaatt tttgacgcac gttttcttct   180
gcgtcagtaa gaacgtcagt gtttcctgcg cgtacacgca aggtaaacgc gaacaattca   240
gcggctttaa ccggacgctc gacgccatta ataatgtttt ccgtaaattc agcgccttcc   300
atgatgagac aggc    314

<210> SEQ ID NO 160
<211> LENGTH: 33
<212> TYPE: DNA
<213> ORGANISM: Artificial Sequence
<220> FEATURE:
<223> OTHER INFORMATION: synthetic

<400> SEQUENCE: 160
ggttcgttct tattaccctt ctgaatgtca cgc    33

<210> SEQ ID NO 161
<211> LENGTH: 219
<212> TYPE: DNA
<213> ORGANISM: Artificial Sequence
<220> FEATURE:
<223> OTHER INFORMATION: synthetic

<400> SEQUENCE: 161
gcttatcacc ttcttgaagg cttcccattc attcaggaac cgccttctgg tgatttgcaa    60
gaacgcgtac ttattcgcca ccatgattat gaccagtgtt tccagtccgt tcagttgttg   120
cagtggaata gtcaggttaa atttaatgtg accgtttatc gcaatctgcc gaccactcgc   180
gattcaatca tgacttcgtg ataaaagatt gagtgtgag    219

<210> SEQ ID NO 162
<211> LENGTH: 209
<212> TYPE: DNA
<213> ORGANISM: Artificial Sequence
<220> FEATURE:
<223> OTHER INFORMATION: synthetic

<400> SEQUENCE: 162

```
accaacagcc atataactgg tagctttaag cggctcacct ttagcatcaa caggccacaa    60
ccaaccagaa cgtgaaaaag cgtcctgcgt gtagcgaact gcgatgggca tactgtaacc   120
ataaggccac gtattttgca agctatttaa ctggcggcga ttgcgtaccc gacgaccaaa   180
attagggtca acgctacctg taggaagtg                                     209
```

<210> SEQ ID NO 163
<211> LENGTH: 45
<212> TYPE: DNA
<213> ORGANISM: Artificial Sequence
<220> FEATURE:
<223> OTHER INFORMATION: synthetic

<400> SEQUENCE: 163

```
atcaacatca tagccagatg cccagagatt agagcgcatg acaag                    45
```

<210> SEQ ID NO 164
<211> LENGTH: 87
<212> TYPE: DNA
<213> ORGANISM: Artificial Sequence
<220> FEATURE:
<223> OTHER INFORMATION: synthetic

<400> SEQUENCE: 164

```
ctcatctctc tttttgcgtt ctgcttcaat atctggttga acggcgtcgc gtcgtaaccc    60
agcttggtaa gttggattaa gcactcc                                        87
```

<210> SEQ ID NO 165
<211> LENGTH: 100
<212> TYPE: DNA
<213> ORGANISM: Artificial Sequence
<220> FEATURE:
<223> OTHER INFORMATION: synthetic

<400> SEQUENCE: 165

```
gtccgcagcc gttgcgaggt actaaaggca agcgtaaagg cgctcgtctt tggtatgtag    60
gtggtcaaca attttaattg cagggcttc ggccccttac                          100
```

<210> SEQ ID NO 166
<211> LENGTH: 223
<212> TYPE: DNA
<213> ORGANISM: Artificial Sequence
<220> FEATURE:
<223> OTHER INFORMATION: synthetic

<400> SEQUENCE: 166

```
tctggctatg atgttgatgg aactgaccaa acgtcgttag gccagttttc tggtcgtgtt    60
caacagacct ataacattc tgtgccgcgt ttctttgttc ctgagcatgg cactatgttt   120
actcttgcgc ttgttcgttt tccgcctact gcgactaaag agattcagta ccttaacgct   180
aaaggtgctt tgacttatac cgatattgct ggcgaccctg ttt                     223
```

<210> SEQ ID NO 167
<211> LENGTH: 64
<212> TYPE: DNA
<213> ORGANISM: Artificial Sequence
<220> FEATURE:
<223> OTHER INFORMATION: synthetic

<400> SEQUENCE: 167
ggcatgaaaa catacaattg ggagggtgtc aatcctgacg gttatttcct agacaaatta    60
gagc    64

<210> SEQ ID NO 168
<211> LENGTH: 188
<212> TYPE: DNA
<213> ORGANISM: Artificial Sequence
<220> FEATURE:
<223> OTHER INFORMATION: synthetic

<400> SEQUENCE: 168
gaatgtttat aggtctgttg aacacgacca gaaaactggc ctaacgacgt ttggtcagtt    60
ccatcaacat catagccaga tgcccagaga ttagagcgca tgacaagtaa aggacggttg   120
tcagcgtcat aagaggtttt acctccaaat gaagaaataa catcatggta acgctgcatg   180
aagtaatc    188

<210> SEQ ID NO 169
<211> LENGTH: 217
<212> TYPE: DNA
<213> ORGANISM: Artificial Sequence
<220> FEATURE:
<223> OTHER INFORMATION: synthetic

<400> SEQUENCE: 169
aattagcata agcagcttgc agacccataa tgtcaataga tgtggtagaa gtcgtcattt    60
ggcgagaaag ctcagtctca ggaggaagcg gagcagtcca aatgttttg agatggcagc   120 aacggaaacc ataacgagca tcatcttgat taagctcatt agggttagcc tcggtacggt   180
caggcatcca cggcgcttta aaatagttgt tatagat    217

<210> SEQ ID NO 170
<211> LENGTH: 236
<212> TYPE: DNA
<213> ORGANISM: Artificial Sequence
<220> FEATURE:
<223> OTHER INFORMATION: synthetic

<400> SEQUENCE: 170
ccccaatgct tggcttccat aagcagatgg ataaccgcat caagctcttg gaagagattc    60
tgtcttttcg tatgcagggc gttgagttcg ataatggtga tatgtatgtt gacggccata   120
aggctgcttc tgacgttcgt gatgagtttt tatctgttac tgagaagtta atggatgaat   180
tggcacaatg ctacaatgtg ctcccccaac ttgatattaa taacactata gaccac    236

<210> SEQ ID NO 171
<211> LENGTH: 140
<212> TYPE: DNA
<213> ORGANISM: Artificial Sequence
<220> FEATURE:
<223> OTHER INFORMATION: synthetic

<400> SEQUENCE: 171
ccttaagagg gcgttcagca gccagcttgc ggcaaaactg cgtaaccgtc ttctcgttct    60
ctaaaaacca tttttcgtcc ccttcggggc ggtggtctat agtgttatta atatcaagtt   120
gggggagcac attgtagcat    140

<210> SEQ ID NO 172
<211> LENGTH: 80

<212> TYPE: DNA
<213> ORGANISM: Artificial Sequence
<220> FEATURE:
<223> OTHER INFORMATION: synthetic

<400> SEQUENCE: 172
gtttcagggt tatttgaata tctataacaa ctattttaaa gcgccgtgga tgcctgaccg    60
taccgaggct aaccctaatg                                                80

<210> SEQ ID NO 173
<211> LENGTH: 61
<212> TYPE: DNA
<213> ORGANISM: Artificial Sequence
<220> FEATURE:
<223> OTHER INFORMATION: synthetic

<400> SEQUENCE: 173
gggtcagtgg tatcgttatg cgccttcgta tgtttctcct gcttatcacc ttcttgaagg    60
c                                                                    61

<210> SEQ ID NO 174
<211> LENGTH: 132
<212> TYPE: DNA
<213> ORGANISM: Artificial Sequence
<220> FEATURE:
<223> OTHER INFORMATION: synthetic

<400> SEQUENCE: 174
gaactgacca acgtcgtta ggccagtttt ctggtcgtgt tcaacagacc tataaacatt     60
ctgtgccgcg tttctttgtt cctgagcatg gcactatgtt tactcttgcg cttgttcgtt   120
ttccgcctac tg                                                       132

<210> SEQ ID NO 175
<211> LENGTH: 100
<212> TYPE: DNA
<213> ORGANISM: Artificial Sequence
<220> FEATURE:
<223> OTHER INFORMATION: synthetic

<400> SEQUENCE: 175
catcagggtt aggaacatta gagccttgaa tggcagattt aataccagca tcacccatgc    60
ctacagtatt gttatcggta gcaagcacat caccttgaat                         100

<210> SEQ ID NO 176
<211> LENGTH: 120
<212> TYPE: DNA
<213> ORGANISM: Artificial Sequence
<220> FEATURE:
<223> OTHER INFORMATION: synthetic

<400> SEQUENCE: 176
cccgtacgcc gggcaataat gtttatgttg gtttcatggt ttggtctaac tttaccgcta    60
ctaaatgccg cggattggtt tcgctgaatc aggttattaa agagattatt tgtctccagc   120

<210> SEQ ID NO 177
<211> LENGTH: 68
<212> TYPE: DNA
<213> ORGANISM: Artificial Sequence
<220> FEATURE:
<223> OTHER INFORMATION: synthetic

<400> SEQUENCE: 177
ttcttcattt ggaggtaaaa cctcttatga cgctgacaac cgtcctttac ttgtcatgcg    60
ctctaatc                                                            68

<210> SEQ ID NO 178
<211> LENGTH: 148
<212> TYPE: DNA
<213> ORGANISM: Artificial Sequence
<220> FEATURE:
<223> OTHER INFORMATION: synthetic

<400> SEQUENCE: 178
aggtctagga gctaaagaat ggaacaactc actaaaaacc aagctgtcgc tacttcccaa    60
gaagctgttc agaatcagaa tgagccgcaa cttcgggatg aaaatgctca caatgacaaa   120
tctgtccacg gagtgcttaa tccaactt                                     148

<210> SEQ ID NO 179
<211> LENGTH: 57
<212> TYPE: DNA
<213> ORGANISM: Artificial Sequence
<220> FEATURE:
<223> OTHER INFORMATION: synthetic

<400> SEQUENCE: 179
gacttggtgg caagtctgcc gctgataaag gaaaggatac tcgtgattat cttgctg       57

<210> SEQ ID NO 180
<211> LENGTH: 157
<212> TYPE: DNA
<213> ORGANISM: Artificial Sequence
<220> FEATURE:
<223> OTHER INFORMATION: synthetic

<400> SEQUENCE: 180
gtccatatct gacttttgt taacgtattt agccacatag aaaccaacag ccatataact     60
ggtagcttta agcggctcac ctttagcatc aacaggccac aaccaaccag aacgtgaaaa   120
agcgtcctgc gtgtagcgaa ctgcgatggg catactg                           157

<210> SEQ ID NO 181
<211> LENGTH: 121
<212> TYPE: DNA
<213> ORGANISM: Artificial Sequence
<220> FEATURE:
<223> OTHER INFORMATION: synthetic

<400> SEQUENCE: 181
gcatttcctg agcttaatgc ttgggagcgt gctggtgctg atgcttcctc tgctggtatg    60
gttgacgccg gatttgagaa tcaaaaagag cttactaaaa tgcaactgga caatcagaaa   120
g                                                                  121

<210> SEQ ID NO 182
<211> LENGTH: 140
<212> TYPE: DNA
<213> ORGANISM: Artificial Sequence
<220> FEATURE:
<223> OTHER INFORMATION: synthetic

```
<400> SEQUENCE: 182
gcctcggtac ggtcaggcat ccacggcgct ttaaaatagt tgttatagat attcaaataa      60
ccctgaaaca aatgcttagg gattttattg gtatcagggt taatcgtgcc aagaaaagcg     120
gcatggtcaa tataaccagt                                                 140

<210> SEQ ID NO 183
<211> LENGTH: 127
<212> TYPE: DNA
<213> ORGANISM: Artificial Sequence
<220> FEATURE:
<223> OTHER INFORMATION: synthetic

<400> SEQUENCE: 183
ccaccagcaa gagcagaagc aataccgcca gcaatagcac caaacataaa tcacctcact      60
taagtggctg gagacaaata atctctttaa taacctgatt cagcgaaacc aatccgcggc     120
atttagt                                                               127

<210> SEQ ID NO 184
<211> LENGTH: 87
<212> TYPE: DNA
<213> ORGANISM: Artificial Sequence
<220> FEATURE:
<223> OTHER INFORMATION: synthetic

<400> SEQUENCE: 184
aggttttctg cttaggagtt taatcatgtt tcagactttt atttctcgcc ataattcaaa      60
ctttttttct gataagctgg ttctcac                                          87

<210> SEQ ID NO 185
<211> LENGTH: 77
<212> TYPE: DNA
<213> ORGANISM: Artificial Sequence
<220> FEATURE:
<223> OTHER INFORMATION: synthetic

<400> SEQUENCE: 185
gattgagtgt gaggttataa cgccgaagcg gtaaaaattt taattttttgc cgctgagggg     60 ttgaccaagc gaagcgc                                                     77
```

SIZE STANDARDS FOR NEXT-GENERATION SEQUENCING

CROSS-REFERENCE TO RELATED APPLICATIONS

This application is a U.S. National Stage of PCT Application No. PCT/US2019/017985 filed on Feb. 14, 2019 which claims priority to U.S. Provisional Application No. 62/630,463, filed Feb. 14, 2018, which are incorporated by reference herein as if set forth in its their entirety.

BACKGROUND

Size bias, arising from differential clustering or loading of DNA molecules of different lengths, is a common issue with next-generation sequencing platforms, such as Illumina® and PacBio® sequencing, and has the potential to introduce bias to measurements. This problem of size bias is generally not thought to affect many next generation sequencing applications since libraries are often constructed by randomly fragmenting DNA or cDNA. Thus, variations in molecule size are randomly distributed across template molecules and bias toward particular sizes are thought to average out. However, there are applications where library sizes are not randomly distributed, but rather result from the structure of the underlying data that is being collected (i.e., ATAC-Seq, RAD-Seq, some amplicon approaches) and tend to include fragments of particular lengths. In addition, there are applications where the effect of size bias is unknown. In such cases, no tool currently exists for characterizing size bias and comparing different sequencing runs and platforms with respect to clustering or loading size bias.

SUMMARY OF THE DISCLOSURE

In a first aspect, provided herein is a composition comprising a plurality of synthetic size standard polynucleotides, each synthetic size standard polynucleotide of the plurality comprising one or more next-generation sequencing adapter-flanked barcodes, wherein the plurality comprises defined ratios of synthetic size standard polynucleotides of at least two defined lengths. Each synthetic size standard polynucleotide of the plurality can have a defined length. The plurality can define a continuous or random length distribution spanning a defined portion of a genome. The size standard polynucleotides can comprise random genomic fragments of said defined portion of known sizes. The synthetic size standard polynucleotides can comprise nucleotides from a 16S rRNA gene, a GAPDH gene, an alpha-tubulin gene, or a PhiX174 genome. Each synthetic standard polynucleotide can be flanked by cut sites of a restriction enzyme. Each synthetic standard polynucleotide can comprise a feature allowing PCR-free quantitation of the synthetic standard. The synthetic size standard polynucleotides are encoded on a plasmid. The synthetic size standard polynucleotides can be produced by direct in vitro synthesis or PCR amplification.

In another aspect, provided herein is a method for detecting size bias in a sample comprising one or more template polynucleotides. The method can comprise or consist essentially of obtaining a sample comprising one or more template polynucleotides; spiking the sample with a plurality of synthetic size standard polynucleotides designed to detect size bias between two sample polynucleotides, each synthetic size standard polynucleotide of the plurality comprising a next-generation sequencing adapter-flanked size barcode and, optionally, a next generation sequencing adapter-flanked normalization barcode, wherein the plurality comprises defined ratios of synthetic size standard polynucleotides of multiple defined lengths; sequencing at least a portion of each polynucleotide of the spiked sample using a sequencer corresponding to the next-generation sequencing adapter; measuring the frequency of occurrence of the size barcode and, optionally, normalization barcode; and comparing the measured occurrence of the size barcodes and, optionally, the normalization barcode to an expected frequency occurrence of the normalization barcode and size barcodes, thereby generating a size standard polynucleotide size bias value. Each synthetic size standard polynucleotide can be encoded by a plasmid; wherein each next-generation sequencing adapter-flanked size barcode and, optionally, the next generation sequencing adapter-flanked normalization barcode are flanked by one or more restriction enzyme sites; and wherein the method further comprises contacting the spiked sample to one or more restriction enzymes that cleave at the one or more restriction enzyme sites, thereby liberating size barcodes and normalization barcodes of the plurality from the plasmids. The restriction enzyme can be selected from MlyI, BsmI, Bts$^\alpha$I, BsrDI, and SbfI. The next generation sequence adapters can be Illumina® adapters. The synthetic size standards can comprise nucleotides from a 16S rRNA gene, a GAPDH gene, an alpha-tubulin gene, or a PhiX174 genome.

In a further aspect, provided herein is a method for detecting size bias in a sequencing run. The method can comprise or consist essentially of (a) obtaining sequencing information for first N bases of a sequencing read, wherein the first N bases correspond to a size barcode of a synthetic size standard polynucleotide having a defined length; (b) applying an algorithm to the obtained sequencing information to calculate relative abundance of synthetic size standards detected in the sequencing run; and (c) plotting the determined relative abundance and size with to known, expected values to detect size bias in the sequencing run. In some cases, the method further comprises (d) mapping the sequencing read to a reference database to calculate sequencing error rates. In some cases, the method further comprises (e) using the size standards to report on sequence quality as a function of molecule length. The detecting can occur during the sequencing read. The detecting can occur after the sequencing read. The method can be computer-implemented.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, where:

FIGS. 2A-2D demonstrate Illumina® size standard pool composition and data. A) Composition of the Illumina® size standard constructs, which consist of three different backbone molecules (16S rRNA, GAPDH, and Tubulin), ranging from 150 bp to 1500 bp in length. B) Between lane and between flow cell differences in size bias profiles for HiSeq2500 Rapid Run (on-board clustering) and HiSeq2500 High Output (cBot clustering). C) Template-specific size biases observed on the HiSeq2500 in Rapid Run mode. D) Platform and construct-specific mean quality scores for the Illumina® size standard constructs for the first 50 bp of read 1.

FIG. 5A demonstrates differences in size standard measurements for three HiSeq 4000 runs (3 different flow cells).

FIG. 5B demonstrates a fragment size profile of the library run together with the size standards in run 1 of the HiSeq 4000.

FIG. 5C demonstrates a fragment size profile of the library run together with the size standards in run 2 of the HiSeq 4000.

FIG. 5D demonstrates a fragment size profile of the library run together with the size standards in run 3 of the HiSeq 4000.

FIG. 5E presents differences in size standard measurements for run 1 of the HiSeq 4000 and run 1 of the NextSeq.

FIG. 5F demonstrates a fragment size profile of the library run together with the size standards in run 1 of the NextSeq.

Figures 1A, 1B, 1C, 1D, 1E:
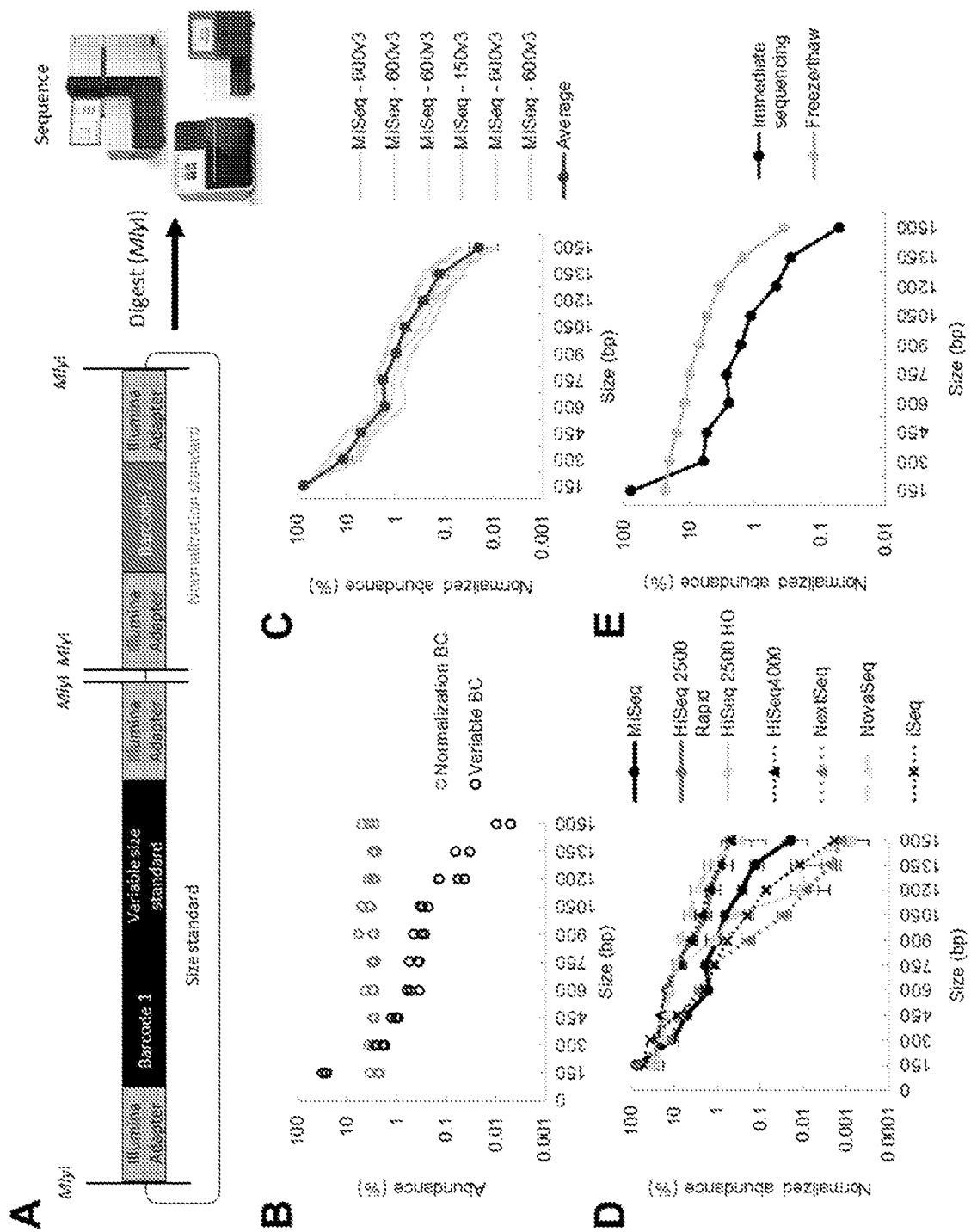
FIGS. 1A-1E demonstrate that Illumina® size standards allow measurement of sequencer-specific size biases. A) Design of REcount-based Illumina® size standard constructs. Each standard construct contains a normalization barcode, as well as a barcode associated with a variable size standard that can be liberated by MlyI digestion and directly sequenced. B) Raw abundance data for all 30 size standards and normalization barcodes from a MiSeq run. C) Run-to-run variability of multiple MiSeq runs (n=6 flow cells). D) Size bias profiles of the iSeq (n=1 flow cell), MiSeq (n=6 flow cells), HiSeq 2500 Rapid (n=1 flow cell, 2 lanes), HiSeq 2500 High Output (HO, n=2 flow cells, 10 lanes), HiSeq 4000 (n=3 flow cells, 6 lanes), NextSeq (n=4 flow cells), and NovaSeq (n=4 flow cells, 4 lanes) sequencers. E) Size bias profiles of the same library either clustered on the MiSeq immediately after denaturation, or clustered after freezing and thawing the denatured library. Error bars are +/−s.e.m.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The compositions and methods described herein are based at least in part on the inventors' study of DNA size bias in next generation sequencing protocols and their development of a set of molecular standards that report on this bias and useful as controls in DNA sequencing reactions. Advantages of the compositions and methods described herein are multifold. In particular, the compositions provide accurate and precise measurements of plasmid pools and allow measurement of sequencer-specific and run-specific size biases. In particular, the synthetic size standard compositions described herein are suitable for use as a spike-in control in next generation sequencing runs. Conventional standards used in this manner to assess, for example, DNA sequencing error rates, are randomly generated and are incapable of detecting and accounting for size bias.

In a first aspect, provided herein is a composition comprising or consisting essentially of a plurality of synthetic size standards, where the synthetic size standards are sequencing adapter-containing DNA molecules and where the plurality comprises a defined set of DNA molecules having predetermined lengths. Preferably, the plurality comprises known ratios of sequencing adapter-containing DNA molecules of particular lengths. In this manner, the composition is a set of size standards suitable for next generation sequencing reactions.

In some cases, the composition comprises or consists essentially of a plurality of sequencing adapter-containing DNA molecules, where the plurality defines a continuous or random length distribution spanning a given length range, and the plurality comprises known ratios of sequencing adapter-containing DNA molecules of particular lengths. The set of sequencing adapter-containing size standards for these compositions can be obtained from random genomic fragments. In some cases, each sequencing adapter-containing DNA molecule of the plurality comprises, from the sequencing start position, first N base pairs (bp), where N can vary between about 10 and about 300 bp, of each distinct sequencing adapter-containing DNA molecule of the plurality is a unique sequence among the pool of size standards. In such cases, length of the molecule being sequenced can be deduced by sequencing just the first N bases. This sequence serves as a barcode or molecular identifier for molecule length. In other cases, a similar unique sequence is located at the 3' end of each sequencing adapter-containing DNA molecule. Alternatively, sequences at the 5' and 3' ends of each sequencing adapter-containing DNA molecule together comprise a unique pair of sequences that are useful to deduce the length of the molecule being sequenced.

Sequencing adapters appropriate for the compositions and methods described herein include, without limitation, double-stranded and single-stranded oligonucleotides designed for compatibility with a sequencing workflow (e.g., a commercial sequencing platform). As used herein, an "adapter" is an oligonucleotide that is linked or is designed to be linked to a nucleic acid to introduce the nucleic acid into a sequencing workflow. An adapter may be single-stranded or double-stranded (e.g., a double-stranded DNA or a single-stranded DNA), or a hairpin adapter (e.g., for Pacific Biosciences sequencing). The term "adapter" encompasses unlinked adapter nucleic acids (i.e., in a state that is not linked to another nucleic acid) and adapters linked to one or more other nucleic acids. Some adapters comprise a universal sequence, meaning a sequence shared by a plurality of adapters that may otherwise have different sequences outside of the universal sequence. For example, a universal sequence provides a common primer binding site for a collection of nucleic acids from different target nucleic acids, e.g., that may comprise different barcodes. In some cases, the adapters comprise a defined but unknown sequence. For example, some embodiments of adaptors comprise a degenerate sequence of a defined number of bases (e.g., a 1- to 20-base degenerate sequence). Such a sequence is defined even if each individual sequence is not known—such a sequence may nevertheless serve as an index, barcode, tag, etc. marking nucleic acid fragments from, e.g., the same target nucleic acid.

In some embodiments, the adapters comprise one or more sequence elements such as a barcode nucleotide sequence ("barcode"). As used herein, the term "barcode" refers to a known polynucleotide sequence that allows some feature of a polynucleotide with which the barcode is associated to be identified. In some cases, barcodes are at least 3, 4, 5, 6, 7, 8, 9, 10, 11, 12, 13, 14, 15, or more nucleotides in length. In some cases, barcodes are shorter than 10, 9, 8, 7, 6, 5, or 4 nucleotides in length. In certain embodiments, the breakpoint of the library insert molecule serves as a molecular barcode that can be used to infer the size of the molecule being sequenced.

Additionally, adapters can contain one or more of a variety of other sequence elements including, without limitation, one or more amplification primer annealing sequences or complements thereof, one or more sequencing primer annealing sequences or complements thereof, one or more barcode sequences, one or more common sequences shared among multiple different adaptors or subsets of different adapters (e.g., a universal sequence), one or more restriction enzyme recognition sites, one or more overhangs complementary to one or more target polynucleotide overhangs, one or more probe binding sites (e.g., for attachment to a sequencing platform, such as a flow cell for massive parallel sequencing, such as developed by Illumina, Inc.), one or more random or near-random sequences (e.g., one or more nucleotides selected at random from a set of two or more different nucleotides at one or more positions, with each of the different nucleotides selected at one or more positions represented in a pool of adapters comprising the random sequence), and combinations thereof. Preferably, the adapter sequence is capable of hybridizing to a sequencing primer such as a custom sequencing primer or a sequencing primer compatible with a commercially available NGS sequencing system (e.g., a Truseq primer sequence compatible with the NGS platform produced by Illumina, Inc).

In some cases, size standards of the compositions described herein may be flanked the 5' side and/or 3' side by next-generation sequencing adapters. As used herein, the term "next-generation sequencing adapter" refers to adapters configured for use with a next-generation sequencing platform. In some cases, size standards are flanked by next-generation adapters suitable for use with Illumina® sequencing platforms. In other cases, the size standards are flanked by adapters suitable for use with other next generation DNA sequencing platforms such as, for example, Pacific Biosciences (PacBio®), Ion Torrent, 454 Sequencing, and Nanopore sequencing devices. Many next-generation sequencing (NGS) platforms are available for the high-throughput, massively parallel sequencing of nucleic acids. NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, Inc., and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively. Some NGS systems, such as the HiSeq and MiSeq systems produced by Illumina, Inc., use a sequencing-by-synthesis (SBS) approach, wherein a nucleotide sequence is determined using base-by-base detection and identification.

In some cases, sequencing adapter-containing DNA molecules are encoded on a plasmid or an engineered (i.e., synthetic) genetic construct such as a transposon or viral genome. In other cases, sequencing adapter-containing DNA molecules are produced by direct synthesis or PCR amplification.

In some cases, the plurality is obtained from fragments of a known genome such as a phage genome (e.g., PhiX174 phage genome). For example, the defined mixture of sequencing adapter-containing DNA molecules can comprise fragments of PhiX174 genomic DNA, where the length of each fragment of the mixture is known and fragments of particular sizes are mixed together at known ratios. In other cases, the plurality is obtained using purely synthetic, non-naturally occurring DNA fragments.

In some cases, each sequencing adapter-containing DNA molecule of the plurality comprises restriction sites that enable PCR-free sequencing and counting of the molecules. In such cases, the composition comprising a defined mixture of sequencing adapter-containing DNA molecules is obtained using PCR-free quantification barcode technology described in PCT/US17/31271, which is incorporated herein by reference in its entirety. By way of example, FIG. 1A demonstrates design of a plurality of barcode-containing, sequencing adapter-flanked DNA molecules that further comprise recognition sites for restriction enzyme MlyI. As shown in FIG. 1A, the barcode-containing, adapter-flanked DNA molecules were liberated from plasmid constructs by a MlyI digest and then directly sequenced. Restriction enzymes other than MlyI can be used including, without limitation, BsmI, Bts"I, BsrDI, and SbfI. As demonstrated in the Examples that follow, restriction enzymes that produce small (1-10 bases) or even large (30-50 bases) single-stranded overhangs when cleaving at a recognition site are useful for liberating barcode-containing, adapter-flanked DNA molecules for sequencing. Accordingly, it will be understood that any restriction enzyme that produces such overhangs when cleaving DNA into fragments at or near specific recognition sites are suitable for use for the compositions and methods described herein. Additionally, CRISPR/Cas, TALENs, zinc-finger nucleases (ZFNs), or combinations thereof, containing either double-strand endonucleases or pairs of nicking endonucleases, can be used to liberate constructs in a similar manner.

In some cases, each sequencing adapter-containing DNA molecule of the plurality comprises a second sequencing adapter-containing barcode construct of uniform size on the same plasmid. This second sequencing adapter-containing barcode construct is configured to function as a normalization barcode. Referring to FIGS. 1A-1E, use of a normalization barcode with a size standard-associated barcode allows for measurement of sequencer-specific size biases. For example, FIG. 1A demonstrates design of construct that contain a normalization barcode as well as a barcode associated with a variable size standard. These constructs further contained restriction enzyme site such that each barcode can be liberated by enzymatic digestion and directly sequenced.

In another aspect, provided herein are methods for detecting size bias in a sample comprising one or more template polynucleotides. The method can comprise or consist essentially of obtaining a sample comprising one or more template polynucleotides, and spiking the sample with a plurality of synthetic size standard polynucleotides designed to detect size bias between two sample polynucleotides, each synthetic size standard polynucleotide of the plurality comprising a next-generation sequencing adapter-flanked size barcode and, optionally, a next generation sequencing adapter-flanked normalization barcode, where the plurality comprises defined ratios of synthetic size standard polynucleotides of multiple defined lengths. In a next step, at least a portion of the spiked sample is sequenced using a sequencer corresponding to the next-generation sequencing adapter. The frequency of occurrence of the normalization barcode, size barcode, and one or more template polynucleotides is measured, and the measured occurrence of each is compared to an expected frequency occurrence of the size barcodes and, optionally, normalization barcode, thereby generating a size standard polynucleotide size bias value.

In some cases, size standards are not spiked into the sample and, instead, are run in one or more separate, parallel reactions.

In some cases, synthetic size standard polynucleotides comprise one or more features that permit PCR-free quantitation of the synthetic standard. As described and exemplified herein, one may design synthetic size standard polynucleotides to comprise sequencing adapters as well as flanking restriction sites. In some cases, each synthetic size standard polynucleotide is encoded by a plasmid, and each next-generation sequencing adapter-flanked size barcode and, optionally, next generation sequencing adapter-flanked normalization barcode is flanked by one or more restriction enzyme sites. To liberate the barcodes from the plasmids, the sample is contacted to restriction enzymes that cleave at the one or more restriction enzyme sites. Exemplary restriction enzymes include, without limitation, MlyI, BsmI, Bts$^\alpha$I, BsrDI, and SbfI.

As described herein, a wide variety of sequencing adapters can be used with the methods. It will be advantageous in many cases, however, to use commercially available sequencing adapters such as Illumina® next-generation sequence adapters. In other cases, the size standards are flanked by adapters suitable for use with other next generation DNA sequencing platforms such as, for example, Pacific Biosciences, Ion Torrent, 454 Sequencing, and Nanopore sequencing devices.

In some cases, the plurality comprises different synthetic standard polynucleotides of various defined lengths. In other cases, the synthetic size standards comprise nucleotides from a defined gene or genome. Exemplary genes and genomes for the methods provided herein include, without limitation, a 16S rRNA gene, a GAPDH gene, an alpha-tubulin gene, or a PhiX174 genome. In some cases, the plurality is obtained using purely synthetic, non-naturally occurring DNA fragments.

In some cases, synthetic size standard polynucleotides comprise one or more features that permit PCR-free quantitation of the synthetic standard. As described and exemplified herein, one may design synthetic size standard polynucleotides to comprise sequencing adapters as well as flanking restriction sites. In some cases, the methods comprise multiplexed PCR-free barcode sequencing using orthogonal restriction enzymes.

Figures 3A, 3B:
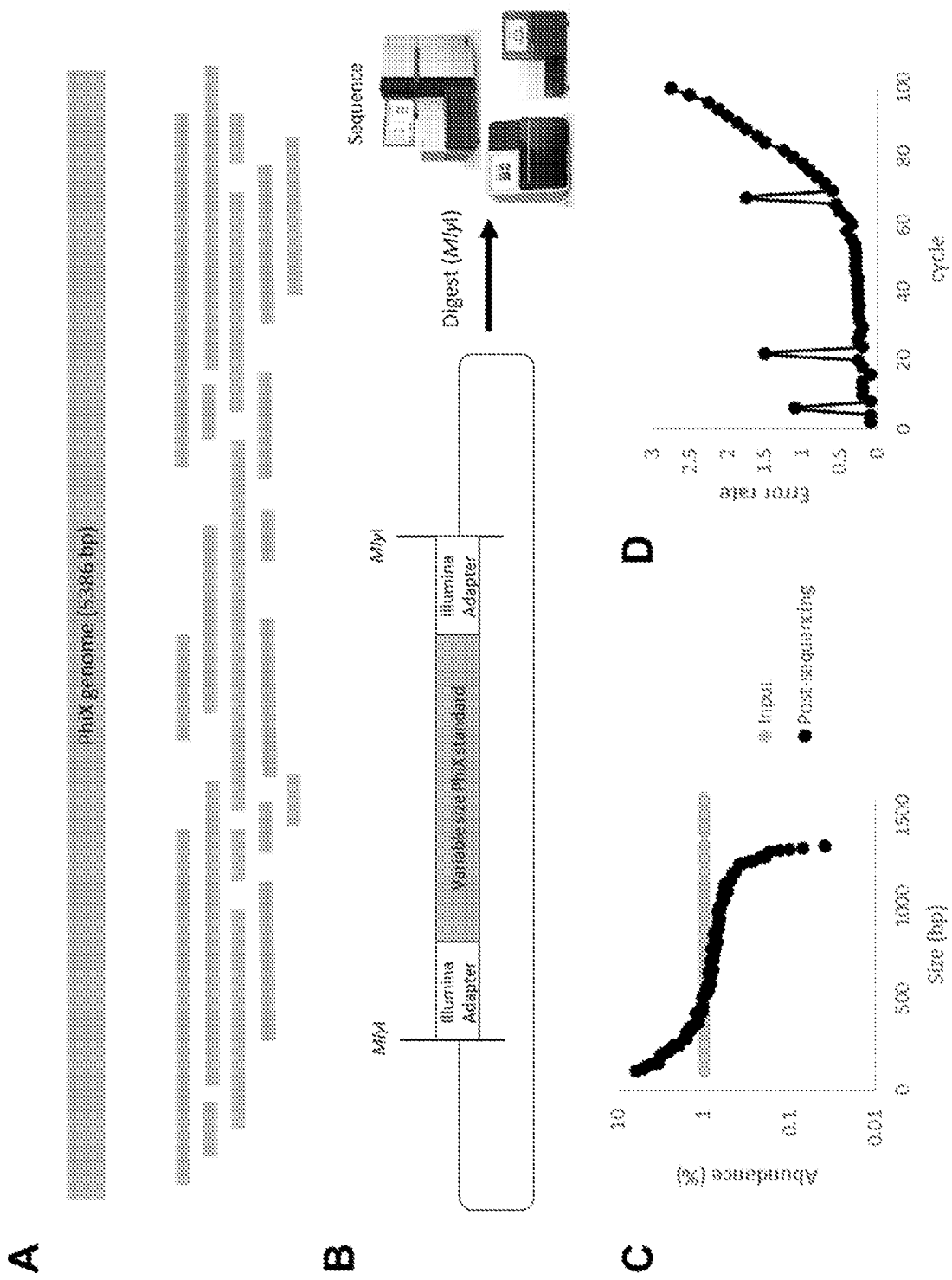
FIGS. 3A-3B are schematics illustrating PhiX-derived size standards. Fragments of the PhiX174 genome of defined sizes and with different breakpoints (A) are flanked by Illumina® adapters and MlyI restriction sites, and cloned into a plasmid (B). The size and breakpoint of each clone is determined, plasmids are pooled at an eqimolar ratio, and the standard molecules can be liberated by digestion with MlyI and sequenced to report on size bias, while also allowing sequencing error rates and other run metrics to be calculated.
Figure 4:
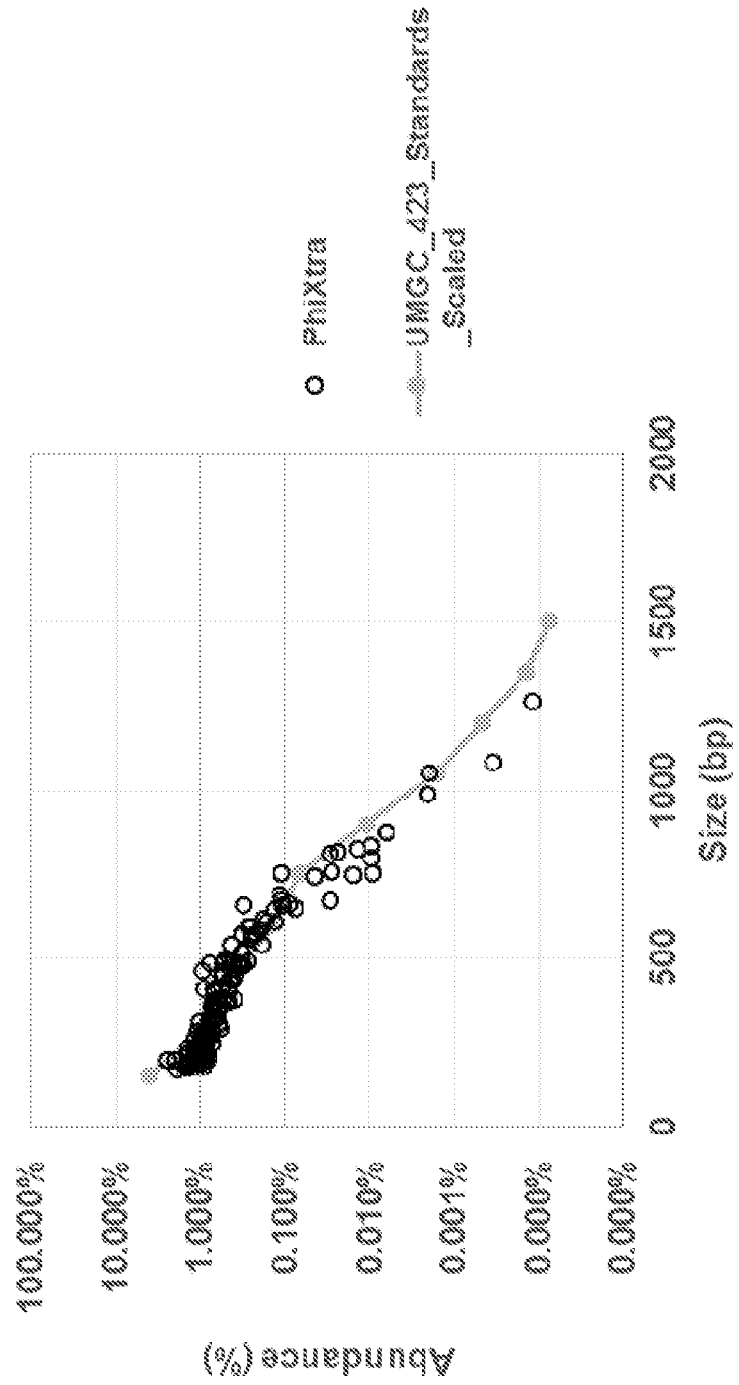
FIG. 4 is a table presenting percent abundance of PhiX size standards ("PhiXtra") and original PCR-free quantification barcode size standards ("UMGC_423_Standards_Scaled").

In another aspect, provided herein are methods for quality control or real-time run reporting. In some cases, the methods comprise applying an algorithm or software program to size standard data (e.g., evidence of size bias). For example, an algorithm or software program can be used to convert information about the first N bases of read 1 (where the first N bases of read 1 correspond to the unique polynucleotide barcode that is distinctive for size standard identity and, optionally, normalization barcode identity) and determine the relative abundance of different size standards observed in the sequencing run. Referring to FIG. 3C, relative abundance can be compared to the known expected values to detect bias due to molecule length. For PhiX or other synthetic size standards, a software program can be used to map sequencing reads to a reference database in order to identify discrepancies and calculate sequencing error rates. Such analysis could either be performed after a sequencing run is complete, or as a sequencing run is in progress.

The terms "detect" or "detection" as used herein indicate the determination of the existence, presence or fact of a target molecule in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified.

The terms "quantity", "amount" and "level" are synonymous and generally well-understood in the art. The terms as used herein may particularly refer to an absolute quantification of a target molecule in a sample, or to a relative quantification of a target molecule in a sample, i.e., relative to another value such as relative to a reference value or to a range of values indicating a base-line expression of the biomarker. These values or ranges can be obtained from a single subject (e.g., human patient) or aggregated from a group of subjects. In some cases, target measurements are compared to a standard or set of standards.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In interpreting this disclosure, all terms should be interpreted in the broadest possible manner consistent with the context. It is understood that certain adaptations of the invention described in this disclosure are a matter of routine optimization for those skilled in the art, and can be implemented without departing from the spirit of the invention, or the scope of the appended claims.

So that the compositions and methods provided herein may more readily be understood, certain terms are defined:

Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Various exemplary embodiments of compositions and methods according to this invention are now described in the following non-limiting Examples. The Examples are offered for illustrative purposes only and are not intended to limit the scope of the present invention in any way. Indeed, various modifications in addition to those shown and described herein will become apparent to those skilled in the art from the foregoing description and the following examples and fall within the scope of the appended claims.

EXAMPLES

Example 1—PCR-Free Barcode Sequencing Strategy for Highly Accurate Quantification of Engineered Genetic Constructs This section describes a novel PCR-free direct counting method, REcount (Restriction Enzyme enabled counting), for quantifying sequence tags associated with engineered genetic constructs that is straightforward to implement and allows for direct NGS-based counting of a potentially enormous number of sequence tags. In this approach, an Illumina® adapter-flanked DNA barcode is liberated by digesting with MlyI (a type IIS restriction enzyme that produces blunt-ended molecules) and sequenced to directly count template molecule abundance (FIG. 1A). This examples demonstrates use of REcount to design a set of synthetic DNA standards that can be used to assess clustering bias due to molecule length on Illumina® sequencers, and demonstrate that there is substantial variation in size bias between different Illumina® instruments. Next, we assessed the impact of size bias across several common applications of NGS, including transcriptomic measurements (RNA-Seq [20]), reduced-representation genotyping (RAD-Seq/GBS [21]), and accessible chromatin profiling (ATAC-Seq [22]).

Methods

Illumina® Size Standard Plasmids

Illumina® size standards were designed using three different template molecules as backbones for the variable length fragment; the 16S rRNA gene (16S) from *E. coli*, the alpha-Tubulin84B gene (Tubulin) from *D. melanogaster*, and the Glyceraldehyde-3-phosphate dehydrogenase 1 (GAPDH) gene from *D. melanogaster* (FIG. 2A). Any naturally occurring MlyI sites in these fragments were modified to remove this restriction site. The variable length size standards represent nested fragments of these three genes with breakpoints chosen to generate specific molecule lengths, with GC contents between 40-60% (FIG. 2A). In order to minimize repetitive sequences, different adapters were used for the normalization and variable size standards (Nexter and TruSeq, respectively), and the normalization and size standards were synthesized in opposite orientations in the construct. Both the Illumina® adapter flanked variable and normalization barcode constructs were flanked by MlyI restriction sites. The Illumina® size standard constructs were synthesized by GenScript in the pUC57 cloning vector. Approximately 4 µg of each lyophilized plasmid was resuspended in 40 µl of EB (Qiagen). Plasmids were quantified using a Quant-iT PicoGreen dsDNA assay (Thermo Fisher Scientific) and normalized to 10 nM to account for the variable sizes of the plasmids, then pooled at an equimolar ratio.

Sequencing Library Preparation

Even and staggered pool REcount measurements: The following MlyI digests were set up for PCR-free quantification: 200-500 ng even or staggered pool DNA, 2 µl Cutsmart buffer (NEB), 1 µl MlyI (NEB), and volume was adjusted to 20 µl with nuclease-free water. Digests were incubated at 37° C. for 1 hour, followed by 20 minutes at 65° C. 30 µl of water was added to each digest (to bring the volume up to 50 µl). 30 µl (0.6×) of AmpureXP beads (Beckman Coulter) were added and after a 5 minute incubation, beads were collected on a magnet and the supernatant was transferred to a new tube (discarded beads). 80 µl (1×) of AmpureXP beads was added, washed 2× for 30 seconds using fresh 80% ethanol, and beads were air dried for 10 minutes, followed by elution in 20 µl of EB (Qiagen). Libraries were quantified using a Quant-iT PicoGreen dsDNA assay (Thermo Fisher Scientific), fragment sizes were assessed using an Agilent Bioanalyzer High Sensitivity assay, and libraries were normalized to 2 nM for sequencing.

Illumina® size standards: The following digest of the Illumina® size standard pool was set up: 175 µl DNA (10 nM), 20 µl CutSmart buffer (NEB), 5 µl MlyI (NEB). The reaction was incubated at 37° C. for 1 hour, followed by 65° C. for 20 minutes. The library was quantified using a Quant-iT PicoGreen dsDNA assay (Thermo Fisher Scientific), fragment sizes were assessed using an Agilent Bioanalyzer High Sensitivity assay, and libraries were normalized to 2 nM for sequencing.

Sequencing: DNA libraries were denatured with NaOH and prepared for sequencing according to the protocols described in the Illumina® iSeq, MiSeq, NextSeq, HiSeq 2500, HiSeq 4000, and NovaSeq Denature and Dilute Libraries Guides. Libraries were generally sequenced along with other samples in a fraction of a sequencing lane.

REcount data analysis: Demultiplexed fastq files were generated using Illumina® bcl2fastq software. REcount data was analyzed using custom R and Python scripts and BioPython [40]. The first 20 bp of the sequencing reads was mapped against a barcode reference file, with a maximum of 2 mismatches allowed, using a custom script which is available on Github at github.com/darylgohl/REcount on the Internet/World Wide Web. For the analysis of quality scores (FIG. 2D), the data for all runs on a given platform was concatenated into a single fastq file, the split into individual fastq files for each individual construct, based on the 20 bp sequence barcodes in each construct. Next, the reads were trimmed to 50 bp using cutadapt [42], so that all constructs and sequencing runs could be compared in a standardized manner. Mean quality scores were calculated for each construct that was represented by at least 100 reads in the data set. This analysis was carried out using a custom Python script.

Non-nucleosomal: <100 bp
Mono-nucleosomal: 180-247 bp
Di-nucleosomal: 315-473 bp
Tri-nucleosomal: 558-615 bp MACS [26] was used to call peaks that were induced by PAX3 expression, and IGV [51] was used to visualize read pileups and MACS peaks. Peaks detected in 2 out of 3 samples were identified using BEDTools [52].

Results

Using REcount-Based Size Standards to Measure Size Bias in Illumina® Sequencing

While it is known that molecule size affects clustering and sequencing efficiency on Illumina® sequencers [23], the extent of this bias and the degree to which it differs between different Illumina® instruments has not been characterized in detail. Thus, we used REcount to characterize the size bias profiles of the Illumina® iSeq, MiSeq, HiSeq 2500, HiSeq 4000, NextSeq, and NovaSeq sequencers. We synthesized 30 constructs, each of which contained an MlyI-flanked normalization barcode of consistent length (164 bp), and a barcode-containing variable-length insert ranging from 22 bp to 1372 bp, resulting in adapter-flanked molecules between 150 and 1500 bp (FIG. 2A). In order to minimize sequence-specific artifacts, the variable-length inserts were chosen to have between 42% and 58% GC content, and were comprised of 10 constructs each (spanning the full 150 bp-1500 bp size range) derived from three different molecules; the *Escherichia coli* (*E. coli*) 16S rRNA gene (16S), the *Drosophila melanogaster* (*D. melanogaster*) alpha-Tubulin84B gene (Tubulin), and the *D. melanogaster* Glyceraldehyde-3-phosphate dehydrogenase 1 (GAPDH) gene (FIG. 2A).

These Illumina® size standard constructs were pooled at an equimolar ratio based on fluorometric DNA concentration measurements, digested with MlyI, and sequenced on different Illumina® DNA sequencers with no intervening clean-up step, to ensure that no material was lost. Representative data from a single MiSeq run is shown in FIG. 1B. Since each normalization barcode is present at an equimolar ratio to the corresponding size standard (as they are on the same plasmid), this allows any inaccuracies in plasmid pooling to be accounted for. Within a sequencing platform, clustering size bias exhibits run-to-run variation (FIG. 1C). All six of the sequencers we tested exhibited preferential clustering of smaller fragments, consistent with previous anecdotal observations (FIG. 1D). However, the magnitude of this effect and the shapes of the size bias curves differ substantially between the iSeq, MiSeq, HiSeq 2500, HiSeq 4000, NextSeq, and NovaSeq (FIG. 1D). Differences were also seen between the HiSeq 2500 in Rapid Run (onboard clustering) and High Output (cBot clustering) modes (FIG. 1D). In addition, we observed an effect of molecule length on sequencing quality score, with a general trend towards longer molecules having lower quality scores (FIG. 2D). The magnitude of the effect of molecule length on sequence quality varied among the different instruments.

The denaturation process can also affect the size bias observed on Illumina® instruments. Denatured libraries are sometimes saved for re-sequencing in the case of a run failure (although Illumina, Inc.'s best practices recommend preparing freshly denatured libraries). To test whether freshly denatured libraries perform differently from frozen denatured libraries, we sequenced a freshly denatured library on a MiSeq, and the same denatured library one day later, after a freeze-thaw cycle, on a second MiSeq. The freeze-thaw cycle had a substantial effect on the size bias profile of this library; in particular, there was a dramatic reduction in the fraction of 150 bp molecules observed, resulting in a corresponding upward shift of the curve (FIG. 1E). It is likely that this shift reflects differential re-annealing of 150 bp fragments (which are in molar excess due to the presence of the large number of similarly sized normalization barcodes), or other small library molecules in the sequencing pool. This observation suggests that some of the difference in clustering size bias observed between the different platforms may be due to differences in denaturation conditions, the amount of time between loading the library and clustering, and whether the clustering process takes place in a chilled compartment (such as on the MiSeq) or not (such as the HiSeq2500 and NextSeq). Consistent with this idea, the variation between HiSeq2500 and HiSeq 4000 flow cells is much larger than the variation between the lanes on the same flow cell (FIG. 2B).

Figure 5A:
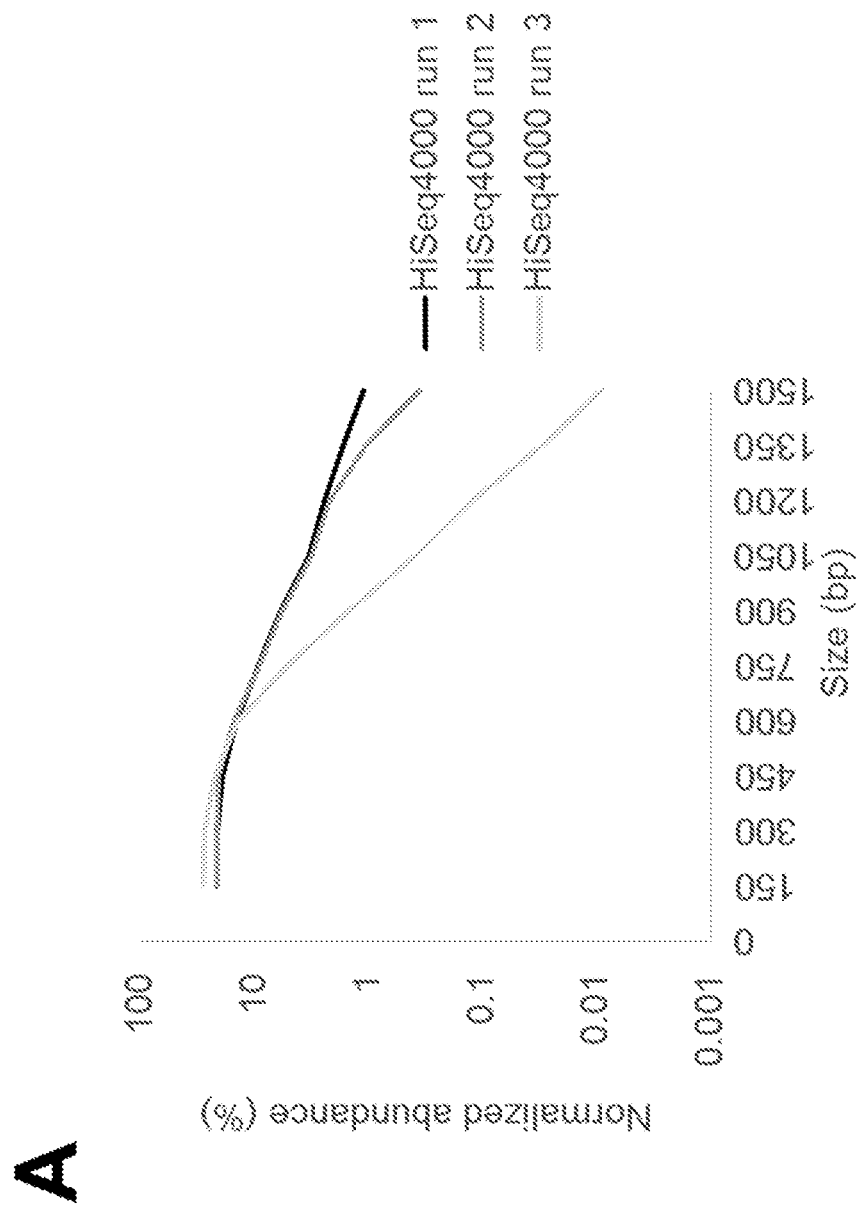
FIGS. 5A-5F demonstrate context-specific effects on clustering of size standards.
Figure 5B:
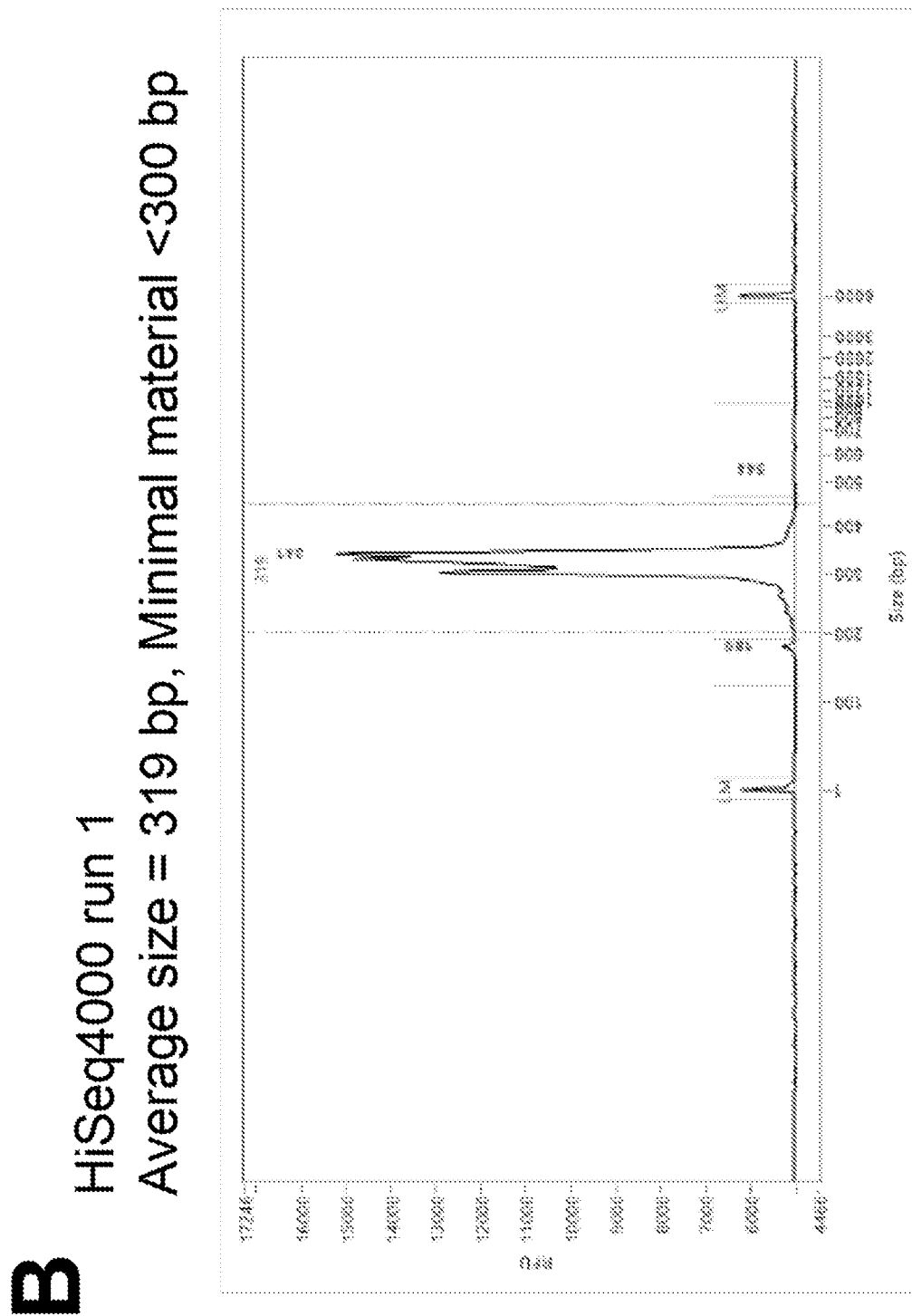
Figure 5C:
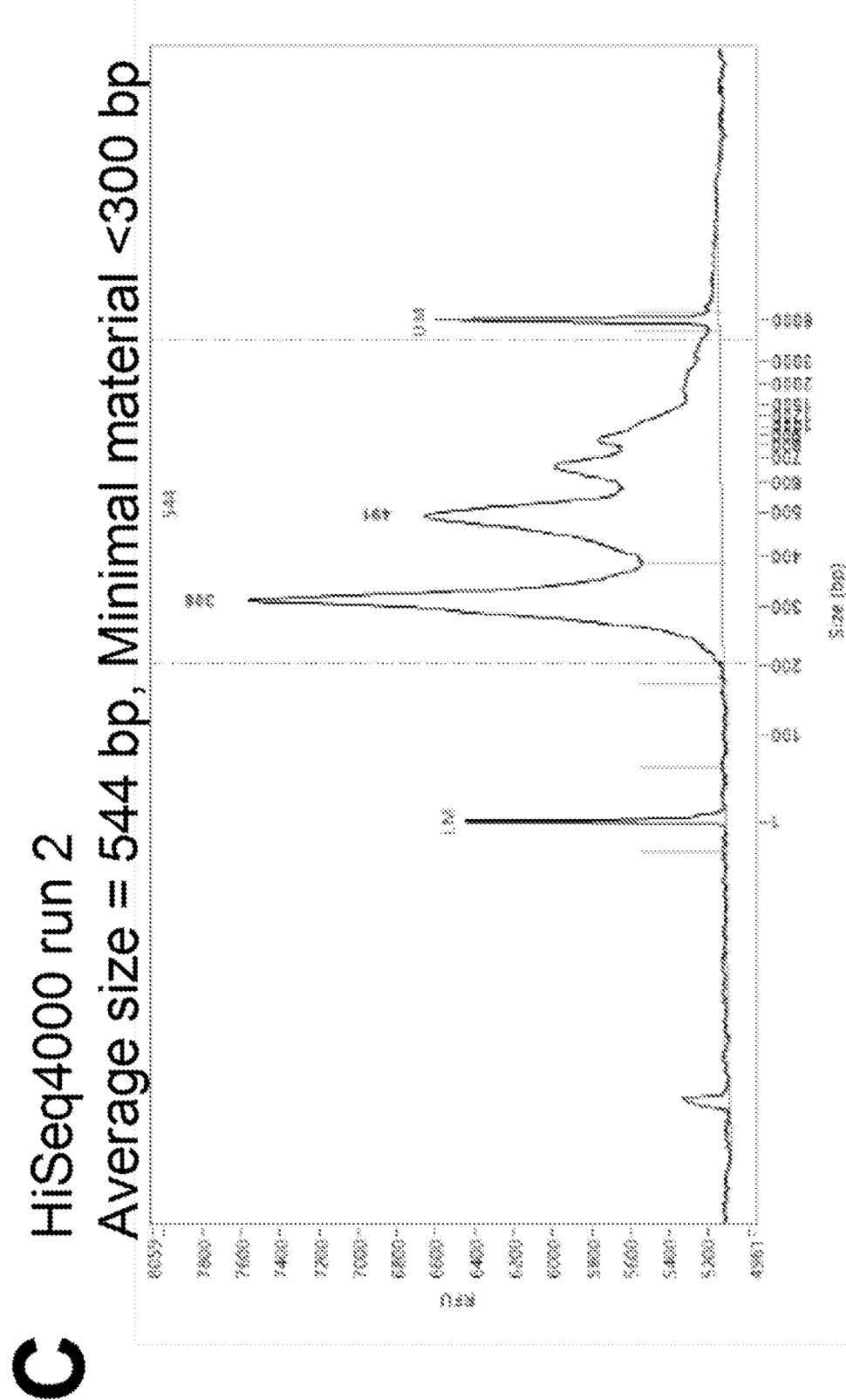
Figure 5D:
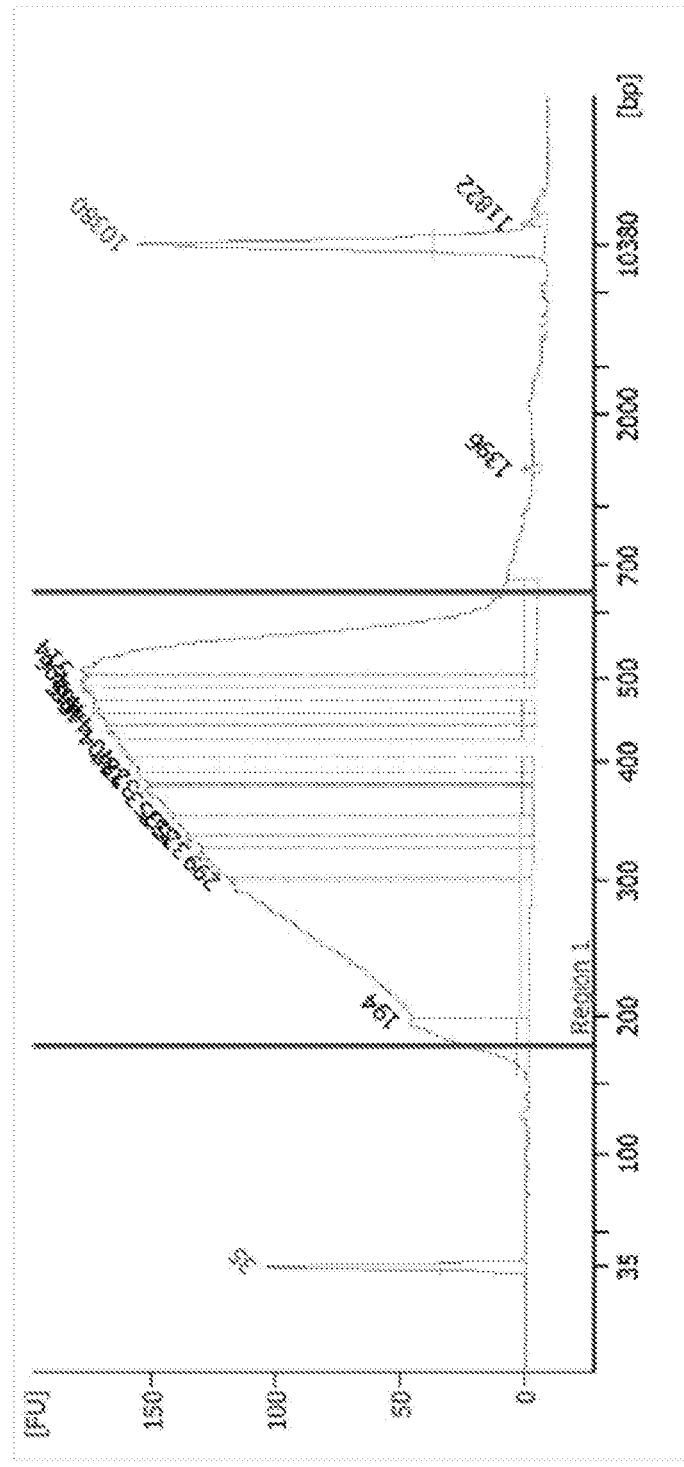
Figure 5E:
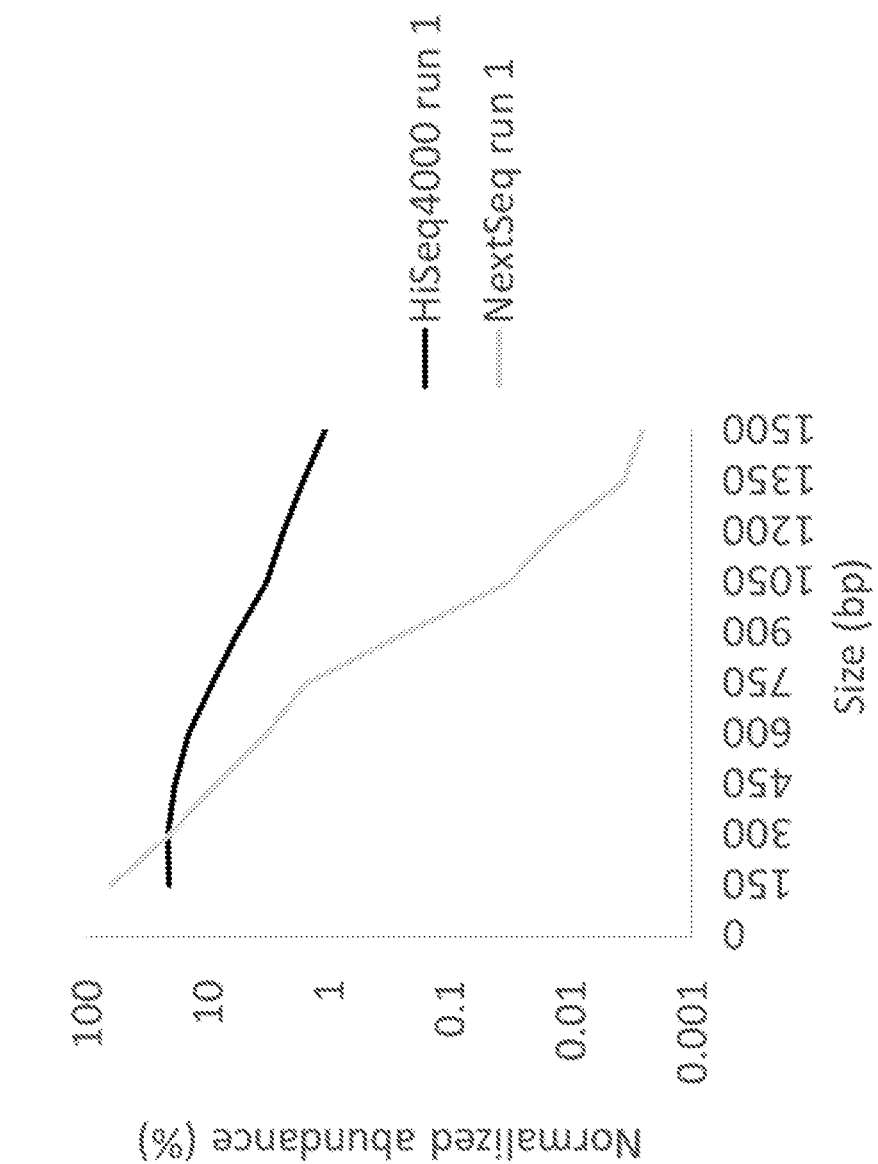
Figure 5F:
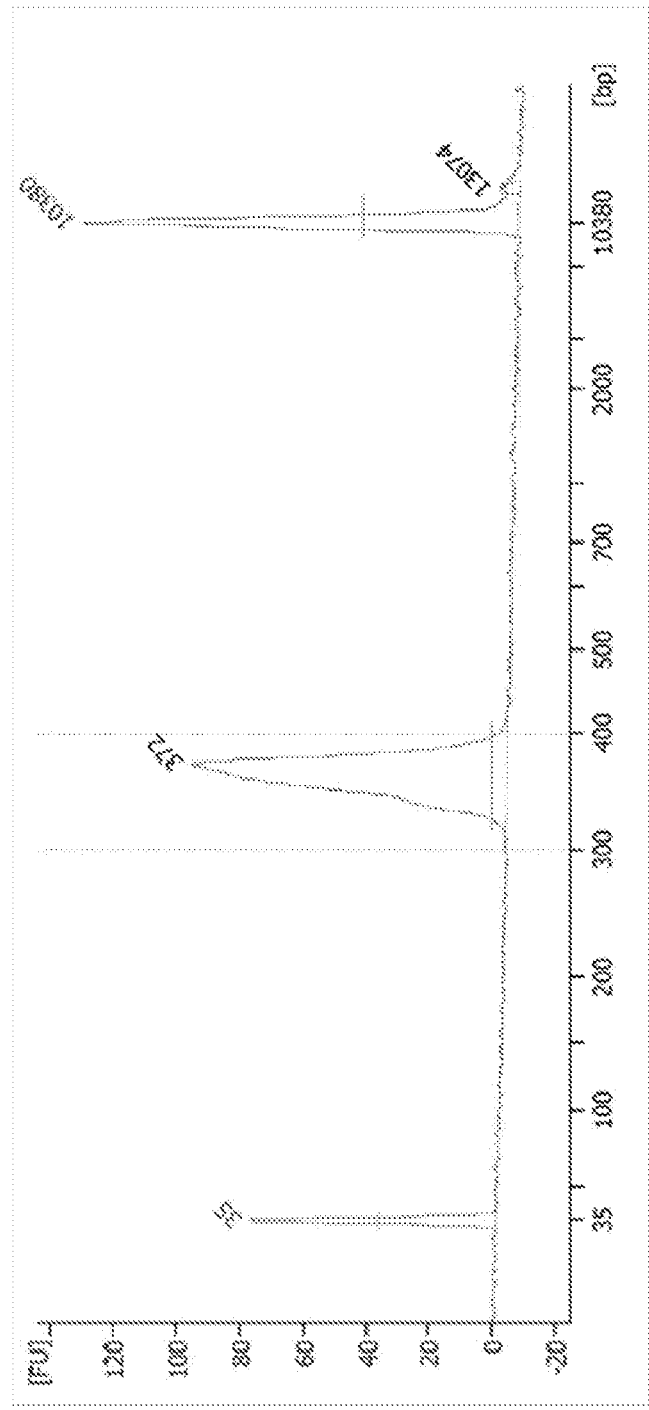

It is also likely that a portion of the variability between flow cells is due to differences in the size distributions of the libraries being sequenced together with the synthetic size standards, as competition for clustering will occur between all molecules in the sequencing lane. We observed a shift in the curve corresponding to a decreased representation of the larger size standards when they were sequenced together with a library containing a significant amount of material that was smaller than 300 bp on the HiSeq 4000 (FIGS. 5A-5F). Although the size standards were sequenced together with different libraries across the different instruments, this context-dependent clustering is not sufficient to explain the large differences we see between different instruments. For example, libraries with similar average sizes and distributions yielded dramatically different measurements of size bias on the NextSeq versus the HiSeq 4000 (FIGS. 5E-5F).

Surprisingly, we also detected an instance of construct-specific size bias, specifically on the HiSeq 2500 platform in Rapid Run mode (FIG. 2C). In contrast to the iSeq, MiSeq, HiSeq 2500 High Output, HiSeq4000, NextSeq, and NovaSeq where no systematic construct-specific biases were observed, the size bias curves for the 16S, GAPDH, and alpha-Tubulin constructs separated as size increased, with 16S showing much less of a drop-off with increased molecule size. One possible explanation for this difference is that the 16S rRNA gene has substantial secondary structure [24], which may serve to shorten the effective length of the molecule during the clustering process. This phenomenon may be due to differences in the clustering process or temperature on this platform, which may be less effective at dissociating the secondary structure of the 16S rRNA gene (available at support.alumina.com/bulletins/2016/10/considerations-when-migrating-nonillumina-libraries-between-sequencing-platforms.html on the Internet/World Wide Web). The HiSeq and MiSeq also have different recommended NaOH concentrations for denaturing libraries. It is possible that long molecules, particularly those with highly stable secondary structure, are incompletely denatured under the HiSeq denaturing conditions.

Discussion

We used REcount to measure size bias on several different Illumina® sequencers. We found that size bias can vary between runs and instruments and that the denaturation procedure can affect the size bias (FIGS. 1A-1E). Due to the competitive clustering of molecules of different sizes, it is likely that a portion of the variability between runs and lanes is due to differences in the size distributions of the libraries being sequenced together with the synthetic size standards. Such context-specific effects may be more prominent on patterned flow cell instruments, where library molecules compete for a defined number of clustering sites. Thus, the shape of the size bias curve is likely sensitive to both the size distribution of the libraries being sequenced along with the size standards, as well as the proportion of the lane devoted to the size standards.

In sum, these results indicate that care should be taken when interpreting quantitative measurements or comparing data across different platforms. This is particularly true in cases where library size distributions are non-random such as in several chromatin profiling methods (e.g., ATAC-Seq [22], FAIRE-Seq/MAINE-Seq [28]), approaches that use restriction digestion to fragment DNA (e.g., RAD-Seq [21]), amplicons that vary in length (e.g., fungal ITS sequencing [29]), or techniques such as TAIL-Seq [30] that explicitly seek to measure molecule length. In addition, because the fragmentation pattern of cell free DNA (cfDNA) is dependent on the chromatin state of the tissue of origin [31], it is also possible that sequencer size bias could influence the measurement of mutant allele fractions in cfDNA [32]. Constructs such as those described here could be routinely spiked into Illumina® sequencing runs to monitor size bias, similar to the use of PhiX to report on sequencing error rates and other base-calling metrics.

We demonstrated that REcount-based measurements of defined plasmid pools are more accurate than PCR-based measurements, that replicate measurements have high precision, and that the technique is amenable to multiplexing through the use of orthogonal restriction enzymes. We used REcount to measure size bias across different Illumina® sequencers and found that there are considerable differences in the efficiency of clustering due to molecule length among the different Illumina® instruments. We identified sample denaturation as a factor that can influence size bias. We showed that while a randomly sheared RNA-Seq library does not exhibit sequencer-specific quantitative bias in gene expression counts, sequencer size bias can influence both the interpretation of results and the economics of sequencing in cases where library fragment distributions are non-random, such as in RAD-Seq and ATAC-Seq. The quantitative measurements of size bias that we present and the synthetic standards we have developed provide tools for monitoring and accounting for size bias in Illumina® sequencing.

The 30 synthetic size standards comprising MyII recognition sites (5'-GAGTC-3' or 5'-GACTC-3') and Illumina® adapters are presented in Table 1. Size standard read 1 adapter: 5'-aatgatacggcgaccaccgagatctacactctttccctacacgacgctcttccgatct-3 (SEQ ID NO:1)'. Size standard read 2 adapter: 5'-agatcggaagagcacacgtctgaactccagtcacAATCAGTCTCGTatctcgtatgccgtatctgatg-3' (SEQ ID NO:2).

Normalization standard read 1 adapter: ctgtctatatacacatctgacgctgccgacgaATCACCAGGTGTgtgtagatctcggtggtcgccgtatcatt (SEQ ID NO:3).

Normalization standard read 2 adapter: caagcagaagacggcatacgagatTGGTCAACGATAgtctcgtgggctcggagatgtgtataagagacag (SEQ ID NO:36). It should be noted that the normalization standard read 1-adapted construct is presented in the opposite orientation to the size standards. The sequences listed above are in the orientation in which they appear in Table 1.

TABLE 1

Synthetic Size Standards

| Size Standard | Sequence |
| --- | --- |
| 233_ILL_size_150_ECO_16S | GAGTCGACAAaatgatacggcgaccaccgagatctacactctttccctacacgacgctcttccgat ctGAGCATGCCGATGGTTTGTTAAagatcggaagagcacacgtctgaactccagtcacAATCAGTCTCGTatctcgtatgccgtcttctgcttgTTGTCGACTCTAGGGATAACAGGGTAATGAGTCGACAAcaagcagaagacggcatacgagatTGGTCAACGATAgtctcgtgggctcggagatgtgtataagagacagGCCGCCCGTCACAGCACGTActgtctcttatacacatctgacgctgccgacgaATCACCAGGTGTgtgtagatctcggtggtcgccgtatcattTTGTCGACTC (SEQ ID NO: 4) |
| 234_ILL_size_300_ECO_16S | GAGTCGACAAaatgatacggcgaccaccgagatctacactctttccctacacgacgctcttccgat ctAGACTATCGCCTTTAGCCTCAAATTGAAGAGTTTGATCATGGCTCAGATTGAACGCTGGCGGCACGGCCTAACACATGCAAGTCGAACGGTAACAGGAAGAAGCTTGCTCTTTGCTGAGAGTGGCGGACGGGTGAGTAATGTCTGGGAAACTGCCTGATGGAGGGGGATAACagatcggaagagcacacgtctgaactccagtcacAATCAGTCTCGTatctcgtatgccgtcttctgcttgTTGTCGACTCTAGGGATAACAGGGTAATGAGTCGACAAcaagcagaagacggcatacgagatTGGTCAACGATAgtctcgtgggctcggagatgtgtataagagacagGCAGCTGTTAG |

TABLE 1-continued

Synthetic Size Standards

| Size Standard | Sequence |
|---|---|
| | AGACGAATCctgtctcttatacacatctgacgc<br>tgccgacgaATCACCAGGTGTgtgtagatctcg<br>gtggtcgccgtatcattTTGTCGACTC<br>(SEQ ID NO: 5) |
| 235_ILL_<br>size_450_<br>ECO_16S | GAGTCGACAAaatgatacggcgaccaccgagat<br>ctacactctttccctacacgacgctcttccgat<br>ctTGATGTATATAGCCGGCGGCAAATTGAAGAG<br>TTTGATCATGGCTCAGATTGAACGCTGGCGGCA<br>CGGCCTAACACATGCAAGTCGAACGGTAACAGG<br>AAGAAGCTTGCTCTTTGCTGAGAGTGGCGGACG<br>GGTGAGTAATGTCTGGGAAACTGCCTGATGGAG<br>GGGGATAACTACTGGAAACGGTAGCTAATACCG<br>CATAACGTCGCAAGACCAAAGAGGGGGACCTTC<br>GGGCCTCTTGCCATCGGATGTGCCCAGATGGGA<br>TTAGCTAGTAGGTGGGGTAACGGCTCACCTAGG<br>ACGACGATCCCTAGCTGGTCTGAGAGGAagatc<br>ggaagagcacacgtctgaactccagtcacAATC<br>AGTCTCGTatctcgtatgccgtcttctgcttgT<br>TGTCGACTCTAGGGATAACAGGGTAATGAGTCG<br>ACAcaagcagaagacggcatacgagatTGGTCA<br>ACGATAgtctcgtgggctcggagatgtgtataa<br>gagacagGGACAAACAGAAATATCACGctgtct<br>cttatacacatctgacgctgccgacgaATCACC<br>AGGTGTgtgtagatctcggtggtcgccgtatca<br>ttTTGTCGACTC<br>(SEQ ID NO: 6) |
| 236_ILL_<br>size_600_<br>ECO_16S | GAGTCGACAAaatgatacggcgaccaccgagat<br>ctacactctttccctacacgacgctcttccgat<br>ctCAACGGAACGTGCACTGCAGAAATTGAAGAG<br>TTTGATCATGGCTCAGATTGAACGCTGGCGGCA<br>GGCCTAACACATGCAAGTCGAACGGTAACAGGA<br>AGAAGCTTGCTCTTTGCTGACGAGTGGCGGACG<br>GGTGAGTAATGTCTGGGAAACTGCCTGATGGAG<br>GGGGATAACTACTGGAAACGGTAGCTAATACCG<br>CATAACGTCGCAAGACCAAAGAGGGGGACCTTC<br>GGGCCTCTTGCCATCGGATGTGCCCAGATGGGA<br>CTTAGCTAGTAGGTGGGGTAACGGCTCACCTAG<br>GCGACGATCCCTAGCTGGTCTGAGAGGATGACC<br>TAGCCACACTGGAACTGAGACACGGTCCACACA<br>CCTAGGGAGGCAGCAGTGGGGAATATTGCACAA<br>TGGGCGCAAGCCTGATGCAGCCATGCCGCGTGT<br>ATGAAGAAGGCCTTCGGGTGTAAAGTACTTTCA<br>GCGGGGAGGAAGagatcggaagagcacacgtct<br>gaactccagtcacAATCAGTCTCGTatctcgta<br>tgccgtcttctgcttgTTGTCGACTCTAGGGAT<br>aAACAGGGTAATGAGTCGACAAcaagcagaaga<br>cggcatacgagatTGGTCAACGATAgtctcgtgg<br>gctcggagatgtgtataagagacagGGCCACCG<br>TAAACAGTGCGActgtctcttatacacatctga<br>cgctgccgacgaATCACCAGGTGTgtgtagatc<br>tcggtggtcgccgtatcattTTGTCGACTC<br>(SEQ ID NO: 7) |
| 237_ILL_<br>size_750_<br>ECO_16S | GAGTCGACAAaatgatacggcgaccaccgagat<br>ctacactctttccctacacgacgctcttccgat<br>ctAATGTGAGCGTATCAGGAGAAAATTGAAGAG<br>TTTGATCATGGCTCAGATTGAACGCTGGCGGCA<br>GGCCTAACACATGCAAGTCGAACGGTAACAGGA<br>AGAAGCTTGCTCTTTGCTGACGAGTGGCGGACG<br>GGTGAGTAATGTCTGGGAAACTGCCTGATGGAG<br>GGGGATAACTACTGGAAACGGTAGCTAATACCG<br>CATAACGTCGCAAGACCAAAGAGGGGGACCTTC<br>GGGCCTCTTGCCATCGGATGTGCCCAGATGGGA<br>TTAGCTAGTAGGTGGGGTAACGGCTCACCTAGG<br>CGACGATCCCTAGCTGGTCTGAGAGGATGACCA<br>GCCACACTGGAACTGAGACACGGTCCACACACC<br>TACGGGAGGCAGCAGTGGGGAATATTGCACAAT<br>GGGCGCAAGCCTGATGCAGCCATGCCGCGTGTA<br>TGAAGAAGGCCTTCGGGTTGTAAAGTACTTTCA<br>GCGGGGAGGAAGGGAGTAAAGTTAATACCTTTG<br>CTCATTGACGTTACCCGCAGAAGAAGCACCGGC<br>TAACTCCGTGCCAGCAGCCGCGGTAATACGGAG<br>CGGTGCAAGGTTAATCGGAATTACTGGGCGTAA |

TABLE 1-continued

Synthetic Size Standards

| Size Standard | Sequence |
|---|---|
| | AGCGCACGCAGGCGGTTTGTTAAGTCAGATAga<br>tcggaagagcacacgtctgaactccagtcacAA<br>TCAGTCTCGTatctcgtatgccgtcttctgctt<br>gTTGTCGACTCTAGGGATAACAGGGTAATGAGT<br>CGACAAcaagcagaagacggcatacgagatTGG<br>TCAACGATAgtctcgtgggctcggagatgtgta<br>taagagacagTAGCGCCCACAGCAAGTGATctg<br>tctcttatacacatctgacgctgccgacgaATC<br>ACCAGGTGTgtgtagatctcggtggtcgccgta<br>tcattTTGTCGACTC<br>(SEQ ID NO: 8) |
| 238_ILL_<br>size_900_<br>ECO_16S | GAGTCGACAAaatgatacggcgaccaccgagat<br>ctacactctttccctacacgacgctcttccgat<br>ctCGGCGGGTAGTACCTGTACCAAATTGAAGAG<br>TTTGATCATGGCTCAGATTGAACGCTGGCGGCA<br>GGCCTAACACATGCAAGTCGAACGGTAACAGGA<br>AGAAGCTTGCTCTTTGCTGACGAGTGGCGGACG<br>GGTGAGTAATGTCTGGGAAACTGCCTGATGGAG<br>GGGGATAACTACTGGAAACGGTAGCTAATACCG<br>CATAACGTCGCAAGACCAAAGAGGGGGACCTTC<br>GGGCCTCTTGCCATCGGATGTGCCCAGATGGGA<br>TTAGCTAGTAGGTGGGGTAACGGCTCACCTAGG<br>CGACGATCCCTAGCTGGTCTGAGAGGATGACCA<br>GCCACACTGGAACTGAGACACGGTCCACACACC<br>TACGGGAGGCAGCAGTGGGGAATATTGCACAAT<br>GGGCGCAAGCCTGATGCAGCCATGCCGCGTGTA<br>TGAAGAAGGCCTTCGGGTTGTAAAGTACTTTCA<br>GCGGGGAGGAAGGGAGTAAAGTTAATACCTTTG<br>CTCATTGACGTTACCCGCAGAAGAAGCACCGGC<br>TAACTCCGTGCCAGCAGCCGCGGTAATACGGAG<br>GGTGCAAGCGTTAATCGGAATTACTGGGCGTAA<br>AGCGCACGCAGGCGGTTTGTTAAGTCAGATGTG<br>AAATCCCCGGGCTCAACCTGGGAACTGCATCTG<br>ATACTGGCAAGCTTGTCACACGTAGAGGGGGGT<br>AGAATTCCAGGTGTAGCGGTGAAATGCGTAGAG<br>ATCTGGAGGAATACCGGTGGCGAAGGCGGCCCC<br>CTGGACGAAGACTGAagatcggaagagcacacg<br>tctgaactccagtcacAATCAGTCTCGTatctc<br>gtatgccgtcttctgcttgTTGTCGACTCTAGG<br>GATAACAGGGTAATGAGTCGACAAcaagcagaa<br>gacggcatacgagatTGGTCAACGATAgtctcg<br>tgggctcggagatgtgtataagagacagACAAG<br>CCCTAATGATGATAGctgtctcttatacacatc<br>tgacgctgccgacgaATCACCAGGTGTgtgtag<br>atctcggtggtcgccgtatcattTTGTCGACTC<br>(SEQ ID NO: 9) |
| 239_ILL_<br>size_1050_<br>ECO_16S | GAGTCGACAAaatgatacggcgaccaccgagat<br>ctacactctttccctacacgacgctcttccgat<br>ctGTTCTCCTGCTACAGAGGTTAAATTGAAGAG<br>TTTGATCATGGCTCAGATTGAACGCTGGCGGCA<br>CGGCCTAACACATGCAAGTCGAACGGTAACAGG<br>AAGAAGCTTGCTCTTTGCTGAGAGTGGCGGACG<br>GGTGAGTAATGTCTGGGAAACTGCCTGATGGAG<br>GGGGATAACTACTGGAAACGGTAGCTAATACCG<br>CATAACGTCGCAAGACCAAAGAGGGGGACCTTC<br>GGGCCTCTTGCCATCGGATGTGCCCAGATGGGA<br>TTAGCTAGTAGGTGGGGTAACGGCTCACCTAGG<br>CGACGATCCCTAGCTGGTCTGAGAGGATGACCA<br>GCCACACTGGAACTGAGACACGGTCCACACACC<br>TACGGGAGGCAGCAGTGGGGAATATTGCACAAT<br>GGGCGCAAGCCTGATGCAGCCATGCCGCGTGTA<br>TGAAGAAGGCCTTCGGGTTGTAAAGTACTTTCA<br>GCGGGGAGGAAGGGAGTAAAGTTAATACCTTTG<br>CTCATTGACGTTACCCGCAGAAGAAGCACCGGC<br>TAACTCCGTGCCAGCAGCCGCGGTAATACGGAG<br>GGTGCAAGCGTTAATCGGAATTACTGGGCGTAA<br>AGCGCACGCAGGCGGTTTGTTAAGTCAGATGTG<br>AAATCCCCGGGCTCAACCTGGGAACTGCATCTG<br>ATACTGGCAAGCTTGTCACACGTAGAGGGGGGT<br>AGAATTCCAGGTGTAGCGGTGAAATGCGTAGAG<br>AATCTGGAGGAATACCGGTGGCGAAGGCGGCCC<br>CCTGGACGAAGACTGCGCTCAGGTGCGAAAGCG<br>TGGGGAGCAAACAGGATTAGATACCCTGGTAGT |

TABLE 1-continued

Synthetic Size Standards

| Size Standard | Sequence |
|---|---|
| | CCACGCCGTAAACGATGTCGACTTGGAGGTTGT<br>GCCCTTGAGGCGTGGCTTCCGGAGCTAACGCGT<br>TAAGTCGACCGCCTGGGGAGTACGGCCGCAAGG<br>agatcggaagagcacacgtctgaactccagtca<br>cAATCAGTCTCGTatctcgtatgccgtcttctg<br>cttgTTGTCGACTCTAGGGATAACAGGGTAATG<br>AGTCGACAAcaagcagaagacggcatacgagat<br>TGGTCAACGATAgtctcgtgggctcggagatgt<br>gtataagagacagACGCTGATAAATATCGAGTT<br>ctgtctcttatacacatctgacgctgccgacga<br>ATCACCAGGTGTgtgtagatctcggtggtcgcc<br>gtatcattTTGTCGACTC<br>(SEQ ID NO: 10) |
| 240_ILL_<br>size_1200_<br>ECO_16S | GAGTCGACAAaatgatacggcgaccaccgagat<br>ctacactctttccctacacgacgctcttccgat<br>ctCCCACATGCCGGAACGCACCAAATTGAAGAG<br>TTTGATCATGGCTCAGATTGAACGCTGGCGGCA<br>GGCCTAACACATGCAAGTCGAACGGTAACAGGA<br>AGAAGCTTGCTCTTTGCTGACGAGTGGCGGACG<br>GGTGAGTAATGTCTGGGAAACTGCCTGATGGAG<br>GGGGATAACTACTGGAAACGGTAGCTAATACCG<br>ACATAACGTCGCAAGACCAAAGAGGGGGACCTT<br>CGGGCCTCTTGCCATCGGATGTGCCCAGATGGG<br>ATTAGCTAGTAGGTGGGGTACGGCTCACCTAGG<br>CCGACGATCCCTAGCTGGTCTGAGAGGATGACC<br>AGCCACACTGGAACTGAGACACGGTCCACACAC<br>CTACGGGAGGCAGCAGTGGGGAATATTGCACAA<br>TGGGCGCAAGCCTGATGCAGCCATGCCGCGTGTA<br>TGAAGAAGGCCTTCGGGTTGTAAAGTACTTTCA<br>GCGGGGAGGAAGGGAGTAAAGTTAATACCTTTG<br>CTCATTGACGTTACCCGCAGAAGAAGCACCGGC<br>TAACTCCGTGCCAGCAGCCGCGGTAATACGGAG<br>GGTGCAAGCGTTAATCGGAATTACTGGGCGTAA<br>AGCGCACGCAGGCGGTTTGTTAAGTCAGATGTG<br>AAATCCCCGGGCTCAACCTGGGAACTGCATCTG<br>ATACTGGCAAGCTTGTCACACGTAGAGGGGGT<br>AGAATTCCAGGTGTAGCGGTGAAATGCGTAGAG<br>ATCTGGAGGAATACCGGTGGCGAAGGCGGCCCC<br>TCTGGACGAAGACTGACGCTCAGGTGCGAAAGC<br>GTGGGGAGCAAACAGGATTAGACCCTGGTAGT<br>CCACGCCGTAAACGATGTCGACTTGGAGGTTGT<br>GGCCCTTGAGGCGTGGCTTCCGGAGCTAACGCG<br>TTAAGTCGACCGCCTGGGGAGTACGGCCGCAAG<br>GTTAAAACTCAAATAATTGACGGGGGCCCGCAC<br>TAAGCGGTGGAGCATGTGGTTTAATTCGATGCA<br>GACGCGAAGAACCTTACCTGGTCTTGACATCCA<br>CGGAAGTTTTCAGAGATGAGAATGTGCCTTCGG<br>GAACCGGAGACAGGTGCTGagatcggaagagca<br>cacgtctgaactccagtcacAATCATCTCGTat<br>ctcgtatgccgtcttctgcttgTTGTCGACTCT<br>AGGGATAACAGGGTAATGAGTCGACAAcaagca<br>gaagacggcatacgagatTGGTCAACGATAgtc<br>tcgtgggctcggagatgtgtataagagacagTC<br>GTTCTAAGAGGGTGCCAGctgtctcttatacac<br>atctgacgctgccgacgaATCACCAGGTGTgtg<br>tagatctcggtggtcgccgtatcattTTGTCGA<br>CTC<br>(SEQ ID NO: 11) |
| 241_ILL_<br>size_1350_<br>ECO_16S | GAGTCGACAAaatgatacggcgaccaccgagat<br>ctacactctttccctacacgacgctcttccgat<br>ctCCCAAACGTCGGAAAGGTCTAAATTGAAGAG<br>TTTGATCATGGCTCAGATTGAACGCTGGCGGCA<br>GGCCTAACACATGCAAGTCGAACGGTAACAGGA<br>AGAAGCTTGCTCTTTGCTGACGAGTGGCGGACG<br>GGTGAGTAATGTCTGGGAAACTGCCTGATGGAG<br>GGGGATAACTACTGGAAACGGTAGCTAATACCG<br>ACATAACGTCGCAAGACCAAAGAGGGGGACCTT<br>CGGGCCTCTTGCCATCGGATGTGCCCAGATGGG<br>CATTAGCTAGTAGGTGGGGTACGGCTCACCTAG<br>GCGACGATCCCTAGCTGGTCTGAGAGGATGACC<br>AGCCACACTGGAACTGAGACACGGTCCACACAC<br>CTAGGGAGGCAGCAGTGGGGAATATTGCACAAT<br>GGGCGCAAGCCTGATGCAGCCATGCCGCGTGTA |

TABLE 1-continued

Synthetic Size Standards

| Size Standard | Sequence |
|---|---|
| | TGAAGAAGGCCTTCGGGTTGTAAAGTACTTTCA<br>GCGGGGAGGAAGGGAGTAAAGTTAATACCTTTG<br>CTCATTGACGTTACCCGCAGAAGAAGCACCGGC<br>TAACTCCGTGCCAGCAGCCGCGGTAATACGGAG<br>GGTGCAAGCGTTAATCGGAATTACTGGGCGTAA<br>AGCGCACGCAGGCGGTTTGTTAAGTCAGATGTG<br>AAATCCCCGGGCTCAACCTGGGAACTGCATCTG<br>ATACTGGCAAGCTTGTCACACGTAGAGGGGGT<br>AGAATTCCAGGTGTAGCGGTGAAATGCGTAGAG<br>AATCTGGAGGAATACCGGTGGCGAAGGCGGCCC<br>CCTGGACGAAGACTGCGCTCAGGTGCGAAAGCG<br>TGGGGAGCAAACAGGATTAGATACCCTGGTAGT<br>CCACGCCGTAAACGATGTCGACTTGGAGGTTGT<br>GCCCTTGAGGCGTGGCTTCCGGAGCTAACGCGT<br>TAAGTCGACCGCCTGGGGAGTACGGCCGCAAGG<br>TTAAAACTCAAATGAATTGACGGGGGCCCGCAC<br>AAGCGGTGGAGCATGTGGTTTAATTCGATGCAA<br>CGCGAAGAACCTTACCTGGTCTTGACATCCACG<br>GAAGTTTTCAGAGATGAGAATGTGCCTTCGGGA<br>ACCGTGAGACAGGTGCTGCATGGCTGTCGTCAG<br>CTCGTGTTGTGAAAGTTGGGTTAAGTCCCGCAA<br>CGAGCGCAACCCTTATCCTTTGTTGCCAGCGGT<br>CCGGCCGGGAACTCAAAGGAGACTGCCAGTGA<br>TAAACTGGAGGAAGGTGGGGATGACGTCAAGTC<br>ATCagatcggaagagcacacgtctgaactccag<br>tcacAATCAGTCTCGTatctcgtatgccgtctt<br>ctgcttgTTGTCGACTCTAGGGATAACAGGGTA<br>ATGAGTCGACAAcaagcagaagacggcatacga<br>gatTGGTCAACGATAgtctcgtgggctcggaga<br>tgtgtataagagacagTGCAACTCAACGGTCCC<br>AGGCtgtctcttatacacatctgacgctgccga<br>cgaATCACCAGGTGTgtgtagatctcggtggtc<br>gccgtatcattTTGTCGACTC<br>(SEQ ID NO: 12) |
| 242_ILL_<br>size_1500_<br>ECO_16S | GAGTCGACAAaatgatacggcgaccaccgagat<br>ctacactctttccctacacgacgctcttccgat<br>ctAACCAGAGGATGAGACACGTAAATTGAAGAG<br>TTTGATCATGGCTCAGATTGAACGCTGGCGGCA<br>GGCCTAACACATGCAAGTCGAACGGTAACAGGA<br>AGAAGCTTGCTCTTTGCTGACGAGTGGCGGACG<br>GGTGAGTAATGTCTGGGAAACTGCCTGATGGAG<br>GGGGATAACTACTGGAAACGGTAGCTAATACCG<br>CATAACGTCGCAAGACCAAAGAGGGGGACCTTC<br>GGGCCTCTTGCCATCGGATGTGCCCAGATGGGA<br>TTAGCTAGTAGGTGGGGTAACGGCTCACCTAGG<br>CGACGATCCCTAGCTGGTCTGAGAGGATGACCA<br>GCCACACTGGAACTGAGACACGGTCCACACACC<br>TACGGGAGGCAGCAGTGGGGAATATTGCACAAT<br>GGGCGCAAGCCTGATGCAGCCATGCCGCGTGTA<br>TGAAGAAGGCCTTCGGGTTGTAAAGTACTTTCA<br>GCGGGGAGGAAGGGAGTAAAGTTAATACCTTTG<br>CTCATTGACGTTACCCGCAGAAGAAGCACCGGC<br>TAACTCCGTGCCAGCAGCCGCGGTAATACGGAG<br>GGTGCAAGCGTTAATCGGAATTACTGGGCGTAA<br>AGCGCACGCAGGCGGTTTGTTAAGTCAGATGTG<br>AAATCCCCGGGCTCAACCTGGGAACTGCATCTG<br>TATACTGCCAAGCTTGTCACACGTAGAGGGGGG<br>AGAATTCCAGGTGTAGCGGTGAAATGCGTAGAG<br>AATCTGGAGGAATACCGGTGGCGAAGGCGGCCC<br>CCTGGACGAAGACTGCGCTCAGGTGCGAAAGCG<br>TTGGGGAGCAAACAGGATTAGATACCCTGGTAG<br>TCCACGCCGTAAACGATGTCGACTTGGAGGTGT<br>GCCCTTGAGGCGTGGCTTCCGGAGCTAACGCGT<br>ATAAGTCGACCGCCTGGGGAGTACGGCCGCAAG<br>CGTTAAAACTCAAATGAATTGACGGGGGCCCGC<br>ACAAGCGGTGGAGCATGTGGTTTATTCGATGCA<br>AACGCGAAGAACCTTACCTGGTCTTGACATCAC<br>GGAAGTTTTCAGAGATGAGAATGTGCCTTCGGG<br>AACCGTGAGACAGGTGCCATGGCTGTCGTCA<br>GCTCGTGTTGTGAATGTTGGGTTAAGTCCCGCA<br>ACGAGCGCAACCCTTATCCTTTGTTGCCAGCGG<br>TCCGGCCGGGAACTCAAAGGAGACTGCCAGTGA<br>TAAACTGGAGGAAGGTGGGGATGACGTCAAGTC<br>ATCATGGCCCTTACGACCAGGGCTACACACGTG |

TABLE 1 -continued

Synthetic Size Standards

| Size Standard | Sequence |
|---|---|
| | CTACAATGGCGCATACAAAGAGAAGCGACCTCG<br>CGAGAGCAAGCGGACCTCATAAAGTGCGTCGTA<br>GTCCGGATTGGTGACTGCAACTCCACACCATGA<br>AGTCGGAATCGCTAGTAATCGagatcggaagag<br>cacacgtctgaactccagtcacAATCAGTCTCG<br>TatctcgtatgccgtcttctgcttgTTGTCGAC<br>TCTAGGGATAACAGGGTAATGAGTCGACAAca<br>agcagaagacggcatacgagatTGGTCAACGATA<br>gtctcgtgggctcggagatgtgtataagagaca<br>gTGGCTCCTTCTGTTAAGGCActgtctcttata<br>cacatctgacgctgccgacgaATCACCAGGTGT<br>gtgtagatctcggtggtcgccgtatcattTTGT<br>CGACTC<br>(SEQ ID NO: 13) |
| 243_ILL_<br>size_150_<br>GAPDH | GAGTCGACAAaatgatacggcgaccaccgagat<br>ctacactctttccctacacgacgctcttccgat<br>ctCCACCTAACAGACACTTGTTAGagatcggaa<br>gagcacacgtctgaactccagtcacAATCAGTC<br>TCGTatctcgtatgccgtcttctgcttgTTGTC<br>GACTCTAGGGATAACAGGGTAATGAGTCGACAA<br>caagcagaagacggcatacgagatTGGTCAACG<br>ATAgtctcgtgggctcggagatgtgtataagag<br>acagGGTAAGTAGTGCGTGAGGGTctgtctctt<br>atacacatctgacgctgccgacgaATCACCAGG<br>TGTgtgtagatctcggtggtcgccgtatcattT<br>TGTCGACTC<br>(SEQ ID NO: 14) |
| 244_ILL_<br>size_300_<br>GAPDH | GAGTCGACAAaatgatacggcgaccaccgagat<br>ctacactctttccctacacgacgctcttccgat<br>ctGCGCCCTGGCGCCGGCCAGGTTTTTAAGGCG<br>CTTATATAATCAAACCCTTTGTAAAAATTAAAG<br>TTTTAAATGGAATTCTAATCGATTTATTTCACA<br>TTAGCTTTATTTAAGTGTGACCTACGCAGAAAG<br>CTAGCGAAATACTCATCAACCCTCCCCCGCCAT<br>CGCAGCGCCagatcggaagagcacacgtctgaa<br>ctccagtcacAATCAGTCTCGTatctcgtatgc<br>cgtcttctgcttgTTGTCGACTCTAGGGATAA<br>CAGGGTAATGAGTCGACAAcaagcagaagacgg<br>catacgagatTGGTCAACGATAgtctcgtgggc<br>tcggagatgtgtataagagacagACGGAGTAGT<br>ACGGTCAAATtgtctcttatacacatctgacgc<br>tgccgacgaATCACCAGGTGTgtgtagatctcg<br>gtggtcgccgtatcattTTGTCGACTC<br>(SEQ ID NO: 15) |
| 245_ILL_<br>size_450_<br>GAPDH | GAGTCGACAAaatgatacggcgaccaccgagat<br>ctacactctttccctacacgacgctcttccgat<br>ctCTACTAAACAATAATGGGAATTriTTAAGGCG<br>CTTATATAATCAAACCCTTTGTAAAAATTAAAG<br>TTTTAAATGGAATTCTAATCGATTTATTTCACA<br>TTAGCTTTATTTAAGTGTGACCTACGCAGAAAG<br>CTAGCGAAATACTCATCAACCCTCCCCCGCCAT<br>CGCAGCGCCATTCTCCTAATTTGCGAAAAAAGC<br>TCCGGGAAAAGGAAAAAGCGGCAGTCGTAATAG<br>CGAACTGAAACTGAACGAGAGTAAAAGTGAAAA<br>GACAGCAGGAACTCAGCCATGTCGAAGATCGGA<br>AcaagcagaagacggcatacgagatTGGTCAAC<br>GAATTAACGGATTTGGCCGCATCGGCCGcagat<br>cggaagagcacacgtctgaactccagtcacAAT<br>CAGTCTCGTatctcgtatgccgtcttctgcttg<br>TTGTCGACTCTAGGGATAACAGGGTAATGAGTC<br>GACATAgtctcgtgggctcggagatgtgtataa<br>gagacagGGATTGCCACACGCGATAGActgtct<br>cttatacacatctgacgctgccgacgaATCACC<br>AGGTGTgtgtagatctcggtggtcgccgtatca<br>ttTTGTCGACTC<br>(SEQ ID NO: 16) |
| 246_ILL_<br>size_600_<br>GAPDH | GAGTCGACAAaatgatacggcgaccaccgagat<br>ctacactctttccctacacgacgctcttccgat<br>ctCTGTGTTCGGCCTTCGAGATTTTTTAAGGCG<br>CTTATATAATCAAACCCTTTGTAAAAATTAAAG<br>TTTTAAATGGAATTCTAATCGATTTATTTCACA |

TABLE 1 -continued

Synthetic Size Standards

| Size Standard | Sequence |
|---|---|
| | TTAGCTTTATTTAAGTGTGACCTACGCAGAAAG<br>CTAGCGAAATACTCATCAACCCTCCCCCGCCAT<br>CGCAGCGCCATTCTCCTAATTTGCGAAAAAAGC<br>GTCCGGGAAAAGGAAAAAGCGGCAGTCGTAATA<br>GCGAACTGAAACTGAACGAGAGTAAAAGTGAAA<br>AGACAGCAGGAACTCAGCCATTCGAAGATCGGA<br>ATTAACGGATTTGGCCGCATCGGCCGCTTGGTG<br>CTCCGCGCCGCCATCGATAAGGGCGCCTCCGTG<br>GTGGCCGTCAACGATCCCTTCATCGATGTCAAC<br>TACATGGTTTACCTGTTTAAATTCCACACCACA<br>CACGGTCGTTTCAAGGGCACCGTTGCGGCTGAG<br>GGCGGATTCTGagatcggaagagcacacgtct<br>gaactccagtcacAATCAGTCTCGTatctcgta<br>tgccgtcttctgcttgTTGTCGACTCTAGGGAT<br>AACAGGGTAATGAGTCGACAAcaagcagaagac<br>ggcatacgagatTGGTCAACGATAgtctcgtgg<br>gctcggagatgtgtataagagacagTAGTGTTT<br>AAGTGCGAACCTctgtctcttatacacatctga<br>cgctgccgacgaATCACCAGGTGTgtgtagatc<br>tcggtggtcgccgtatcattTTGTCGACTC<br>(SEQ ID NO: 17) |
| 247_ILL_<br>size_750_<br>GAPDH | GAGTCGACAAaatgatacggcgaccaccgagat<br>ctacactctttccctacacgacgctcttccgat<br>ctTATGAAATCGGAGTATCAGTTTTTTAAGGCG<br>CTTATATAATCAAACCCTTTGTAAAAATTAAAG<br>TTTTAAATGGAATTCTAATCGATTTATTTCACA<br>TTAGCTTTATTTAAGTGTGACCTACGCAGAAAG<br>CTAGCGAAATACTCATCAACCCTCCCCCGCCAT<br>CGCAGCGCCATTCTCCTAATTTGCGAAAAAAGC<br>TCCGGGAAAAGGAAAAAGCGGCAGTCGTAATAG<br>CGAACTGAAACTGAACGAGAGTAAAAGTGAAAA<br>GACAGCAGGAACTCAGCCATGTCGAAGATCGGA<br>CATTAACGGATTTGGCCGCATCGGCCGCTTGGT<br>GCTCCGCGCCGCCATCGATAAGGGCGCCTCCGT<br>GGTGGCCGTCAACGATCCCTTCATCGATGTCAA<br>CTACATGGTTTACTGTTTAAATTCCACACCACA<br>CACGGTCGTTTCAAGGGCACCGTTGCGGCTGAG<br>GGCGGATTCCTGGTGGTGAACGGCAGAAGATC<br>GACCGTGTTCAGCGAGCGCGACCCGGCCAACAT<br>CAACTGGGCCAGTGCTGGAGCCGAGTATGTTGGT<br>GGTGACCACCGGAGTGTTCACCACCATTGACAA<br>GGCGTCCACCCACTTGAAGGGCGGCGCCAAGag<br>atcggaagagcacacgtctgaactccagtcacA<br>ATCAGTCTCTatctcgtatgccgtcttctgctt<br>gTTGTCGACTCTAGGGATAACAGGGTAATGAGT<br>CGACAAcaagcagaagacggcatacgagatTGG<br>TCAACGATAgtctcgtgggctcggagatgtgta<br>taagagacagAAGAGCCCTGCCTCAAGTCCctg<br>tctcttatacacatctgacgctgccgacgaATC<br>ACCAGGTGTgtgtagatctcggtggtcgccgta<br>tcattTTGTCGACTC (SEQ ID NO: 18) |
| 248_ILL_<br>size_900_<br>GAPDH | GAGTCGACAAaatgatacggcgaccaccgagat<br>ctacactctttccctacacgacgctcttccgat<br>ctAGCCAAACGTCTGAACAGATTTTTAAGGCG<br>CTTATATAATCAAACCCTTTGTAAAAATTAAAG<br>TTTTAAATGGAATTCTAATCGATTTATTTCACA<br>TTAGCTTTATTTAAGTGTGACCTACGCAGAAAG<br>CTAGCGAAATACTCATCAACCCTCCCCCGCCAT<br>CGCAGCGCCATTCTCCTAATTTGCGAAAAAAGC<br>TCCGGGAAAAGGAAAAAGCGGCAGTCGTAATAG<br>CGAACTGAAACTGAACGAGAGTAAAAGTGAAAA<br>GACAGCAGGAACTCAGCCATGTCGAAGATCGGA<br>ATTAACGGATTTGGCCGCATCGGCCGCTTGGTG<br>CTCCGCGCCGCCATCGATAAGGGCGCCTCCGTG<br>GTGGCCGTCAACGATCCCTTCATCGATGTCAAC<br>TACATGGTTTACCTGTTTAAATTCCACACCACA<br>CACGGTCGTTTCAAGGGCACCGTTGCGGCTGAG<br>GGCGGATTCCTGGTGGTGAACGGCAGAAGATC<br>CACCGTGTTCAGCGAGCGCGACCCGGCCAACAT<br>CAACTGGGCCAGTGCTGGAGCCGAGTATGTTGGT<br>GGTGACCACCGGAGTGTTCACCACCATTGACAA<br>GGCGTCCACCCACTTGAAGGGCGGCGCCAAGAA<br>GGTCATCATCTCGGCCCCATCCGCCGATGGCCC |

TABLE 1 -continued

Synthetic Size Standards

| Size Standard | Sequence |
|---|---|
| | ATGTTCGTGTGCGGCGTTAACCTGGACGCCTAC<br>AGCCCCGACATGAAGGTGGTCTCCAACGCCTCG<br>TGCACCACCAACTGCCTGGCTCCCCTGGCCAAG<br>GTCATCAATGACAACagatcggaagagcacacg<br>tctgaactccagtcacAATCAGTCTCGTatctc<br>gtatgccgtcttctgcttgTTGTCGACTCTAGG<br>GATAACAGGGTAATGAGTCGACAAcaagcagaa<br>ggacggcatacgagatTGGTCAACGATAgtctc<br>gtgggctcggagatgtgtataagagacagCCGT<br>GTCGAACGCCACTCGActgtctcttatacacat<br>ctgacgctgccacgaATCACCAGGTGTgtgtag<br>atctcggtggtcgccgtatcattTTGTCGACTC<br>(SEQ ID NO: 19) |
| 249_ILL_<br>size_1050_<br>GAPDH | GAGTCGACAAaatgatacggcgaccaccgagat<br>ctacactctttccctacacgacgctcttccgat<br>ctCAAGTCCAGGGCACTCGCCTHTITAAGGCGC<br>TTATATAATCAAACCCTTTGTAAAAATTAAAGT<br>TTTTAAATGGAATTCTAATCGATTTATTTCACAT<br>TAGCTTTATTTAAGTGTGACCTACGCAGAAAGC<br>TAGCGAAATACTCATCAACCCTCCCCCGCCATC<br>GCAGCGCCATTCTCCTAATTTGCGAAAAAAGCT<br>CCGGGAAAAGGAAAAAGCGGCAGTCGTAATAGC<br>GAACTGAAACTGAACGAGAGTAAAAGTGAAAAG<br>ACAGCAGGAACTCAGCCATGTCGAAGATCGGAA<br>TTAACGGATTTGGCCGCATCGGCCGCTTGGTGC<br>TCCGCGCCGCCATCGATAAGGGCGCCTCCGTGG<br>TGGCCGTCAACGATCCCTTCATCGATGTCAACT<br>ACATGGTTTACCTGTTTAAATTCCACACCACAC<br>ACGGTCGTTTCAAGGGCACCGTTGCGGCTGAGG<br>CGCGGATTCCTGGTGGTGAACGGCCAGAAGATC<br>ACCGTGTTCAGCGAGCGCGACCCGGCCAACATC<br>AACTGGGCCAGTGCTGGAGCCGAGTATGTGGTG<br>GTGACCACCGGAGTGTTCACCACCATTGACAAG<br>GCGTCCACCCACTTGAAGGGGGCGCCAAGAAGG<br>TCATCATCTCGGCCCCATCCGCCGATGCGCCCA<br>TGTTCGTGTGCGGCGTTAACCTGGACGCCTACA<br>GCCCCGACATGAAGGTGGTCTCCAACGCCCGT<br>GCACCACCAACTGCCTGGCTCCCCTGGCCAAGG<br>TCATCAATGACAACTTCGAGATCGTCGAGGGTC<br>TGATGACCACCGTGCACGCCACCACTGCCACCC<br>AGAAGACCGTCGACGGTCCCTCTGGCAAACTGT<br>GGCGCGATGGACGTGGCGCCGCCCAGAACATCA<br>TCCCCGGCCGCCACCGGAGCCGCCAAGGCTGTGa<br>Ggatcggaagagcacacgtctgaactccagtca<br>cAATCAGTCTCGTatctcgtatgccgtcttctg<br>TcttgTTGTCGACTCTAGGGATAACAGGGTAATG<br>AGTCGACAAcaagcagaagacggcatacgagat<br>TGGTCAACGATAgtctcgtgggctcggagatgt<br>gtataagagacagTATGCCAGGGCTTTCGAACc<br>tgtctcttatacacatctgacgctgccgacgaA<br>TCACCAGGTGTgtgtagatctcggtggtcgccg<br>tatcattTTGTCGACTC<br>(SEQ ID NO: 20) |
| 250_ILL_<br>size_1200_<br>GAPDH | GAGTCGACAAaatgatacggcgaccaccgagat<br>ctacactctttccctacacgacgctcttccgat<br>ctAtATTTCTACTCATAGGTTCATTTTTTAAGGC<br>GCTTATTAATCAAACCCTTTGTAAAAATTAAAG<br>TTTTAAATGGAATTCTAATCGATTTATTTCACA<br>TTAGCTTTATTTAAGTGTGACCTACGCAGAAAG<br>CTAGCGAAATACTCATCAACCCTCCCCCGCCAT<br>CGCAGCGCCATTCTCCTAATTTGCGAAAAAAGC<br>TCCGGGAAAAGGAAAAAGCGGCAGTCGTAATAG<br>CGAACTGAAACTGAACGAGAGTAAAAGTGAAAA<br>GACAGCAGGAACTCAGCCATGTCGAAGATCGGA<br>ATTAACGGATTTGGCCGCATCGGCCGCTTGGTG<br>CTCCGCGCCGCCATCGATAAGGGCGCCTCCGTG<br>GTGGCCGTCAACGATCCCTTCATCGATGTCAAC<br>TACATGGTTTACCTGTTTAAATTCCACACCACA<br>CACGGTCGTTTCAAGGGCACCGTTGCGGCTGA<br>GGCGGATTCCTGGTGGTGAACGGCCAGAAGAT<br>CACCGTGTTCAGCGAGCGCGACCCGGCCAACAT<br>CAACTGGCCAGTGCTGGAGCCGAGTATGTGGTG<br>GTGACCACCGGAGTGTTCACCACCATTGACAAG |

TABLE 1 -continued

Synthetic Size Standards

| Size Standard | Sequence |
|---|---|
| | GCGTCCACCCACTTGAAGGGCGGCGCCAAGAAG<br>GTCATCATCTCGGCCCCATCCGCCGATGCGCCC<br>ATGTTCGTGTGCGGCGTTAACCTGGACGCCTAC<br>AGCCCCGACATGAAGGTGGTCTCCAACGCCTCG<br>TGCACCACCAACTGCCTGGCTCCCCTGGCCAAG<br>GTCATCAATGACAACTTCGAGATCGTCGAGGGT<br>CTGATGACCACCGTGCACGCCACCACTGCCACC<br>GCGCGATGGACGTGGCGCCGCCCAGAACATCAT<br>CCCCAGAAGACCGTCGACGGTCCCTCTGGCAAA<br>CTGTGCGGCCGCACCGGAGCCGCCAAGGCTGTG<br>GGCAAGGTCATCCCCGCCCTGAACGGCAAGCTG<br>GACCGGCCATGGCTTTCCGCGTGCCCACGCCCAA<br>TGTCTCCGTTGTGGATCTTACCGTCCGCTTGGG<br>TCAAGGAGCCACCTATGACGAAATCAAGGCTAA<br>GGTCGAGGAGGCCTCCAAGAgatcggaagagca<br>cacgtctgaactccagtcacAATCAGTCTCGat<br>ctcgtatgccgtcttctgcttgTTGTCGACTCT<br>AGGGATAACAGGGTAATGAGTCGACAAcaagca<br>gaagacggcatacgagatTGGTCAACGATAgtc<br>tcgtgggctcggagatgtgtataagagacagTT<br>AGATCAGATAGAAGGTACctgtctcttatacac<br>atctgacgctgccgacgaATCACCAGGTGTgtg<br>tagatctcggtggtcgccgtatcaltTTGTCGA<br>CTC (SEQ ID NO: 21) |
| 251_ILL_<br>size_1350_<br>GAPDH | GAGTCGACAAaatgatacggcgaccaccgagat<br>ctacactctttccctacacgacgctcttccgat<br>ctTTAAGACTGTTAGTTCGAGGTTTTTAAGGCG<br>CCTTATATAATCAAACCCTTTGTAAAAATTAAA<br>GTTTTAAATGGAATTTAATCGATTTATTTCACA<br>TTAGCTTTATTTAAGTGTGACCTACGCAGAAAG<br>CTAGCGAAATACTCATCAACCCTCCCCCGCCAT<br>CGCAGCGCCATTCTCCTAATTTGCGAAAAAAGC<br>TCCGGGAAAAGGAAAAAGCGGCAGTCGTAATAG<br>CGAACTGAAACTGAACGAGAGTAAAAGTGAAAA<br>GACAGCAGGAACTCAGCCATGTCGAAGATCGGA<br>ATTAACGGATTTGGCCGCATCGGCCGCTTGGTG<br>CTCCGCGCCGCCATCGATAAGGGCGCCTCCGTG<br>GTGGCCGTCAACGATCCCTTCATCGATGTCAAC<br>TACATGGTTTACCTGTTTAAATTCCACACCACA<br>CACGGTCGTTTCAAGGGCACCGTTGCGGCTGAG<br>GGCGGATTCCTGGTGGTGAACGGCCAGAAGATC<br>ACCGTGTTCAGCGAGCGCGACCCGGCCAACATC<br>AACTGGGCCAGTGCTGGAGCCGAGTATGTGGTG<br>GTGACCACCGGAGTGTTCACCACCATTGACAAG<br>GCGTCCACCCACTTGAAGGGCGGCGCCAAGAAG<br>GTCATCATCTCGGCCCCATCCGCCGATGCGCCC<br>ATGTTCGTGTGCGGCGTTAACCTGGACGCCTAC<br>AGCCCCGACATGAAGGTGGTCTCCAACGCCTCG<br>AGATCGTCGAGGGTCTGATGACCACCGTGCACG<br>CTGCACCACCAACTGCCTGGCTCCCCTGGCCAA<br>GGTCATCAATGACAACTTCGCACCACTGCCACC<br>CAGAAGACCGTCGACGGTCCCTCTGGCAAACTG<br>TGGCGCGATGGACGTGGCGCCGCCCAGAACATC<br>ATCCCCGGCCGCCACCGGAGCCGCCAAGGCTGTG<br>GGCAAGGTCATCCCCGCCCTGAACGGCAAGCTG<br>ACCGGCATGGCTTTCCGCGTGCCCACGCCCAAT<br>GTCTCCGTTGTGGATCTTACCGTCCGCTTGGGC<br>AAGGGAGCCACCTATGACGAAATCAAGGCTAAG<br>GTCGAGGAGGCCTCCAAGGGACCCCTGAAGGGA<br>ATCCTGGGCTACACCGATGAGGAGGTGGTCTCC<br>ACCGACTTCTTCAGCGACACCCATTCGTCTGTG<br>TTCGACGCCAAGGCTGGCATTTCGCTGAACGAT<br>AAGTTCGTCAAGCTAATCTCGTGGTACGACAAC<br>GAGagatcggaagagcacacgtctgaactccag<br>tcacAATCAGTCTCGTatctcgtatgccgtctt<br>ctgcttgTTGTCGACTCTAGGGATAACAGGGTA<br>ATGAGTCGACAAcaagcagaagacggcatacga<br>gatTGGTCAACGATAgtctcgtgggctcggaga<br>tgtgtataagagacagTTTATATrGTTCTGCCT<br>CACctgtctcttatacacatctgacgctgccga<br>cgaATCACCAGGTGTgtgtagatctcggtggtc<br>gccgtatcattTTGTCGACTC<br>(SEQ ID NO: 22) |

TABLE 1 -continued

Synthetic Size Standards

| Size Standard | Sequence |
|---|---|
| 252_ILL_size_1500_GAPDH | GAGTCGACAAaatgatacggcgaccaccgagatctacactctttccctacacgacgctcttccgatctAGTTACTGGCTTTGTAGGATnTITAAGGCGCTTATATAATCAAACCCTTTGTAAAAATTAAAGTTTTAAAATGGAATTCTAATCGATTTATTTCACATTAGCTTTATTTAAGTGTGACCTACGCAGAAAGCTAGCGAAATACTCATCAACCCTCCCCCGCCATCGCAGCGCCATTCTCCTAATTTGCGAAAAAGCTCCGGGAAAAGGAAAAAGCGGCAGTCGTAATAGCGAACTGAAACTGAACGAGAGTAAAAGTGAAAAGACAGCAGGAACTCAGCCATGTCGAAGATCGGAATTAACGGATTTGGCCGCATCGGCCGCTTGGTGCGTTGCGGCTGAGGGCGGATTCCTGGTGGTGAACTCCGCGCCGCCATCGATAAGGGCGCCTCCGTGGTGGCCGTCAACGATCCCTTCATCGATGTCAACTACATGGTTTACCTGTTTAAATTCCACACCACACACGGTCGTTTCAAGGGCACCGGCCAGAAGATCACCGTGTTCAGCGAGCGCGACCCGGCCAACATCAACTGGGCCAGTGCTGGAGCCGAGTATGTGGTGGTGACCACCGGAGTGTTCACCACCATTGACAAGGCGTCCACCCACTTGAAGGGCGGCGCCAAGAAGGTCATCATCTCGGCCCCATCCGCCGATGCGCCCAGTGTTCGTGTGCGGCGTTAACCTGGACGCCTACAGCCCCGACATGAAGGTGGTCTCCAACGCCTCGTGCACCACCAACTGCCTGGCTCCCCTGGCCAAGGTCATCAATGACAACTTCGAGATCGTCGAGGGTCTGATGACCACCGTGCACGCCACCACTGCCACCCAGAAGACCGTCACGGTCCCTCTGGCAAACTGTTGCGCGATGGACGTGGCGCCGCCCAGAACATCATCCCCGCCGCCACCGGAGCCGCCAAGGCTGTGGGCAAGGTCATCCCCGCCCTGAACGGCAAGCTGACCGGCATGGCTTTCCGCGTGCCCACGCCCAATGTCTCCGTTGTGGATCTTACCGTCCGCTTGGGCAAGGGAGCCACCTATGACGAAATCAAGGCTAAGGTCGAGGAGGCCTCCAAGGGACCCCTGAAGGGAATCCTGGGCTACACCGAGAGGAGGTGGTCTCCACCGACTTCTTCAGCGACACACCCATTCGTCTGTGTTCGACGCCAAGGCTGGCATTTCGCTGAACGATAAGTTCGTCAAGCTAATCTCGTGGTACGACAACGAGTTCGGTTACTCCAACCGCGTCATCGACCTGATCAAGTATATGCAGGACAAGGACTAAACTAGCCAAAACTATCGTACAAACCCGGCGCCCAGCAGCTGGTCGGGAATCACTGTTGCATAATCCGCAAGGGGCGCAATTGAGGATGCTTTTagatcggaagagcacacgtctgaactccagtcacAATCAGTCTCGTatctcgtatgccgtcttctgcttgTTGTCGACTCTAGGGATAACAGGGTAATGAGTCGACAAcaagcagaagacggcatacgagatTGGTCAACGATAgtctcgtgggctcggagatgtgtataagagacagTGTGGCTCCAATTGCTGCAActgtctcttatacacatctgacgctgccgacgaATCACCAGGTGTgtgtagatctcggtggtcgccgtatcattTTGTCGACTC<br>(SEQ ID NO: 23) |
| 253_ILL_size_150_TUB | GAGTCGACAAaatgatacggcgaccaccgagatctacactctttccctacacgacgctcttccgatctAACGGTTTGATGGGCCTGGTATCagatcggaaTgagcacacgtctgaactccagtcacAATCAGTCTCGTatctcgtatgccgtcttctgcttgTTGTCGACCTAGGGATAACAGGGTAATGAGTCGACAAcaagcagaagacggcatacgagatTGGTCAACGATAgtctcgtgggctcggagatgtgtataagagacagCACGCGTACGTGCTATCTTCctgtctcttatacacatctgacgctgccgacgaATCACCAGGTGtgtgtagatctcggtggtcgccgtatcattTTGTCGACTC<br>(SEQ ID NO: 24) |
| 254_ILL_size_300_TUB | GAGTCGACAAaatgatacggcgaccaccgagatctacactctttccctacacgacgctcttccgatctCGTTGTGTTTGCTGGCGCAATCATATTCGTTCTTACGTTTGTCAAGCCTCATAGCCGGCAGTTCGAACGTATACGCTCTTGTGACAGACCTCGAAATCGTAGCTCTACACAATTCTGTGAATTTTCCTTGTCGCGTGTGAAACACTTCCAATAAAAACTCAATATGCGTGAAagatcggaagagcacacgtctgaactccagtcacAATCAGTCTCGTatctcgtatgccgtcttctgcttgTTGTCGACTCTAGGGATAACAGGGTAATGAGTCGACAAcaagcagaagacggcatacgagatTGGTCAACGATAgtctcgtgggctcggagatgtgtataagagacagTCGCGACCAAATGGTCAGTCtgtctcttatacacatctgacgctgccgacgaATCACCAGGTGTgtgtagatctcggtggtcgccgtatcattTTGTCGACTC<br>(SEQ ID NO: 25) |
| 255_ILL_size_450_TUB | GAGTCGACAAaatgatacggcgaccaccgagatctacactctttccctacacgacgctcttccgatctGGCTGACGGTTGAGAGGGATTCATATTCGTTTTACGTTTGTCAAGCCTCATAGCCGGCAGTTCGAACGTATACGCTCTCTGTGACAGACCTCGAAATCGTAGCTCTAGACAATTCTGTGAATTTTCCTTGTCGCGTGTGAAACACTTCCAATAAAAACTCAATATGCGTGAATGTATCTCTATCCATGTTGGTCAGGCTGGTGTCCAGATTGGAAACGCCTGCTGGGAGCTCTACTGCTTGGAGCACGGCATCCAGCCCGATGGCCAGATGCCGTCTGACAAGACCGTGGGCGGAGGTGATCACCGTTCAACACCTTCTTCAGatcgcggaagagcacacgtctgaactccagtcacAATCAGTCTCGTatctcgtatgccgtcttctgcttgTTGTCGACTCTAGGGATAACAGGGTAATGAGTCGACAAcaagcagaagacggcatacgagatTGGTCAACGATAgtctcgtgggctcggagatgtgtataagagacagTTCGGCAATCAGAAAGGGTActgtctcttatacacatctgacgctgccgacgaATCACCAGGTGtgtgtagatctcggtggtcgccgtatcatttTTGTCGACTC<br>(SEQ ID NO: 26) |
| 256_ILL_size_600_TUB | GAGTCGACAAaatgatacggcgaccaccgagatctacactctttccctacacgacgctcttccgatctTTCACATCGCCTTGACCTTATCATATTCGTTTTACGTTTGTCAAGCCTCATAGCCGGCAGTTCGAACGTATACGCTCTCTGTGACAGACCTCGAAATACGTAGCTCTACACAATTCTGTGAATTTTCCTTTGTCGCGTGTGAAACACTTCCAATAAAAACTCATATGCGTGAATGTATCTCTATCCATGTTGGTCAGGCTGGTGCCAGATTGGAAACGCCTGCTGGGAGCTCTACTGCTTGGAGCACGGCATCCAGCCCGATGGCCAGATGCCGTCTGACAAGACCGTGGGCGGAGGTGATCACACGTTCAACACCTTCTTCAGCGAGACTGGAGCTGGCAAGCACGTGCCCCGCGCCGTGTTTTGTGGATCTGGAACCCACCGTGGTGCGATGAGGGTCCGTACCGGTACCGTCAGCTGTTCCACCCCGAGCAGCTGATCACTGGTAAGGAGGATGCGGCCAACAACTACagatcggaagagcacacgtctgaactccagtcacAATCAGTCTCGTatctcgtatgccgtcttctgcttgTTGTCGACTCTAGGATAACAGGGTAATGAGTCGACAAcaagcagaagacggcatacgagatTGGTCAACGATAgtctcgtgggctcggagatgtgtataagagacagTTAGGACCGGATTAGGTTCActgtctcttatacacatctgacgctgccgacgaATCACCAGGTGtgtgtagatctcggtggtcgccgtatcattTTGTCGACTC<br>(SEQ ID NO: 27) |
| 257_ILL_size_750_TUB | GAGTCGACAAaatgatacggcgaccaccgagatcctacactctttccctacacgacgctttccgatctTGGTACTGCCTCCTGGCCTCTCATATTCGTTTTACGTTTGTCAAGCCTCATAGCCGGCAGTTCGAACGTATACGCTCTCTGTGACAGACCTCGAAATCGTAGCTCTACACAATTCTGTGAATTTTCCTTGTCGCGTGTGAAACACTTCCAATAAAAACTCAATATGCGTGAATGTATCTCTATCCATGTTGGTCAGCGTGGGCGAGGTGATCACACGTTCAACACCTTAGCTGGTGTCCAGATTGGAAACGCCTGCTGGGAGCTCTACTGCTTGGAGCACGGCATCCAGCCCGATGGCCAGATGCCGTCTGACAAGACCTTCAGCGGACTGGAGCTGGCAAGCACGTGCCCCGCGCCGTG |

TABLE 1 -continued

Synthetic Size Standards

| Size Standard | Sequence |
|---|---|
| | TTTGTGGATCTGGAACCCACTGTGGTCGATGAG<br>GTCCGTACCGGAACCTACCGTCAGCTGTTCCAC<br>CCCGAGCAGCTGATCACTGGTAAGGAGGATGCG<br>GCCAACAACTACGCCCGTGGCCACTACACCATC<br>GGCAAGGAGATCGTCGATCTGGTTCTGGACAGG<br>ATCCGCAAGCTGGCCGATCAGTGCACCGGTCTG<br>CAGGGCTTCCTCATCTTCCACTCGTTCGGTGGA<br>GGTACCGGCTCCGGCTTCACCTCGCTGCTGaga<br>tcggaagagcacacgtctgaactccagtcacAA<br>TCAGTCTCGTatctcgtatgccgtcttctgctt<br>gTTGTCGACTCTAGGGATAACAGGGTAATGAGT<br>CGACAAcaagcagaagacggcatacgagatTGG<br>TCAACGATAgtctcgtgggctcggagatgtgta<br>taagagacagAGACCTCGGACGAGGCTCACctg<br>tctcttatacacatctgacgctgccgacgaATC<br>ACCAGGTGTgtgtagatctcggtggtcgccgta<br>tcattTTGTCGACTC<br>(SEQ ID NO: 28) |
| 258_ILL_<br>size_900_<br>TUB | GAGTCGACAAaatgatacggcgaccaccgagat<br>ctacactctttccctacacgacgctcttccgat<br>ctCGACCGTCATTGACGGCCCTTCATATTCGTT<br>TTACGTTTGTCAAGCCTCATAGCCGGCAGTTCG<br>AACGTATACGCTCTCTGTGACAGACCTCGAAAT<br>CGTAGCTCTACACAATTCTGTGAATTTTCCTTG<br>TCGCGTGTGAAACACTTCCAATAAAAACTCAAT<br>ATGCGTGAATGTATCTCTATCCATGTTGGTCAG<br>GCTGGTGTCCAGATTGGAAACGCCTGCTGGGAG<br>CTCTACTGCTTGGAGCACGGCATCCAGCCCGAT<br>GGCCAGATGCCGTCTGACAAGACCGTGGGCGGA<br>GGTGATCACACGTTCAACACCTTCTTCAGCGAG<br>ACTGGAGCTGGCAAGCACGTGCCCCGCGCCGTG<br>TTTGTGGATCTGGAACCCACTGTGGTCGATGAG<br>GTCCGTACCGGAACCTACCGTCAGCTGTTCCAC<br>CCCGAGCAGCTGATCACTGGTAAGGAGGATGCG<br>GCCAACAACTACGCCCGTGGCCACTACACCATC<br>GGCAAGGAGATCGTCGATCTGGTTCTGGACAGG<br>ATCCGCAAGCTGGCCGATCAGTGCACCGGTCTG<br>CAGGGCTTCCTCATCTTCCACTCGTTCGGTGGA<br>cacacgtctgaactccagtcacAATCAGTCTCG<br>TaGGTACCGGCTCCGGCTTCACCTCGCTGCTGA<br>TGGAGCGTCTCTCCGTGGACTACGGCAAGAAGT<br>CCAAGCTGGAGTTCGCCATCTACCCAGCCCCCC<br>AGGTGTCCACTGCCGTGGTCGAGCCCTACAACT<br>CCATCCTGACCACCCACACCACCCTGGAGCATT<br>CCGACTGCGCCTTCATGagatcggaagagtctc<br>gtatgccgtcttctgcttgTTGTCGACTCTAGG<br>GATAACAGGGTAATGAGTCGACAAcaagcagaa<br>gacggcatacgagatTGGTCAACGATAgtctcg<br>tgggctcggagatgtgtataagagacagACCTG<br>AAATACACAGTAACCctgtctcttatacacatc<br>tgacgctgccgacgaATCACCAGGTGTgtgtag<br>atctcggtggtcgccgtatcattTTGTCGACTC<br>(SEQ ID NO: 29) |
| 259_ILL_<br>size_1050_<br>TUB | GAGTCGACAAaatgatacggcgaccaccgagat<br>ctacactctttccctacacgacgctcttccgat<br>ctTATCACCAGGGATGCATTGATCATATTCGTT<br>TTACGTTTGTCAAGCCTCATAGCCGGCAGTTCG<br>AAACGTATACGCTCTCTGTGACAGACCTCGAAA<br>TCGTAGCTCTACACAATTCTGTGATTTTCCTTG<br>TCGCGTGTGAAACACTTCCAATAAAAACTCAAT<br>ATGCGTGAATGTATCTCTATCCATGTTGGTCAG<br>GCTGGTGTCCAGATTGGAAACGCCTGCTGGGAG<br>CTCTACTGCTTGGAGCACGGCATCCAGCCCGAT<br>GGCCAGATGCCGTCTGACAAGACCGTGGGCGGA<br>GGTGATCACACGTTCAACACCTTCTTCAGCGAG<br>ACTGGAGCTGGCAAGCACGTGCCCCGCGCCGTG<br>TTTGTGGATCTGGAACCCACTGTGGTCGATGAG<br>GTCCGTACCGGAACCTACCGTCAGCTGTTCCAC<br>CCCGAGCAGCTGATCACTGGTAAGGAGGATGCG<br>GCCAACAACTACGCCCGTGGCCACTACACCATC<br>GGCAAGGAGATCGTCGATCTGGTTCTGGACAGG<br>ATCCGCAAGCTGGCCGATCAGTGCACCGGTCTG<br>CAGGGCTTCCTCATCTTCCACTCGTTCGGTGGA<br>GGTACCGGCTCCGGCTTCACCTCGCTGCTGATG<br>GAGCGTCTCTCCGTGGACTACGGCAAGAAGTCC<br>AAGCTGGAGTTCGCCATCTACCCAGCCCCCCAG<br>CGTGTCCACTGCCGTGGTCGAGCCCTACAACTC<br>CATCCTGACCACCCACACCACCCTGGAGCATTC<br>CGACTGCGCCTTCATGGTCGACAACGAGGCTAT<br>CTACGACATCTGCCGCCGCAATCTGGACATTGA<br>GCGCCCCACGTACACCAACCTGAACCGTCTGAT<br>TGGCCAGATCGTGTCCTCGATTACCGCCTCTCT<br>GCGATTCGATGGTGCCTTAACGTGGATCTGACT<br>agatcggaagagcacacgtctgaactccagtca<br>cAATCAGTCTCGTatctcgtatgccgtcttctg<br>cttgTTGTCGACTCTAGGGATAACAGGGTAATG<br>AGTCGACAAcaagcagaagacggcatacgagat<br>TGGTCAACGATAgtctcgtgggctcggagatgt<br>gtataagagacagTATTGTGTAAGACATTACCG<br>ctgtctcttatacacatctgacgctgccgacga<br>ATCACCAGGTGTgtgtagatctcggtggtcgcc<br>gtatcattTTGTCGACTC<br>(SEQ ID NO: 30) |
| 260_ILL_<br>size_1200_<br>TUB | GAGTCGACAAaatgatacggcgaccaccgagat<br>cctacactctttccctacacgacgctttccgat<br>ctGGGACCATATTTAGTTATCAGTCATATATTCGTT<br>TTACGTTTGTCAAGCCTCATAGCCGGCAGTTCG<br>AACGTATACGCTCTCTGTGACAGACCTCGAAAT<br>CGTAGCTCTACACAATTCTGTGAATTTTCCTTG<br>TCGCGTGTGAAACACTTCCAATAAAAACTCAAT<br>ATGCGTGAATGTATCTCTATCCATGTTGGTCAG<br>GCTGGTGTCCAGATTGGAAACGCCTGCTGGGAG<br>CTCTACTGCTTGGAGCACGGCATCCAGCCCGAT<br>GGCCAGATGCCGTCTGACAAGACCGTGGGCGGA<br>GGTGATCACACGTTCAACACCTTCTTCAGCGAG<br>ACTGGAGCTGGCAAGCACGTGCCCCGCGCCGTG<br>ATTTGTGGATCTGGAACCCACTGTGGTCGATGA<br>GGTCCGTACCGGAACCTACCGTCAGCTGTTCCA<br>CCCCGAGCAGCTGATCACTGGTAAGGAGGATGC<br>GGCCAACAACTACGCCCGTGGCCACTACACCTC<br>GGCAAGGAGATCGTCGATCTGGTTCTGGACAGG<br>ATCCGCAAGCTGGCCGATCAGTGCACCGGTCTG<br>CAGGGCTTCCTCATCTTCCACTCGTTCGGTGGA<br>GGTACCGGCTCCGGCTTCACCTCGCTGCTGATG<br>GAGCGTCTCTCCGTGGACTACGGCAAGAAGTCC<br>AAGCTGGAGTTCGCCATCTACCCAGCCCCCCAG<br>AGTGTCCCTGCCGTGGTCGAGCCCTACAACTCC<br>ATCCTGACCACCCACACCACCCTGGAGCATTCC<br>GACTGCGCCTTCATGGTCGACAACGAGGCTATC<br>TACGACATCTGCCGCCGCAATCTGGACATTGAG<br>CGCCCCACGTACACCAACCTGAACCGTCTGATT<br>GGCCAGATCGTGTCCTCGATTACCGCCTCTCTG<br>CGATTCGATGGTGCCTTAACGTGGATCTGACT<br>GAGTTCAGACCAACTTGGTGCCCTACCCACGT<br>ATTCACTTCCCTCCTGGTGACCTACGCCCCCGTT<br>ATCTCCGCCGAGAAGGCCTACCACGAGCAGCTG<br>TCGGTGGCTGAGATCACCAACGCCTGCTTCGAG<br>CCGGCCAACCAGATGGTCagatcggaagagcac<br>acgtctgaactccagtcacAATCAGTCTCGTat<br>ctcgtatgccgtcttctgcttgTTGTCGACTCT<br>AGGGATAACAGGGTAATGAGTCGACAAcaagca<br>gaagacggcatacgagatTGGTCAACGATAgtc<br>tcgtgggctcggagatgtgtataagagacagTG<br>GAGGTATTGCTAATAATGctgtctcttatacac<br>atctgacgctgccgacgaATCACCAGGTGTgtg<br>tagatctcggtggtcgccgtatcattTTGTCGA<br>CTC (SEQ ID NO: 31) |
| 261_ILL_<br>size_1350_<br>TUB | GAGTCGACAAaatgatacggcgaccaccgagat<br>ctacactctttccctacacgacgctcttccgat<br>ctCGATTTCTAGGTGTTACTTGTCATATTCGTI<br>CTGTGACAGACCTCGAAATCGTAGCTCTACACA<br>ATTACGTTTGTCAAGCCTCATAGCCGGCAGTTC<br>GAACGTATACGCTCTTTCTGTGAATTTTCCTTG<br>TCGCGTGTGAAACACTTCCAATAAAAACTCAAT<br>ATGCGTGAATGTATCTCTATCCATGTTGGTCAG<br>GCTGGTGTCCAGATTGGAAACGCCTGCTGGGAG |

TABLE 1 -continued

Synthetic Size Standards

| Size Standard | Sequence |
|---|---|
| | CTCTACTGCTTGGAGCACGGCATCCAGCCCGAT |
| | GGCCAGATGCCGTCTGACAAGACCGTGGGCGGA |
| | CGGTGATCACACGTTCAACACCTTCTTCAGCGA |
| | GACTGGAGCTGGCAAGCACGTGCCCCGCGCCGT |
| | GTTTGTGGATCTGGAACCCACTGTGGTCGATGA |
| | GGTCCGTACCGGAACTACCGTCAGCTGTTCCAC |
| | CCCGAGCAGCTGATCACTGGTAAGGAGGATGCG |
| | GCCAACAACTACGCCCGTGGCCACTACACCATC |
| | GGCAAGGAGATCGTCGATCTGGTTCTGGACAGG |
| | AATCCGCAAGCTGGCCGATCAGTGCACCGGTCT |
| | GCAGGGCTTCCTCATCTTCCACTCGTTCGGTGG |
| | AGGTACCGGCTCCGGCTTCACCTCGCTGCTGAT |
| | GGAGCGTCTCTCCGTGGACTACGGCAAGAAGTC |
| | CAAGCTGGAGTTCGCCATCTACCCAGCCCCCCA |
| | GGTGTCCCTGCCGTGGTCGAGCCCTACAACTCC |
| | ATCCTGACCACCCACACCACCCTGGAGCATTCC |
| | GACTGCGCCTTCATGGTCGACAACGAGGCTATC |
| | TACGACATCTGCCGCCGCAATCTGGACATTGAG |
| | CGCCCCACGTACACCAACCTGAACCGTCTGATT |
| | GGCCAGATCGTGTCCTCGATTACCGCCTCTCTG |
| | CGATTCGATGGTGCCCTTAACGTGGATCTGACT |
| | GAGTTCCAGACCAACTTGGTGCCCTACCCACGT |
| | ATTCACTTCCCTCTGGTGACCTACGCCCCCGTT |
| | ATCTCCGCCGAGAAGGCCTACCACGAGCAGCTG |
| | TCGGTGGCTGAGATCACCAACGCCTGCTTCGAG |
| | CCGGCCAACCAGATGGTCAAGTGCGATCCCCGT |
| | CACGGCAAGTACATGGCCTGCTGCATGCTGTAC |
| | CGCGGTGATGTTGTGCCCAAGGACGTCAACGCC |
| | GCTATTGCCACCATCAAGACCAAGCGCACCATT |
| | CAATTCGTCGACTGGTGCCCCACTGGCTTCAAG |
| | GTTagatcggaagagcacacgtctgaactccag |
| | tcacAATCAGTCTCGTatctcgtatgccgtctt |
| | ctgcttgTTGTCGACTCTAGGGATAACAGGGTA |
| | ATGAGTCGACAAcaagcagaagacggcatacga |
| | gatTGGTCAACGATAgtctcgtgggctcggaga |
| | tgtgtataagagacagCCTGCGTGTGCCGTGTA |
| | GGActgtctcttatacacatctgacgctgccga |
| | cgaATCACCAGGTGTgtgtagatctcggtggtc |
| | gccgtatcattTTGTCGACTC |
| | (SEQ ID NO: 32) |
| 262_ILL_size_1500_TUB | GAGTCGACAAaatgatacggcgaccaccgagatctacactctttccctacacgacgctcttccgatctTTTGAGGGTCGCTACAGAATTCATATTCGTT |
| | TTACGTTTGTCAAGCCTCATAGCCGGCAGTTCG |
| | AACGTATACGCTCTCTGTGACAGACCTCGAAAT |
| | CGTAGCTCTACACAATTCTGTGAATTTTCCTTG |
| | TCGCGTGTGAAACACTTCCAATAAAAACTCAAT |
| | ATGCGTGAATGTATCTCTATCCATGTTGGTCAG |
| | GCTGGTGTCCAGATTGGAAACGCCTGCTGGGAG |
| | CTCTACTGCTTGGAGCACGGCATCCAGCCCGAT |
| | GGCCAGATGCCGTCTGACAAGACCGTGGGCGGA |
| | GGTGATCACACGTTCAACACCTTCTTCAGCGAG |
| | ACTGGAGCTGGCAAGCACGTGCCCCGCGCCGTG |
| | TTTGTGGATCTGGAACCCACTGTGGTCGATGAG |
| | GTCCGTACCGGAACTACCGTCAGCTGTTCCAC |
| | CCCGAGCAGCTGATCACTGGTAAGGAGGATGCG |
| | GCCAACAACTACGCCCGTGGCCACTACACCATC |
| | GGCAAGGAGATCGTCGATCTGGTTCTGGACAGG |
| | ATCCGCAAGCTGGCCGATCAGTGCACCGGTCTG |
| | CAGGGCTTCCTCATCTTCCACTCGTTCGGTGGA |
| | GGTACCGGCTCCGGCTTCACCTCGCTGCTGATG |
| | GAGCGTCTCTCCGTGGACTACGGCAAGAAGTCC |
| | AAGCTGGAGTTCGCCATCTACCCAGCCCCCCAG |
| | GTGTCCACTGCCGTGGTCGAGCCCTACAACTCC |
| | ATCCTGACCACCCACACCACCCTGGAGCATTCC |
| | GACTGCGCCTTCATGGTCGACAACGAGGCTATC |
| | TACGACATCTGCCGCCGCAATCTGGACATTGAG |
| | CGCCCCACGTACACCAACCTGAACCGTCTGATT |
| | GGCCAGATCGTGTCCTCGATTACCGCCTCTCTG |
| | CGATTCGATGGTGCCCTTAACGTGGATCTGACT |
| | GAGTTCCAGACCAACTTGGTGCCCTACCCACGT |
| | ATTCACTTCCCTCTGGTGACCTACGCCCCCGTT |
| | ATCTCCGCCGAGAAGGCCTACCACGAGCAGCTG |
| | TCGGTGGCTGAGATCACCAACGCCTGCTTCGAG |

TABLE 1 -continued

Synthetic Size Standards

| Size Standard | Sequence |
|---|---|
| | CCGGCCAACCAGATGGTCAAGTGCGATCCCCGT |
| | CACGGCAAGTACATGGCCTGCTGCATGCTGTAC |
| | CGCGGTGATGTTGTGCCCAAGGACGTCAACGCC |
| | GCTATTGCCACCATCAAGACCAAGCGCACCATT |
| | CAATTCGTCGACTGGTGCCCCACTGGCTTCAAG |
| | GTTGGCATCAACTACCAGCCACCCACCGTGGTG |
| | CCTGGAGGTGATTTGGCCAAGGTGCAGCGTGCC |
| | GTGTGCATGTTGTCCAACACCACGGCCATCGCC |
| | GAGGCCTGGGCCCGTCTGGACCACAAGTTCGAT |
| | CTGATGTACGCCAAGCGTGCCagatcggaagag |
| | cacacgtctgaactccagtcacAATCAGTCTCG |
| | TatctcgtatgccgtcttctgcttgTTGTCGAC |
| | TCTAGGGATAACAGGGTAATGAGTCGACAAcaa |
| | gcagaagacggcatacgagatTGGTCAACGATA |
| | gtctcgtgggctcggagatgtgtataagagaca |
| | gTGGTTTCACCTCACGACAAGctgtctcttata |
| | cacatctgacgctgccgacgaATCACCAGGTGT |
| | gtgtagatctcggtggtcgccgtatcattTTGT |
| | CGACTC |
| | (SEQ ID NO: 33) |

Example 2—Construction and Use of PhiX Size Standards

To demonstrate a proof-of-concept, 177 individually cloned PhiX inserts were selected which spanned a range of sequenceable construct sizes ranging from 169-1524 bp. These constructs were quantified using a Quant-iT PicoGreen dsDNA assay (Thermo Fisher Scientific), diluted the plasmids to an equimolar concentration and pooled. Next, the PhiX size standard plasmid pool was digested with MlyI to liberate the PhiX size standards as previously described. The digested plasmid pool was sequenced according to the Illumina® NextSeq Denature and Dilute Libraries Guide in a portion of a NextSeq 550 lane.

In the resulting sequencing data, barcode sequences were counted using a custom Python script. Since unique starting sequences are necessary to identify individual constructs, and constructs in the pool which had duplicate 5′ break points were excluded from the analysis, as were any constructs for which Sanger sequencing data indicated the presence of an internal MlyI site or a mutation affecting the p5 or p7 sequencing adapter. The remaining 149 constructs were used to measure size bias in the NextSeq run. Sequences of PhiX size standard insert molecules are set forth in the accompanying sequence listing as SEQ ID NOS:37-185. The PhiX size standard data was plotted and compared to the previously described PCR-free quantification barcode size standard constructs (FIG. 9). These measurements agreed well, indicating that the PhiX size standards report accurately on Illumina® sequencer size bias.

Methods and Materials

In order to generate a collection of PhiX size standard molecules with a range of fragment insert sizes, PhiX174 genomic DNA (Genbank-EMBL Accession Numbers NC_001422, Promega) was quantified using a Quant-iT PicoGreen dsDNA assay (Thermo Fisher Scientific). Next, 0.5 ng, 1 ng, 1.67 ng, 3 ng, 5 ng of PhiX174 DNA was tagmented (fragmented and tagged with sequencing adapters) using scaled down (¹⁄₁₀th scale) reactions with the Nextera™ DNA Library Prep Kit (Illumina®) to produce a collection of adapter-tagged molecules that span a length distribution from around 150 bp to greater than 2 kb. These constructs were amplified with the following primers to add flow cell adapters, indices, and the MlyI restriction sites to allow for eventual PCR-free liberation of the standard molecules from the standard plasmids:

PhiX_PCRFBC_Indexing_F:
(SEQIDNO:34)
GAGTCGACAAaatgatacggcgaccaccgag atctacacACACAGGTtcgtcggcagcgtc PhiX_PCRFBC_Indexing_R:
(SCQIDNO:35)
GAGTCGACAAcaagcagaagacggcatacga gatTCAACGGCgtctcgtgggctcgg The amplifications were carried out with KAPA HiFi HotStart polymerase (Roche). The amplified adapter and Mly restriction site-containing PhiX molecules were purified with 2×AmPureXP beads (Beckman Coulter), eluted in 25 μl of EB (Qiagen), then A-tailed using Taq polymerase (Qiagen) with dATP incubated at 72° C. for 30 minutes. The A-Tailed library fragments were cloned into the pCR2.1 TOPO cloning vector (Thermo Fisher) by incubation of the following reaction at room temperature for 30 minutes: 3 μl A-tailed DNA, 1 μl salt solution, 1 μl water, 1 μl pCR 2.1 TOPO vector. 2 μl of each reaction was transformed into a vial of OneShot Top10 competent cells (Thermo Fisher), by incubating on ice for 30 minutes, and heat shocking for 30 seconds at 42° C. 250 μl of SOC media was added to each vial and the reactions were incubated at 37° C. for 1 hour, with shaking at 200 RPM. Cells were then plated on LB plates with ampicillin (100 μg/ml) with 40 μl of 40 mg/ml X-Gal (Promega). Next, a collection of several hundred white colonies were picked, re-streaked onto LB ampicillin (100 μg/ml) plates and single colonies were transferred into deep well 96 well plates with 1 ml of LB ampicillin (100 μg/ml) liquid media, plates were sealed with Breathe Easy seals (Qiagen) and cultures were grown overnight with shaking at 350 RPM. Cells were pelleted and DNA was isolated using a QIAPrep 96 Turbo Miniprep Kit (Qiagen). In order to identify the breakpoints of the PhiX fragments, plasmids were analyzed by Sanger sequencing (Sanger et al., *Proc. Natl. Acad. Sci. U.S.A.* 74:5463-7 (1977)).

---

We claim:

1. A composition comprising a plurality of synthetic size standard polynucleotides, each synthetic size standard polynucleotide of the plurality comprising one or more next-generation sequencing adapter-flanked barcodes, wherein the plurality comprises defined ratios of synthetic size standard polynucleotides of at least two defined lengths, the plurality defining a continuous or random length distribution spanning a defined portion of a genome.

2. The composition of claim 1, wherein each synthetic size standard polynucleotide of the plurality has a defined length.

3. The composition of claim 1, wherein the size standard polynucleotides comprise random genomic fragments of said defined portion of known sizes.

4. The composition of claim 1, wherein the synthetic size standard polynucleotides comprise nucleotides from a 16S rRNA gene, a GAPDH gene, an alpha-tubulin gene, or a PhiX174 genome.

5. The composition of claim 1, wherein each synthetic standard polynucleotide is flanked by cut sites of a restriction enzyme.

6. The composition of claim 1, wherein each synthetic standard polynucleotide comprises a feature allowing PCR-free quantitation of the synthetic standard.

7. The composition of claim 1, wherein the synthetic size standard polynucleotides are encoded on a plasmid.

8. The composition of claim 1, wherein the synthetic size standard polynucleotides are produced by direct in vitro synthesis or PCR amplification.

9. A method for detecting size bias in a sample comprising one or more template polynucleotides, the method comprising obtaining a sample comprising one or more template polynucleotides;

spiking the sample with a plurality of synthetic size standard polynucleotides designed to detect size bias between two template polynucleotides of the sample, each synthetic size standard polynucleotide of the plurality comprising a next-generation sequencing adapter-flanked size barcode, wherein the plurality comprises defined ratios of synthetic size standard polynucleotides of multiple defined lengths;

sequencing at least a portion of each template polynucleotide of the spiked sample using a sequencer corresponding to the next-generation sequencing adapter;

measuring the frequency of occurrence of the size barcode; and comparing the measured occurrence of the size barcodes to an expected frequency occurrence of the size barcodes, thereby generating a size standard polynucleotide size bias value.

10. The method of claim 9, wherein each synthetic size standard polynucleotide is encoded by a plasmid; wherein each next-generation sequencing adapter-flanked size barcode is flanked by one or more restriction enzyme sites; and wherein the method further comprises contacting the spiked sample to one or more restriction enzymes that cleave at the one or more restriction enzyme sites, thereby liberating size barcodes of the plurality from the plasmids.

11. The method of claim 10, wherein the restriction enzyme is selected from MlyI, BsmI, Bts$^\alpha$I, BsrDI, and SbfI.

12. The method of claim 9, wherein the synthetic size standards comprise nucleotides from a 16S rRNA gene, a GAPDH gene, an alpha-tubulin gene, or a PhiX174 genome.

13. The method of claim 9, wherein each synthetic size standard polynucleotide of the plurality further comprises a next generation sequencing adapter-flanked normalization barcode and wherein the frequency of the normalization barcode is measured and compared to an expected frequency of occurrence.

* * * * *